United States Patent
Sugane et al.

(10) Patent No.: US 10,710,988 B2
(45) Date of Patent: Jul. 14, 2020

(54) PIPERAZINE DERIVATIVE

(71) Applicant: Astellas Pharma Inc., Chuo-ku (JP)

(72) Inventors: Takashi Sugane, Tokyo (JP); Norio Asai, Tokyo (JP); Hiroyuki Moritomo, Tokyo (JP); Daisuke Yamashita, Tokyo (JP); Naomi Hosogai, Tokyo (JP)

(73) Assignee: Astellas Pharma Inc., Chuo-ku (JP)

( * ) Notice: Subject to any disclaimer, the term of this patent is extended or adjusted under 35 U.S.C. 154(b) by 0 days.

(21) Appl. No.: 16/314,730

(22) PCT Filed: Jul. 18, 2017

(86) PCT No.: PCT/JP2017/025842
§ 371 (c)(1),
(2) Date: Jan. 2, 2019

(87) PCT Pub. No.: WO2018/016458
PCT Pub. Date: Jan. 25, 2018

(65) Prior Publication Data
US 2019/0202815 A1 Jul. 4, 2019

(30) Foreign Application Priority Data

Jul. 19, 2016 (JP) ................................. 2016-141542

(51) Int. Cl.
| | | |
|---|---|---|
| C07D 405/14 | (2006.01) | |
| C07D 401/14 | (2006.01) | |
| C07D 403/06 | (2006.01) | |
| C07D 241/04 | (2006.01) | |
| C07D 207/12 | (2006.01) | |
| C07D 309/14 | (2006.01) | |
| C07D 307/20 | (2006.01) | |
| A61P 13/02 | (2006.01) | |
| A61P 13/10 | (2006.01) | |
| A61K 31/496 | (2006.01) | |
| A61P 43/00 | (2006.01) | |

(52) U.S. Cl.
CPC .......... *C07D 405/14* (2013.01); *A61K 31/496* (2013.01); *A61P 13/02* (2018.01); *A61P 13/10* (2018.01); *A61P 43/00* (2018.01); *C07D 207/12* (2013.01); *C07D 241/04* (2013.01); *C07D 307/20* (2013.01); *C07D 309/14* (2013.01); *C07D 401/14* (2013.01); *C07D 403/06* (2013.01)

(58) Field of Classification Search
CPC ........ A61K 31/496; A61P 13/02; A61P 13/10; A61P 43/00; C07D 309/14; C07D 401/14; C07D 207/12; C07D 307/20; C07D 405/14; C07D 241/04; C07D 403/06
See application file for complete search history.

(56) References Cited

U.S. PATENT DOCUMENTS

| | | | |
|---|---|---|---|
| 10,301,286 B2 * | 5/2019 | Sugane | ............... C07D 403/06 |
| 2003/0220324 A1 | 11/2003 | Fotsch et al. | |
| 2005/0192286 A1 | 9/2005 | Tran et al. | |
| 2008/0234280 A1 * | 9/2008 | McMurray | ........... A61K 31/454 514/252.03 |

FOREIGN PATENT DOCUMENTS

| | | |
|---|---|---|
| JP | 2005-503369 A1 | 2/2005 |
| JP | 2009-503048 A | 1/2009 |
| WO | WO 03/009850 A1 | 2/2003 |
| WO | WO 03/061660 A1 | 7/2003 |
| WO | WO 2004/078717 A1 | 9/2004 |
| WO | WO 2005/040109 A1 | 5/2005 |
| WO | WO 2006/020277 A2 | 2/2006 |
| WO | WO 2007/015157 A2 | 2/2007 |

OTHER PUBLICATIONS

International Search Report dated Sep. 12, 2017 in corresponding PCT/JP2017/025842 with English translation.
Written Opinion dated Sep. 12, 2017 in corresponding PCT/JP2017/025842 with English translation.
Qingmei Hong, et al., Optimization of privileged structures for selective and potent melanocorting subtypo-4 receptor ligands, Bioorganic & Medicinal Chemistry Letters, 2010, vol. 20, (15), pp. 4483-4486.
Caroline W. Chen, et al., "Synthesis and characterization of trans-4-(4-chlorophenyl) pyrrolididne-3-carboxamides of piperazinecyclohexanes as ligands for the melanocortin-4 receptor", Bioorganic & Medicinal Chemistry Letters, 2007, vol. 17, (24), pp. 6825-6831.

* cited by examiner

*Primary Examiner* — Alexander R Pagano
*Assistant Examiner* — Ebenezer O Sackey
(74) *Attorney, Agent, or Firm* — Oblon, McClelland, Maier & Neustadt, L.L.P.

(57) ABSTRACT

[Problem] To provide a compound useful as an $MC_4$ receptor agonist.
[Means for Solution] The present inventors studied $MC_4$ receptor agonists, and have found that a piperazine derivative has an $MC_4$ receptor agonistic action, thereby completing the present invention. The piperazine derivative of the present invention has an $MC_4$ receptor agonistic action, and can be used as an agent for preventing or treating bladder and/or urinary tract diseases, in particular, underactive bladder, hypotonic bladder, acontractile bladder, detrusor underactivity, neurogenic bladder, urethral relaxation failure, detrusor-external urethral sphincter dyssynergia, and voiding dysfunctions in benign prostatic hyperplasia.

15 Claims, No Drawings

PIPERAZINE DERIVATIVE

CROSS REFERENCE TO RELATED APPLICATIONS

This application is a 371 of International Patent Application No. PCT/JP2017/025842, filed on Jul. 18, 2017, and claims priority to Japanese Patent Application No. 2016-141542, filed on Jul. 19, 2016.

TECHNICAL FIELD

The present invention relates to a piperazine derivative or a salt thereof which has a melanocortin 4 receptor (hereinafter, referred to as an $MC_4$ receptor) agonistic action and can be used as an active ingredient of a pharmaceutical composition such as a pharmaceutical composition for preventing or treating bladder and/or urinary tract diseases.

BACKGROUND ART

Urine storage and voiding are important roles of the lower urinary tract and regulated by a coordinated action of the bladder and the urethra. That is, during urine storage, the bladder smooth muscle is relaxed while the urethral smooth muscle and the external urethral sphincter are contracted, whereby a state of high urethral resistance is maintained, and urinary continence is maintained. On the other hand, during voiding, the bladder smooth muscle is contracted, the urethral smooth muscle is relaxed, and the contraction of the external urethral sphincter is also suppressed. Examples of dysfunctions in the lower urinary tract include urine storage dysfunctions such as overactive bladder in which urine cannot be retained during urine storage, and voiding dysfunctions in which urine cannot be drained sufficiently during voiding due to an increase in the urethral resistance or a decrease in the contractile force of the bladder. In some cases, these two dysfunctions simultaneously develop.

Voiding dysfunctions are caused by an increase in the urethral resistance or a decrease in the bladder contractile force during voiding, and lead to voiding difficulty, straining during voiding, attenuation of the urinary stream, extension of voiding time, an increase in residual urine, a decrease in voiding efficiency, or the like. As a cause of an increase in the urethral resistance, a voiding dysfunction accompanied by benign prostatic hyperplasia is well-known, which is characterized by partial obstruction of the urethra due to nodular hypertrophy of the prostate tissues. Currently, adrenergic $\alpha_1$ receptor antagonists are being used as therapeutic drugs for the voiding dysfunction associated with benign prostatic hyperplasia (Pharmacology, 65, 119-128 (2002)). An increase in the urethral resistance is also caused by functional obstruction in detrusor-external urethral sphincter dyssynergia or the like resulting from neurological diseases or neurological disorders. In patients with these diseases, the effectiveness of adrenergic $\alpha_1$ receptor antagonists is unclear (Journal of Pharmacological Sciences, 112, 121-127 (2010)).

Meanwhile, as a factor for decreasing the contractile force of the bladder during voiding, aging, diabetes, benign prostatic hyperplasia, neurological diseases such as Parkinson's disease and multiple sclerosis, spinal cord injury, nerve damage caused by pelvic surgery, and the like are known (Reviews in Urology, 15, 11-22 (2013)). As therapeutic drugs for a decrease in the bladder contractile force during voiding, bethanechol chloride which is a non-selective muscarinic receptor agonist and distigmine bromide which is a cholinesterase inhibitor are known. However, these drugs are known to have cholinergic side effects such as diarrhea, abdominal pain, sweating, and the like. Furthermore, cholinergic crisis is expressed as a serious side effect in some cases, and accordingly, caution is required in using the drugs (UBRETID (registered trademark) tablet 5 mg package insert, Torii Pharmaceutical Co., Ltd., Besacolin (registered trademark) powder 5% package insert, Eisai Co., Ltd.).

In voiding dysfunctions caused by an increase in the urethral resistance or a decrease in the bladder contractile force as described above, residual urine after voiding may be observed in some cases. Increased residual urine may cause a decrease in effective bladder capacity, and this leads to overactive bladder symptoms such as urinary frequency, or severe symptoms such as hydronephrosis in some cases. Therefore, there is a demand for a therapeutic drug which is more effective on bladder and/or urinary tract diseases or symptoms thereof caused by an increase in the urethral resistance during voiding or a decrease in the bladder contractile force (Reviews in Urology, 15, 11-22 (2013)).

Melanocortins are peptides generated by the processing from proopiomelanocortin, and examples thereof include an adrenocorticotropic hormone, and α-, β-, and γ-melanocyte stimulating hormones (α-, β-, and γ-MSH). Hitherto, five subtypes ($MC_1$ to $MC_5$) of melanocortin receptor (MC receptor) have been reported. Any of the subtypes belongs to a G protein-coupled receptor of a class A, and activates an adenylate cyclase via the Gs protein so as to increase the amount of cAMPs. The $MC_4$ receptors are widely distributed in the central nervous system, and are known to play an important role in feeding behavior, energy metabolism regulation, sexual function, and the like (Folia Pharmacologica Japonica, 128, 53-55 (2006)).

As representative $MC_4$ receptor agonists, the following compounds have been reported.

It is described that a compound represented by the formula (A) has an $MC_4$ receptor agonistic action and is useful for treating and/or preventing diseases relating to the activation of the $MC_4$ receptor, such as obesity, diabetes, and sexual dysfunction (in particular, erectile dysfunction). (Patent Document 1)

[Chem. 1]

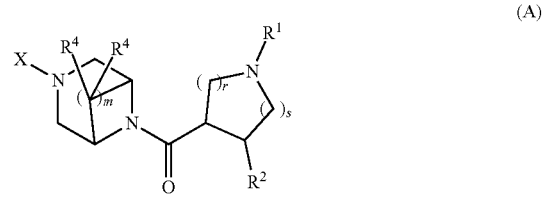

(A)

(In the formula, $R^1$ represents a $C_{1-10}$ alkyl group which may be substituted with $R^3$ or the like, $R^2$ represents phenyl which may be substituted with $R^3$ or the like, X represents $C_{1-8}$ alkyl which may be substituted with $R^3$ or the like, and m represents 0 or the like. See Patent Document 1 for other symbols.)

It is described that some compounds including the compounds of the following formulae (B) and (C) have a binding activity with respect to a human $MC_4$ receptor. (Non-Patent Document 1)

[Chem. 2]

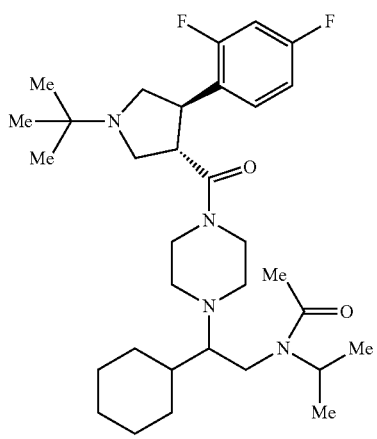

(B)

(C)

It is described that a compound represented by the formula (D) has an MC₄ receptor agonist action and is useful for treating and/or preventing diseases relating to the activation of the MC₄ receptor, such as obesity, diabetes, and sexual dysfunction (in particular, erectile dysfunction). (Patent Document 2)

[Chem. 3]

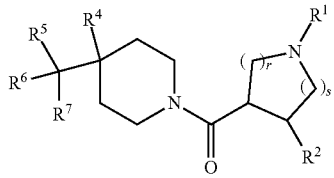

(D)

(In the formula, $R^1$ represents a $C_{1-8}$ alkyl group which may be substituted with $R^3$ or the like, and $R^2$ represents phenyl which may be substituted with $R^9$ or the like. See Patent Document 2 for other symbols.)

It is described that a compound represented by the formula (E) can be used as a ligand of a melanocortin receptor, for treating diseases such as feeding disorder, obesity, inflammation, pain, chronic pain, skin disorder, skin and hair pigmentation, sexual dysfunction, dry eyes, acne, anxiety neurosis, depression, Cushing's disease, and the like. (Patent Document 3)

[Chem. 4]

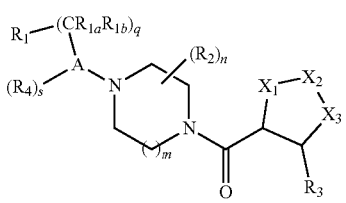

(E)

(In the formula, A represents $C_{5-7}$ cycloalkyl, aryl, or heteroaryl, $X_1$ and $X_3$ represent $CR_5R_6$ or the like, $X_2$ represents $NR_8$, and $R_3$ represents aryl which may be substituted. See Patent Document 3 for other symbols.)

It is described that some compounds including the compounds of the following formulae (F) and (G) have a binding activity with respect to a human MC₄ receptor. (Non-Patent Document 2)

[Chem. 5]

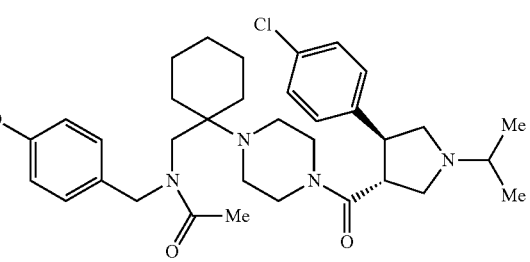

(F)

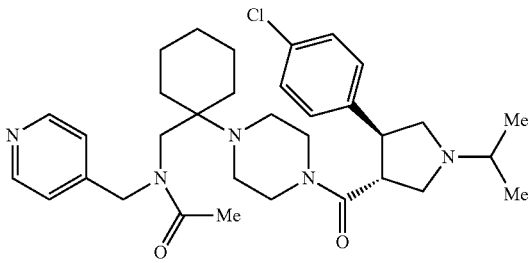

(G)

RELATED ART

Patent Document

[Patent Document 1] WO 2004/078717
[Patent Document 2] WO 2006/020277
[Patent Document 3] WO 2005/040109

Non-Patent Document

[Non-Patent Document 1] Bioorganic Medicinal Chemistry Letters 2010, 20(15), 4483
[Non-Patent Document 2] Bioorganic Medicinal Chemistry Letters 2007, 17(24), 6825

DISCLOSURE OF INVENTION

Problems to be Solved by the Invention

The present invention provides a piperazine derivative which has an MC₄ receptor agonistic action and can be used as an active ingredient of a pharmaceutical composition for preventing or treating bladder and/or urinary tract diseases.

Means for Solving the Problems

The present inventors conducted extensive studies for creating a novel therapeutic drug for bladder and/or urinary tract diseases. As a result, they have found that an $MC_4$ receptor agonist relaxes the urethra and decreases the urethral pressure. Furthermore, the present inventors have found that in rat models with drug-induced voiding dysfunction, there is a decrease inhibiting action in voiding efficiency and an increase inhibiting action in the amount of the residual urine (WO2017/022733).

On the other hand, each of known $MC_4$ receptor agonists have an action on central nervous system such as feeding disorders, obesity, sexual disorder, and the like. In a case where the agonists are used for preventing or treating bladder and/or urinary tract diseases, it is not preferable that the $MC_4$ receptor agonists express an action on central nervous system (for example, an erection-inducing action) when administered at an effective amount. From this viewpoint, the present inventors have considered it is preferable to separate the action on bladder and/or urinary tract diseases from the action on central nervous system. Therefore, for the purpose of creating a compound having a potent action on bladder and/or urinary tract diseases, the present inventors have conducted further extensive studies.

As a result, the present inventors have found that a piperazine derivative as a compound of the formula (I) has an excellent $MC_4$ receptor agonistic activity, and have also discovered that the piperazine derivative can be used as a drug for preventing or treating bladder and/or urinary tract diseases, thereby completing the present invention.

That is, the present invention relates to a compound of the formula (I) or a salt thereof, as well as a pharmaceutical composition comprising a compound of the formula (I) or a salt thereof and a pharmaceutically acceptable excipient.

[Chem. 6]

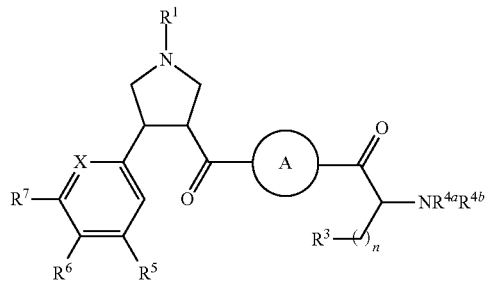

(I)

(wherein,
Ring A represents

[Chem. 7]

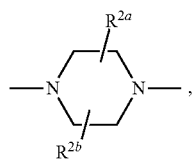

$R^1$ represents $C_{1-6}$ alkyl which may be substituted, $C_{3-8}$ cycloalkyl which may be substituted, or a saturated hetero ring which may be substituted, $R^{2a}$ and $R^{2b}$ are the same as or different from each other and each represent H or $C_{1-6}$ alkyl which may be substituted, $R^{2a}$ and $R^{2b}$ do not simultaneously represent H, in a case where $R^{2a}$ and $R^{2b}$ are bonded to the same carbon, $R^{2a}$, $R^{2b}$, and the carbon atom to which they are bonded may form a saturated hydrocarbon ring together, $R^3$ represents $C_{1-6}$ alkyl which may be substituted, $C_{3-8}$ cycloalkyl which may be substituted, or phenyl which may be substituted, $R^{4a}$ represents H, $C_{1-6}$ alkyl, —C(O)$R^9$, or —S(O)$_2R^9$, $R^{4b}$ represents H or $C_{1-6}$ alkyl, X represents $CR^8$ or N, $R^5$, $R^6$, $R^7$, and $R^8$ are the same as or different from each other and each represent H or halogen, $R^9$ represents $C_{1-6}$ alkyl which may be substituted or $C_{3-8}$ cycloalkyl which may be substituted, and n represents 0 or 1.)

In addition, unless otherwise specified, when symbols in a certain chemical formula in the present specification are also used in another chemical formula, the same symbol represents the same meaning.

The present invention also relates to a pharmaceutical composition for preventing or treating bladder and/or urinary tract diseases, comprising the compound of the formula (I) or a salt thereof. The pharmaceutical composition includes an agent for preventing or treating bladder and/or urinary tract diseases, comprising the compound of the formula (I) or a salt thereof.

The present invention relates to use of the compound of the formula (I) or a salt thereof for the manufacture of a pharmaceutical composition for preventing or treating bladder and/or urinary tract diseases; use of the compound of the formula (I) or a salt thereof for preventing or treating bladder and/or urinary tract diseases; the compound of the formula (I) or a salt thereof for use in preventing or treating bladder and/or urinary tract diseases; and a method for preventing or treating bladder and/or urinary tract diseases, comprising administering to a subject an effective amount of the compound of the formula (I) or a salt thereof.

The present invention also relates to the compound of the formula (I) or a salt thereof which is a $MC_4$ receptor agonist; the compound of the formula (I) or a salt thereof for use as a $MC_4$ receptor agonist; and a $MC_4$ receptor agonist comprising the compound of the formula (I) or a salt thereof.

In addition, the "subject" is a human or another animal in need of such prevention or treatment, and in a certain embodiment, a human in need of such prevention or treatment.

Effects of the Invention

The compound of the formula (I) or a salt thereof is a compound having a peripheral $MC_4$ receptor agonistic activity. The action on bladder and/or urinary tract diseases can be separated from the action on central nervous system. Therefore, the compound or a salt thereof is expected to be useful as an active ingredient of a pharmaceutical composition for preventing or treating bladder and/or urinary tract diseases.

EMBODIMENTS FOR CARRYING OUT THE INVENTION

Hereinafter, the present invention will be specifically described.

In the present specification, the "bladder and/or urinary tract diseases" refer to, for example, voiding dysfunctions in underactive bladder, hypotonic bladder, acontractile bladder, detrusor underactivity, neurogenic bladder, urethral relaxation failure, detrusor-external urethral sphincter dyssynergia, overactive bladder, urinary frequency, nocturia, urinary incontinence, benign prostatic hyperplasia, interstitial cystitis, chronic prostatitis, urethral calculus, and the like; and, in a certain aspect, voiding dysfunctions in underactive bladder, hypotonic bladder, acontractile bladder, detrusor underactivity, neurogenic bladder, urethral relaxation failure, detrusor-external urethral sphincter dyssynergia, and benign prostatic hyperplasia.

The "$C_{1-6}$ alkyl" refers to linear or branched alkyl having 1 to 6 carbon atoms. Examples thereof include methyl, ethyl, n-propyl, isopropyl, n-butyl, isobutyl, sec-butyl, tert-butyl, n-pentyl, n-hexyl, and the like. (Hereinafter, the number of carbon atoms will be described in the same manner.) In a certain aspect, $C_{1-6}$ alkyl is $C_{1-4}$ alkyl; in a certain aspect, methyl, isopropyl, or tert-butyl; in a certain aspect, isopropyl or tert-butyl; in a certain aspect, methyl; and in a certain aspect, tert-butyl.

The "$C_{3-8}$ cycloalkyl" refers to a saturated hydrocarbon ring group having 3 to 8 carbon atoms, which may have a bridge. Examples thereof include cyclopropyl, cyclobutyl, cyclopentyl, cyclohexyl, and the like. In a certain aspect, $C_{3-8}$ cycloalkyl is $C_{3-6}$ cycloalkyl; in a certain aspect, cyclopropyl; and in a certain aspect, cyclohexyl.

The "saturated hetero ring" refers to a 3- to 8-membered monocyclic saturated heterocyclic group containing one or two hetero atoms selected from oxygen, sulfur, and nitrogen as a ring-constituting atom, in which the sulfur or nitrogen as a ring atom may be oxidized to form an oxide or a dioxide. Examples thereof include azetidinyl, pyrrolidinyl, piperidyl, piperazinyl, azepanyl, diazepanyl, morpholinyl, thiomorpholinyl, oxetanyl, tetrahydrofuranyl, tetrahydropyranyl, dioxolanyl, dioxanyl, tetrahydrothiopyranyl, and the like.

The "oxygen-containing saturated hetero ring" refers to 3- to 8-membered monocyclic saturated heterocyclic group containing one or two oxygen atoms as ring-constituting atoms, among the aforementioned saturated hetero rings. Examples thereof include oxetanyl, tetrahydrofuranyl, tetrahydropyranyl, dioxolanyl, and dioxanyl. In a certain aspect, the oxygen-containing saturated hetero ring is tetrahydrofuranyl or tetrahydropyranyl; in a certain aspect, tetrahydrofuranyl; and in a certain aspect, tetrahydropyranyl.

The "halogen" means F, Cl, Br, or I. In a certain aspect, the halogen is F or Cl; and in a certain aspect, F.

In a case where $R^{2a}$ and $R^{2b}$ on a piperazine ring constituting Ring A are bonded to the same carbon, the saturated hydrocarbon ring which is formed together by $R^{2a}$, $R^{2b}$, and the carbon atoms to which they are bonded is, in a certain aspect, a $C_{3-8}$ saturated hydrocarbon ring; in a certain aspect, $C_{3-6}$ saturated hydrocarbon ring; and in a certain aspect, cyclopropane.

In the present specification, "may be substituted" means that a group has no substituent or has 1 to 5 substituents. In a case where a group has a plurality of substituents, the substituents may be the same as or different from each other.

Examples of substituents acceptable in the "$C_{3-6}$ alkyl which may be substituted", the "$C_{3-8}$ cycloalkyl which may be substituted", the "saturated hetero ring which may be substituted", and the "phenyl which may be substituted" include $C_{1-6}$ alkyl, —O—($C_{1-6}$ alkyl), $C_{3-8}$ cycloalkyl, halogen, cyano, and the like.

In a certain aspect, the substituent acceptable in the "$C_{1-6}$ alkyl which may be substituted" in $R^1$ is —O—($C_{1-6}$ alkyl), $C_{3-8}$ cycloalkyl, halogen, or cyano; in a certain aspect, $C_{3-8}$ cycloalkyl; and in a certain aspect, cyclopropyl.

In a certain aspect, the substituent acceptable in the "$C_{1-6}$ alkyl which may be substituted" in $R^{2a}$ and $R^{2b}$ is —O—($C_{1-6}$ alkyl), $C_{3-8}$ cycloalkyl, halogen, or cyano; in a certain aspect, —O—($C_{1-6}$ alkyl); and in a certain aspect, methoxy.

In a certain aspect, the substituent acceptable in the "$C_{1-6}$ alkyl which may be substituted" in $R^3$ is —O—($C_{1-6}$ alkyl) or halogen.

In a certain aspect, the substituent acceptable in the "$C_{3-8}$ cycloalkyl which may be substituted" in $R^3$ is $C_{1-6}$ alkyl, —O—($C_{1-6}$ alkyl), or halogen; in a certain aspect, $C_{1-6}$ alkyl or halogen; and in a certain aspect, methyl or F.

In a certain aspect, the substituent acceptable in the "phenyl which may be substituted" in $R^3$ is halogen or cyano; and in a certain aspect, F, Cl, or cyano.

Some aspects of the compound of the formula (I) or a salt thereof will be shown below.

(1) A compound or a salt thereof, in which Ring A is

[Chem. 8]

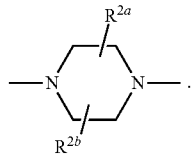

In a certain aspect, a compound or a salt thereof, in which Ring A is

[Chem. 9]

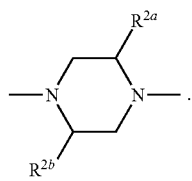

In a certain aspect, a compound or a salt thereof, in which Ring A is

[Chem. 10]

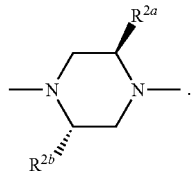

(2) A compound or a salt thereof, in which $R^1$ represents $C_{1-6}$ alkyl which may be substituted, $C_{3-8}$ cycloalkyl which may be substituted, or a saturated hetero ring which may be substituted. In a certain aspect, a compound or a salt thereof, in which $R^1$ represents $C_{1-6}$ alkyl which may be substituted, $C_{3-8}$ cycloalkyl, or an oxygen-containing saturated hetero ring. In a certain aspect, a compound or a salt thereof, in which $R^1$ represents $C_{1-6}$ alkyl or an oxygen-containing saturated hetero ring. In a certain aspect, a compound or a salt thereof, in which $R^1$ represents $C_{1-6}$ alkyl. In a certain aspect, a compound or a salt thereof, in which $R^1$ represents tert-butyl.

(3) A compound or a salt thereof, in which $R^{2a}$ and $R^{2b}$ are the same as or different from each other and each represent H or $C_{1-6}$ alkyl which may be substituted; $R^{2a}$ and $R^{2b}$ do not simultaneously represent H; and in a case where $R^{2a}$ and $R^{2b}$ are bonded to the same carbon, $R^{2a}$, $R^{2b}$, and the carbon atom to which they are bonded may form a saturated hydrocarbon ring together. In a certain aspect, a compound or a salt thereof, in which $R^{2a}$ and $R^{2b}$ are the same as or different from each other and each represent H or $C_{1-6}$ alkyl which may be substituted; $R^{2a}$ and $R^{2b}$ do not simultaneously represent H; and in a case where $R^{2a}$ and $R^{2b}$ are bonded to the same carbon, $R^{2a}$, $R^{2b}$, and the carbon atom to which they are bonded may form a $C_{3-8}$ saturated hydrocarbon ring together. In a certain aspect, a compound or a salt thereof, in which $R^{2a}$ and $R^{2b}$ are the same as or different from each other and each represent H or $C_{1-6}$ alkyl; and $R^{2a}$ and $R^{2b}$ do not simultaneously represent H. In a certain aspect, a compound or a salt thereof, in which $R^{2a}$ and $R^{2b}$ am the same as or different from each other and each represent H or methyl; and $R^{2a}$ and $R^{2b}$ do not simultaneously represent H.

(4) A compound or a salt thereof, in which $R^3$ represents $C_{1-6}$ alkyl which may be substituted, $C_{3-8}$ cycloalkyl which may be substituted, or phenyl which may be substituted. In a certain aspect, a compound or a salt thereof, in which $R^3$ represents $C_{1-6}$ alkyl, $C_{3-8}$ cycloalkyl which may be substituted, or phenyl which may be substituted. In a certain aspect, a compound or a salt thereof, in which $R^3$ represents $C_{1-6}$ alkyl, $C_{3-8}$ cycloalkyl, or phenyl which may be substituted with one or two substituents selected from the group consisting of halogen and cyano. In a certain aspect, a compound or a salt thereof, in which $R^3$ represents $C_{1-6}$ alkyl, $C_{3-8}$ cycloalkyl, or phenyl which may be substituted with one cyano group. In a certain aspect, a compound or a salt thereof, in which when n represents 0, $R^3$ represents $C_{3-8}$ cycloalkyl, and when n represents 1, $R^3$ represents $C_{1-6}$ alkyl. In a certain aspect, a compound or a salt thereof, in which when n represents 0, $R^3$ represents cyclohexyl, and when n represents 1, $R^3$ represents isopropyl or tert-butyl.

(5) A compound or a salt thereof, in which $R^{4a}$ represents H, $C_{1-6}$ alkyl, —C(O)$R^9$, or —S(O)$_2R^9$; and $R^{4b}$ represents H or $C_{1-6}$ alkyl. In a certain aspect, a compound or a salt thereof, in which $R^{4a}$ represents H, $C_{1-6}$ alkyl, —C(O)$R^9$, or —S(O)$_2R^9$; $R^{4b}$ represents H or $C_{1-6}$ alkyl; in a case where $R^{4a}$ represents H, $R^{4b}$ also represents H; and in a case where $R^{4a}$ represents $C_{1-6}$ alkyl, $R^{4b}$ also represents $C_{1-6}$ alkyl. In a certain aspect, a compound or a salt thereof, in which $R^{4a}$ represents —C(O)$R^9$ or —S(O)$_2R^9$; and $R^{4b}$ represents H. In a certain aspect, a compound or a salt thereof, in which $R^{4a}$ represents —C(O)$R^9$; and $R^{4b}$ represents H.

(6) A compound or a salt thereof, in which X represents $CR^8$ or N. In a certain aspect, a compound or a salt thereof, in which X represents $CR^8$.

(7) A compound or a salt thereof, in which $R^5$, $R^6$, $R^7$, and $R^8$ are the same as or different from each other and each represent H or halogen. In a certain aspect, a compound or a salt thereof, in which $R^5$ represents H, $R^6$ represents halogen; $R^7$ represents H; and $R^8$ represents H or halogen. In a certain aspect, a compound or a salt thereof, in which $R^5$ represents H; $R^6$ represents F or Cl; $R^7$ represents H; and $R^8$ represents H or F.

(8) A compound or a salt thereof, in which $R^9$ represents $C_{1-6}$ alkyl which may be substituted or $C_{3-8}$ cycloalkyl which may be substituted. In a certain aspect, a compound or a salt thereof, in which $R^9$ represents $C_{1-6}$ alkyl or $C_{3-8}$ cycloalkyl. In a certain aspect, a compound or a salt thereof, in which $R^9$ represents $C_{1-6}$ alkyl. In a certain aspect, a compound or a salt thereof, in which $R^9$ represents methyl.

(9) A compound or a salt thereof, in which n represents 0 or 1. In a certain aspect, a compound or a salt thereof, in which n represents 0. In a certain aspect, a compound or a salt thereof, in which n represents 1.

(10) A compound which is a combination of two or more groups described above in (1) to (9).

Specifically, examples of the combination described above in (10) include the following aspects.

(11) The compound of the formula (I) or a salt thereof, in which Ring A is

[Chem. 11]

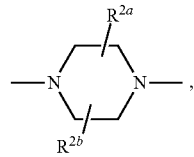

$R^1$ represents $C_{1-6}$ alkyl which may be substituted, $C_{3-8}$ cycloalkyl, or an oxygen-containing saturated hetero ring, $R^{2a}$ and $R^{2b}$ are the same as or different from each other and each represent H or $C_{1-6}$ alkyl which may be substituted, $R^{2a}$ and $R^{2b}$ do not simultaneously represent H, in a case where $R^{2a}$ and $R^{2b}$ are bonded to the same carbon, $R^{2a}$, $R^{2b}$, and the carbon atom to which they are bonded may form a saturated hydrocarbon ring together, $R^3$ represents $C_{1-6}$ alkyl, $C_{3-8}$ cycloalkyl which may be substituted, or phenyl which may be substituted, $R^{4a}$ represents H, $C_{1-6}$ alkyl, —C(O)$R^9$, or —S(O)$_2R^9$, $R^{4b}$ represents H or $C_{1-6}$ alkyl, in a case where $R^{4a}$ represents H, $R^{4b}$ also represents H, and in a case where $R^{4a}$ represents $C_{1-6}$ alkyl, $R^{4b}$ also represents $C_{1-6}$ alkyl, X represents $CR^8$ or N, $R^5$, $R^6$, $R^7$, and $R^8$ are the same as or different from each other and each represent H or halogen, $R^9$ represents $C_{1-6}$ alkyl or $C_{3-8}$ cycloalkyl, and n represents 0 or 1.

(12) The compound or a salt thereof described in (11), in which Ring A is

[Chem. 12]

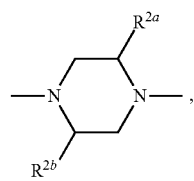

$R^1$ represents $C_{1-6}$ alkyl or oxygen-containing saturated hetero ring, $R^{2a}$ and $R^{2b}$ are the same as or different from each other and each represent H or $C_{1-6}$ alkyl, $R^{2a}$ and $R^{2b}$ do not simultaneously represent H, $R^3$ represents $C_{1-6}$ alkyl, $C_{3-8}$ cycloalkyl, or phenyl which may be substituted with one or two substituents selected from the group consisting of halogen and cyano, $R^{4a}$ represents —C(O)$R^9$ or —S(O)$_2R^9$, $R^{4b}$ represents H, $R^5$ represents H, $R^6$ represents halogen, $R^7$ represents H, $R^8$ represents H or halogen, and $R^9$ represents $C_{1-6}$ alkyl.

(13) The compound or a salt thereof described in (12), in which

Ring A is

[Chem. 13]

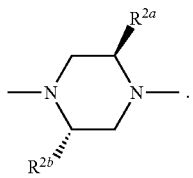

(14) The compound or a salt thereof described in (13), in which $R^3$ represents $C_{1-6}$ alkyl, $C_{3-8}$ cycloalkyl, or phenyl which may be substituted with one cyano group, $R^{4a}$ represents —C(O)$R^9$, $R^{4b}$ represents H, and X represents $CR^8$.

(15) The compound or a salt thereof described in (14), in which $R^1$ represents $C_{1-6}$ alkyl, when n represents 0, $R^3$ represents $C_{3-8}$ cycloalkyl, and when n represents 1, $R^3$ represents $C_{1-6}$ alkyl.

(16) The compound or a salt thereof described in (15), in which $R^1$ represents tert-butyl, $R^{2a}$ and $R^{2b}$ are the same as or different from each other and each represent H or methyl, $R^{2a}$ and $R^{2b}$ do not simultaneously represent H, when n represents 0, $R^3$ represents cyclohexyl, when n represents 1, $R^3$ represents isopropyl or tert-butyl, X represents $CR^8$, $R^6$ represents F or Cl, $R^8$ represents H or F, and $R^9$ represents methyl.

Examples of the specific compounds included in the present invention include following compounds or salts thereof:

N-{((1S)-2-[(3S)-4-{[(3S,4R)-1-tert-butyl-4-(2,4-difluorophenyl)pyrrolidin-3-yl]carbonyl}-3-methylpiperazin-1-yl]-1-cyclohexyl-2-oxoethyl}acetamide, N-{(2S)-1-[(3S)-4-{[(3S,4R)-1-tert-butyl-4-(2,4-difluorophenyl)pyrrolidin-3-yl]carbonyl}-3-methylpiperazin-1-yl]-4,4-dimethyl-1-oxopentan-2-yl}acetamide, N-{(2S)-1-[(2R,5S)-4-{[(3 S,4R)-1-tert-butyl-4-(2,4-difluorophenyl)pyrrolidin-3-yl]carbonyl}-2,5-dimethylpiperazin-1-yl]-4,4-dimethyl-1-oxopentan-2-yl}acetamide, N-{(2S)-1-[(2R,5S)-4-{[1-tert-butyl-4-(4-fluorophenyl)pyrrolidin-3-yl]carbonyl}-2,5-dimethylpiperazin-1-yl]-4,4-dimethyl-1-oxopentan-2-yl}acetamide, and N-{(2S)-1-[(2R)-4-{[(3 S,4R)-1-tert-butyl-4-(4-chloro-2-fluorophenyl)pyrrolidin-3-yl]carbonyl}-2-methylpiperazin-1-yl]-4-methyl-1-oxopentan-2-yl}acetamide.

In the compound of the formula (I), a tautomer or a geometrical isomer can exist depending on the type of substituents. In the present specification, the compound of the formula (I) is described in only one isomer form in some cases. However, the present invention includes other isomers, and also includes compounds from which isomers are separated, or mixtures thereof.

Further, the compound of the formula (I) has asymmetric carbon atoms or axis chirality in some cases, and therefore, optical isomers may exist based on such cases. The present invention also includes the compounds from which optical isomers of the compound of the formula (I) are separated, or mixtures thereof.

The present invention also includes a pharmaceutically acceptable prodrug of the compound of the formula (I). The pharmaceutically acceptable prodrug is a compound having a group that can be converted into an amino group, a hydroxyl group, a carboxyl group, or the like through solvolysis or under physiological conditions. Examples of the group forming the prodrug include the groups described in Prog. Med., 5, 2157-2161 (1985) and "Pharmaceutical Research and Development" (Hirokawa Publishing Company, 1990), Vol. 7, Molecular Design, 163-198.

The salt of the compound of the formula (I) is a pharmaceutically acceptable salt of the compound of the formula (I) and may form an acid addition salt or a salt with a base depending on the type of substituents. Specific examples thereof include acid addition salts with inorganic acids such as hydrochloric acid, hydrobromic acid, hydroiodic acid, sulfuric acid, nitric acid, and phosphoric acid and with organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid, and glutamic acid, and salts with metal cations such as sodium, potassium, magnesium, calcium, and aluminum, salts with organic bases such as methylamine, ethylamine, and ethanolamine, salts with various amino acids and amino acid derivatives such as acetylleucine, lysine, and ornithine, ammonium salts, and the like.

The present invention also includes various hydrates or solvates and polymorphic crystalline substances of the compound of the formula (I) or a salt thereof. In addition, the present invention also includes compounds labeled with various radioactive or non-radioactive isotopes.

(Preparation Method)

The compound of the formula (I) or a salt thereof can be prepared by applying various known synthesis methods using the characteristics based on the basic structure or the type of substituents thereof. At the time of preparation, depending on the type of functional group, from the viewpoint of the preparation technology, it is in some cases effective to substitute the relevant functional group with an appropriate protective group (a group that can be easily converted into the relevant functional group) during the steps from starting material to intermediate. Examples of the aforementioned protective group include the protective groups described in "Greene's Protective Groups in Organic Synthesis (4$^{th}$ edition, 2006)", P. G M. Wuts and T. W. Greene and the like, and the protective group may be appropriately selected and used depending on the reaction conditions thereof. In this method, a desired compound can be obtained by introducing the protective group and carrying out a reaction, and then removing the protective group as necessary.

In addition, prodrugs of the compound of the formula (I) can be prepared by introducing a specific group or by further carrying out the reaction by using the obtained compound of the formula (I) during the steps from starting material to intermediate, just as in the case of the aforementioned protective group. The reaction can be carried out by applying methods known to a person skilled in the art, such as common esterification, amidation, and dehydration.

Hereinafter, typical preparation methods for the compound of the formula (I) will be described. Each production process can also be carried out with reference to the reference documents attached to the description of the production process. The preparation methods of the present invention are not limited to the following examples.

(Production Process 1)

[Chem. 14]

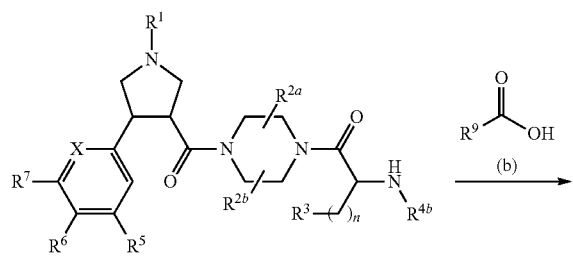

(a)

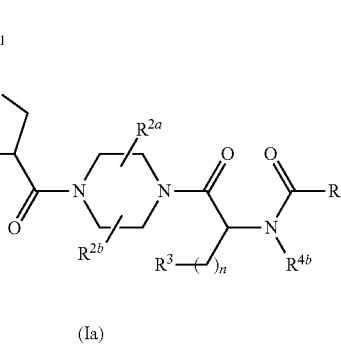

(Ia)

This reaction is a method for preparing a compound of the formula (Ia), in which $R^{4a}$ represents —C(O)$R^9$ in the formula (I) representing the compound of the present invention.

This reaction is carried out using the compound of the formula (a) and the compound of the formula (b) in equivalent amounts, or either thereof in an excess amount, by stirring a mixture in a solvent which is inert to the reaction in the presence of a condensing reagent, under from cooling to heating, preferably at −20° C. to 60° C., usually for 0.1 hours to 5 days. The solvent used herein is not particularly limited, and examples thereof include aromatic hydrocarbons such as benzene, toluene, xylene, and the like, halogenated hydrocarbons such as dichloromethane, 1,2-dichloroethane, chloroform, and the like, ethers such as diethyl ether, tetrahydrofuran, dioxane, dimethoxyethane, and the like, N,N-dimethylformamide, dimethylsulfoxide, ethyl acetate, acetonitrile, water, and a mixture thereof. Examples of the condensing reagent include, but are not limited to, O-(7-aza-1H-benzotriazol-1-yl)-N,N,N',N'-tetramethyluronium hexafluorophosphate (HATU), 1-(3-dimethylaminopropyl)-3-ethylcarbodiimide, dicyclohexylcarbodiimide, 1,1'-carbonyldiimidazole, and diphenylphosphoryl azide, and phosphorous oxychloride. In some cases, it is preferable to use an additive (for example, 1-hydroxybenzotriazole) for the reaction. Furthermore, in some cases, for smooth progress of the reaction, it is advantageous to perform the reaction in the presence of organic bases such as triethylamine, N,N-diisopropyl ethylamine, N-methylmorpholine, and the like or inorganic bases such as potassium carbonate, sodium carbonate, potassium hydroxide, and the like.

Furthermore, it is also possible to use a method in which the compound of the formula (b) is converted into a reactive derivative and then reacted with the compound of the formula (a). Examples of the reactive derivative of the carboxylic acid include acid halides that can be obtained by the reaction with a halogenating agent such as phosphorus oxychloride, thionyl chloride, and the like, mixed acid anhydrides obtained by the reaction with isobutyl chloroformate and the like, and active esters obtained by condensation with 1-hydroxybenzotriazole and the like. The reaction between these reactive derivatives and the compound of the formula (a) can be performed in a solvent which is inert to the reaction such as halogenated hydrocarbons, aromatic hydrocarbons, ethers, and the like, under from cooling to heating, preferably at a temperature of −20° C. to 60° C. In some cases, for smooth progress of the reaction, it is advantageous to perform the reaction in the presence of organic bases such as triethylamine, N,N-diisopropyl ethylamine, N-methylmorpholine, and the like.

[Document]

"Organic Functional Group Preparations ($2^{nd}$ edition)", S. R. Sandler and W. Karo, Vol. 1, Academic Press Inc., 1991

"Courses in Experimental Chemistry ($5^{th}$ edition)" edited by The Chemical Society of Japan, Vol. 16 (2005) (Maruzen)

(Production Process 2)

[Chem. 15]

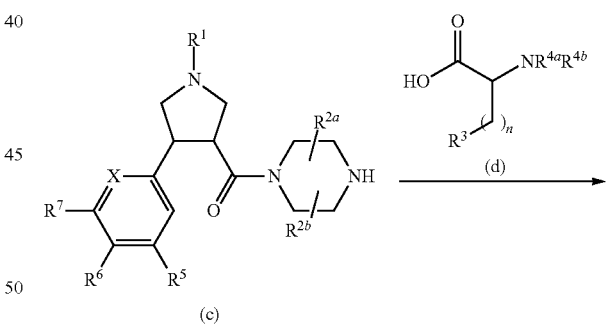

(c)

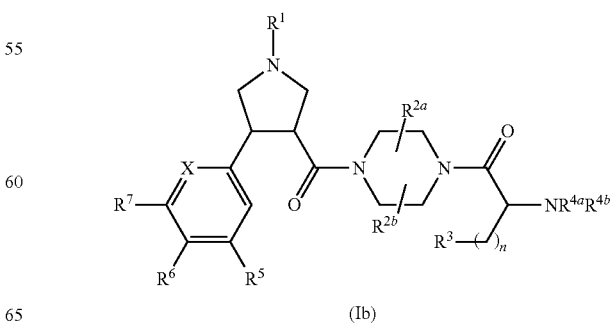

(Ib)

This reaction is a method for preparing the compound of the formula (Ib), in which Ring A in the compound of the formula (I) is

[Chem. 16]

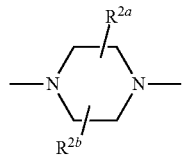

by an amidation reaction between the compound of the formula (c) and the compound of the formula (d).

The reaction conditions are the same as in Production Process 1.

Here, "the compound of the formula (Ib)" and "the compound of the formula (I)" are the same meaning, and refer to the same compound.

(Starting Material Synthesis 1)

[Chem. 17]

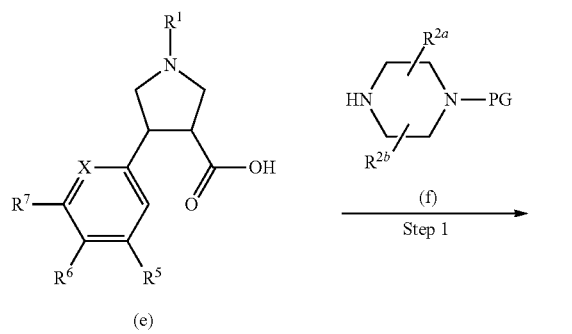

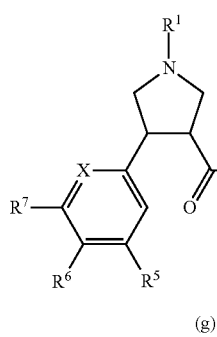

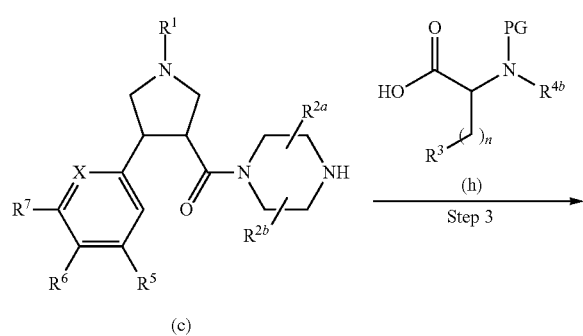

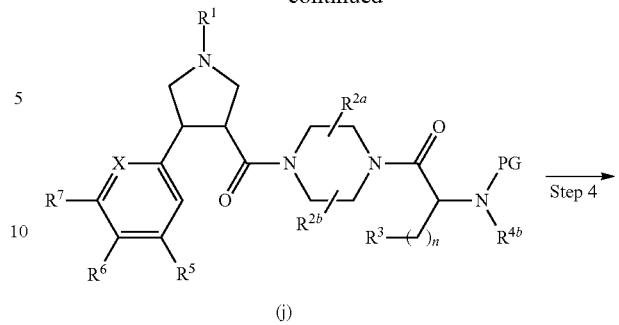

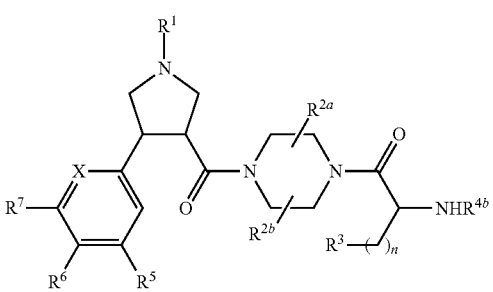

(In the formulae, PG represents a protective group such as tert-butoxycarbonyl group.)

This production process is a method for preparing the compound of the formula (a) that is a starting compound of Production Process 1 and the compound of the formula (c) that is a starting compound of Production Process 2.

(Step 1)

This step is a method for preparing a compound of the formula (g) by an amidation reaction between the compound of the formula (e) and the compound of the formula (f). The reaction conditions are the same as in Production Process 1.

(Step 2)

This step is a method for preparing the compound of the formula (c) by deprotecting the compound of the formula (g). The deprotecting step can be carried out with reference to "Protective Groups in Organic Synthesis (4th edition)" Greene & Wuts, John Wiley & Sons Inc, 2006.

(Step 3)

This step is a method for preparing the compound of the formula (j) by an amidation reaction between the compound of the formula (c) and the compound of the formula (h). The reaction conditions are the same as in Production process 1.

(Step 4)

This step is a method for preparing the compound of the formula (a) by deprotecting the compound of the formula (j). As in Step 2, the deprotecting step can be performed with reference to "Protective Groups in Organic Synthesis (4th edition)" Greene & Wuts, John Wiley & Sons Inc, 2006.

(Starting Material Synthesis 2)

[Chem. 18]

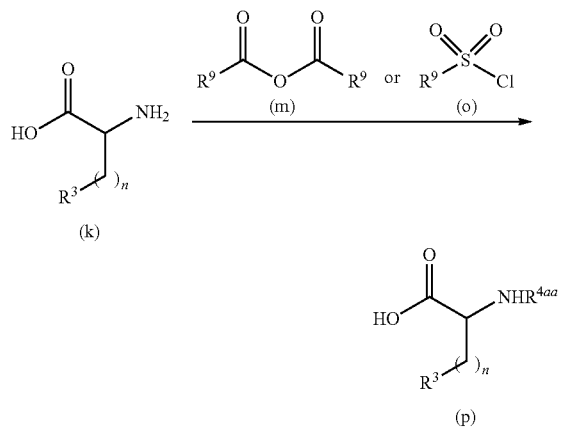

(In the formula, $R^{4aa}$ represents $R^9C(O)$ or $R^9S(O)_2$.)

This production process is a method for preparing the compound of the formula (p), in which $R^{4a}$ represents $R^{4aa}$ and $R^{4b}$ represents H in the compound of the formula (d) that is a starting compound of Production Process 2.

This reaction can be performed in a solvent which is inert to the reaction, such as halogenated hydrocarbons, aromatic hydrocarbons, ethers, and the like, under from cooling to heating, preferably at a temperature of −20° C. to 60° C. In some cases, for smooth progress of the reaction, it is advantageous to carry out the reaction in the presence of organic bases such as triethylamine, N,N-diisopropyl ethylamine, N-methylmorpholine, and the like.

The compound of the formula (I) is purified by being isolated as a free compound, a salt, a hydrate, a solvate, or a polymorphic crystalline substance thereof. The salt of the compound of the formula (I) can also be prepared by a conventional salt formation reaction.

Isolation and purification can be performed through a general chemical operation such as extraction, fractional crystallization, and various types of fractional chromatography techniques.

Various isomers can be prepared by selecting appropriate starting compounds or by separation using differences in physicochemical properties between the isomers. For example, optical isomers can be obtained by means of a general optical resolution method for racemic isomers (for example, fractional crystallization for inducing diastereomer salts with optically active bases or acids, and chromatography using a chiral column or the like). Furthermore, the isomers can also be prepared from an appropriate optically active starting compound.

The pharmacological activities of the compound of the formula (I) were confirmed by the following tests.

TEST EXAMPLES

The pharmacological activities of the compound of the formula (I) were confirmed by the following tests. In the present specification, the doses of the test compounds are expressed in terms of the weight of free forms.

Unless otherwise specified, the present test examples can be performed according to known methods. In a case where commercially available reagents, kits, and the like are used, the present test examples can be performed according to the instructions attached to the commercially available products.

Test Example 1: Test for Evaluating Human MC Receptor Activation, Using Cells Expressing Human $MC_4$, $MC_1$, and $MC_3$ Receptors Experiment Method (1) Construction of Human MC Receptor-Expressing Vector A human $MC_4$ receptor gene (GenBank Accession No.: NM_005912.2), a human $MC_1$ receptor gene (GenBank Accession No.: NM_002386.3), or a human $MC_3$ receptor gene (GenBank Accession No.: NM_019888.3) was introduced into an expression vector pcDNA™ 3.1N/V5-His TOPO (registered trademark) (Thermo Fisher Scientific Inc).

(2) Construction of Cells Transiently Expressing Human MC Receptor

An expression vector for a human $MC_4$, $MC_1$, or $MC_3$ receptor was introduced into FreeStyle™ 293-F cells (Thermo Fisher Scientific Inc., product number: R790-07). For the introduction, electroporation was employed. That is, $1\times10^7$ FreeStyle™ 293-F cells were suspended in 80 μL of an Electroporation Buffer (Thermo Fisher Scientific Inc., product number: B201-100), and 20 μg of the expression vector was added thereto. The resultant was put into a cuvette (OC-100 Processing Assembly, MaxCyte, Inc.) and electroporated with MaxCyte STX (registered trademark) (MaxCyte, Inc.). The cells were cultured for a day, suspended in a Cell Banker (registered trademark) 1 (TAKARA BIO INC. or JUJI FIELD Inc., product number: BLC-1), and stored frozen until they were used.

(3) Measurement of Amount of cAMP Production

Measurement was carried out by using a LANCE (registered trademark) Ultra cAMP Kit (PerkinElmer, Inc.) in accordance with the attached instructions. That is, after dissolution in DMSO, the test compound (a final concentration of 1 pM to 30 μM) diluted with an assay buffer (Hank's balanced salt solution, 5 mM 4-(2-hydroxyethyl)-1-piperazineethanesulfonic acid (HEPES), 0.5 mM 3-isobutyl-1-methylxanthine (IBMX), 0.1% bovine serum albumin, pH 7.4), or α-MSH (Bachem Inc., a final concentration of 1 pM to 30 μM) was added to OptiPlate-384 (PerkinElmer, Inc.). Furthermore, the suspension of the cells transiently expressing the human $MC_4$, $MC_1$, or $MC_3$ receptor prepared using the assay buffer was added thereto at 1,000 cells/well, and then left to stand at room temperature for about 1 hour. Thereafter, an Eu-cAMP tracer solution and an ULight™-anti-cAMP solution were added thereto, and then the resulting solution was left to stand at room temperature for about 1 hour. The amount of cAMP was calculated using EnVision (registered trademark) (PerkinElmer Inc.).

For the agonistic activity, the efficacy ($EC_{50}$ (μM)) was calculated by a non-linear regression method with a Sigmoid-Emax model, by defining the maximum reaction using α-MSH as 100% and the reaction using the vehicle alone as 0%, respectively.

The $EC_{50}$ values of some example compounds of the present invention are shown in Table 1. Ex represents the Example No. of the test compound, and NT represents Not Tested.

TABLE 1

| Ex | EC$_{50}$ (μM) | | |
|---|---|---|---|
| | MC$_4$ | MC$_1$ | MC$_3$ |
| 3 | 0.008 | 5.7 | 0.31 |
| 4 | 0.0068 | 1 | 0.27 |
| 5 | 0.006 | 0.71 | 0.55 |
| 6 | 0.019 | 2.6 | 1.8 |
| 7 | 0.077 | 0.68 | 4.4 |
| 8 | 0.01 | 1.7 | 1 |
| 9 | 0.089 | NT | NT |
| 10 | 0.012 | NT | NT |
| 11 | 0.011 | 1.6 | 0.89 |
| 12 | 0.014 | NT | NT |
| 13 | 0.034 | NT | NT |
| 14 | 0.024 | 0.61 | 1.8 |
| 15 | 0.22 | NT | NT |
| 16 | 0.014 | NT | NT |
| 17 | 0.04 | NT | NT |
| 18 | 0.062 | NT | NT |
| 19 | 0.38 | NT | NT |
| 20 | 0.023 | 8 | 1.2 |
| 21 | 0.13 | NT | NT |
| 22 | 0.18 | NT | NT |
| 23 | 0.023 | 0.87 | 0.45 |
| 24 | 0.078 | 1.5 | 6.4 |
| 25 | 0.12 | NT | NT |
| 26 | 5 | NT | NT |
| 27 | 1 | NT | NT |
| 28 | 0.0055 | NT | NT |
| 29 | 0.28 | NT | NT |
| 30 | 1.8 | NT | NT |

From the above results, it was confirmed that the example compounds of the present invention have an agonistic activity against the human MC$_4$ receptor. It was also confirmed that among the example compounds of the present invention, in the example compounds evaluated regarding the human MC$_1$ and MC$_3$ receptors, the EC$_{50}$ values for the human MC$_1$ and MC$_3$ receptors are at higher concentrations than the EC$_{50}$ values for the human MC$_4$ receptor, and the compounds selectively act on the MC$_4$ receptor.

Test Example 2: Test for Evaluating Rat MC$_4$ Receptor Activation, Using Cells Expressing Rat MC$_4$ Receptor Experiment Method (1) Construction of Rat MC$_4$ Receptor-Expressing Vector A rat MC$_4$ receptor gene (GenBank Accession No.: NM_013099.3) was introduced into an expression vector pcDNA™ 3.1N/V5-His TOPO (registered trademark) (Thermo Fisher Scientific Inc.).

(2) Construction of Cells Transiently Expressing Rat MC$_4$ Receptor

An expression vector for a rat MC$_4$ receptor was introduced into FreeStyle™ 293-F cells (Thermo Fisher Scientific Inc.). For the introduction, electroporation was employed. That is, 1×10$^7$ FreeStyle™ 293-F cells were suspended in 80 μL of an electroporation buffer (Thermo Fisher Scientific Inc.), and 20 μg of the expression vector was added thereto. The resultant was put into a cuvette (OC-100 Processing Assembly, MaxCyte, Inc.) and electroporated with MaxCyte STX (registered trademark) (MaxCyte, Inc.). The cells were cultured for a day, suspended in a Cell Banker (registered trademark) 1 (TAKARA BIO INC. or JUJI FIELD Inc.), and stored frozen until they were used.

(3) Measurement of Amount of cAMP Production

Measurement was carried out in accordance with the attached instructions, using a LANCE (registered trademark) Ultra cAMP Kit (PerkinElmer, Inc.). That is, after dissolution in DMSO, the test compound (a final concentration of 1 pM to 30 μM) diluted with an assay buffer (Hank's balanced salt solution, 5 mM HEPES, 0.5 mM IBMX, 0.1% bovine serum albumin, pH 7.4), or α-MSH (Bachem Inc., a final concentration of 1 pM to 30 μM) was added to OptiPlate-384 (PerkinElmer, Inc.). Furthermore, the suspension of the cells transiently expressing the rat MC receptor that was prepared using the assay buffer was added thereto at 1,000 cells/well, and then left to stand at room temperature for about 1 hour. Thereafter, an Eu-cAMP tracer solution and an ULight™-anti-cAMP solution were added thereto, and the resulting solution was left to stand at room temperature for about 1 hour. The amount of cAMP was calculated using EnVision (registered trademark) (PerkinElmer Inc).

For the agonistic activity, an efficacy (EC$_{50}$ (μM)) was calculated by a non-linear regression method with a Sigmoid-Emax model, by defining the maximum reaction using α-MSH as 100% and the reaction using a vehicle alone as 0%, respectively.

The EC$_{50}$ values of some example compounds of the present invention are shown in Table 2. Ex represents the Example No. of the test compound.

TABLE 2

| Ex | EC$_{50}$ (μM) |
|---|---|
| 4 | 0.002 |
| 5 | 0.0033 |
| 6 | 0.016 |
| 7 | 0.015 |
| 8 | 0.0047 |
| 11 | 0.01 |
| 14 | 0.0088 |
| 20 | 0.0076 |
| 23 | 0.0048 |
| 24 | 0.046 |

From the above results, it was confirmed that the example compounds of the present invention have an agonistic activity against the rat MC$_4$ receptor.

Test Example 3: Effect on Rat Urethral Pressure

Experiment Method

The present Test Example was performed by partially modifying the technique reported as a testing system for evaluating a urethral resistance-reducing action (European Journal of Pharmacology, 679, 127-131 (2012)). Male Wistar rats (Charles River Laboratories Japan, Inc.) were anesthetized with urethane (1.2 g/kg ip), and immobilized in a supine position. The midline incision was performed in the lower abdominal portion such that the bladder was exposed. The bladder apex was incised, and from the incision site, a microchip pressure transducer catheter (3.5 Fr, Millar, Inc) was inserted and implanted into the inside of the urethra. In addition, a cannula for drug administration was implanted into the femoral vein. After the urethral pressure was stabilized, phenylephrine hydrochloride (Sigma-Aldrich Co. LLC., 30 μg/kg) was intravenously administered to induce an increase in the urethral pressure. At an interval of about 30 minutes, the above operation was repeated twice or more so as to confirm the stability of the phenylephrine hydrochloride-induced urethral pressure increasing reaction. Then, a test compound (dissolved in 20% dimethyl acetamide, 10% Cremophor (registered trademark), and 70% physiological saline) was intravenously administered, and after 5 minutes, phenylephrine hydrochloride was administered. The procedure of the administration of the test compound and the administration of phenylephrine hydrochloride was repeated at an interval of about 30 minutes, and 3 to 5 doses of the test compound was evaluated (the test compound was administered at increasing doses). The obtained data was introduced into a personal computer through PowerLab (registered trademark) (ADInstruments, Inc.) and analyzed using LabChart (registered trademark) (ADInstruments, Inc.). For the evaluation, the value (AUC value, mmHg-s) of the area under the urethral pressure for one minute before and after administration of phenylephrine hydrochloride was determined to calculate the difference ($\Delta$AUC value) between the AUC value before the administration of phenylephrine hydrochloride and the AUC value after the administration of phenylephrine hydrochloride. The $\Delta$AUC value obtained before administering the test compound was regarded as being 100%, and based on this, the ratio (reaction rate) of the $\Delta$AUC value of the test compound at each dose was calculated. The dose at which the obtained reaction rate became 60% (40% as an inhibition rate) was defined as $ID_{40}$, and the $ID_{40}$ values of the test compounds were calculated by non-linear regression.

The $ID_{40}$ values of some example compounds of the present invention are shown in Table 3. Ex represents the Example No. of the test compound.

TABLE 3

| Ex | $ID_{40}$ (g/kg) |
|---|---|
| 3 | 0.0089 |
| 4 | 0.011 |
| 5 | 0.025 |
| 6 | 0.046 |
| 8 | 0.015 |
| 11 | 0.028 |
| 14 | 0.071 |
| 16 | 0.011 |
| 20 | 0.04 |

From the above results, it was found that the example compounds of the present invention have inhibitory effect on phenylephrine-induced urethral pressure increase.

Test Example 4: Effect on Drug-Induced Voiding Dysfunction Model Rat

Experiment Method

Male Sprague Dawley (SD) rats (Japan SLC, Inc.) were anesthetized with isoflurane and a cannula was placed in the bladder, the stomach, and the jugular vein. Then, the rats were awakened in a Baellman cage (Natsume Seisakusho Co., Ltd.). After a post-operative stabilization period, physiological saline was continuously infused into the bladder by an infusion pump (Terumo Corporation, product number: TE-331 S, STC-528) to induce voiding. Infusion of the physiological saline was stopped as soon as the voiding began, and the amount of the voided urine was measured using an electronic top-loading balance installed under the Ballman cage. After voiding ended, the residual urine was collected by gravity through the cannula implanted into the bladder and weighed, and the weight was taken as the amount of the residual urine. Furthermore, the intravesical pressure was measured by a pressure transducer (Nihon Kohden Corporation, product numbers: DX-100) through the bladder cannula. The test compound or the vehicle was administered into the stomach, and atropine sulfate (Sigma-Aldrich Co. LLC., 0.01 mg/kg) as an anticholinergic drug and midodrine hydrochloride (Sigma-Aldrich Co. LLC., 0.3 mg/kg) as an $\alpha$ adrenergic receptor agonist were intravenously administered to induce voiding dysfunction. The voiding efficiency (=[voided amount/(voided amount+ amount of residual urine)]×100) and the amount of the residual urine before and after the administration of the test compound or the vehicle were measured, and the amount changed was evaluated. The value obtained by the administration of the vehicle and the value obtained by the administration of the test compound were compared in a Dunnett's multiple comparison test with a statistically significant difference (P<0.05), and the minimum dose at which the inhibitory action on a decrease in voiding efficiency or on an increase of the amount of residual urine observed was defined as a minimum effective dose (4 rats per group).

The minimum effective doses of some example compounds of the present invention are shown in Table 4. Ex represents the Example No. of the test compound. MED represents a minimum effective dose.

TABLE 4

| Ex | MED (mg/kg ig) |
|---|---|
| 4 | 0.01 |
| 5 | 0.01 |
| 6 | 0.03 |
| 8 | 0.01 |
| 11 | 0.03 |

From the above results, it was found that the example compounds of the present invention have inhibitory effect on a decrease in the voiding efficiency or on an increase of the amount of residual urine.

Test Example 5: Rat Erection-Inducing Action

Experiment Method

Male SD rats (Charles River Laboratories Japan, Inc.) were used. Some test compounds (10 mg/kg) or vehicles (20% dimethyl acetamide, 10% Cremophor (registered trademark), and 70% physiological saline) were intravenously administered through the caudal vein. After the administration, the rats were placed in a plastic transparent observation cages, and whether or not penile erection occurs was measured for up to 1 hour after the administration. As a result of using some of the example compound of the present invention as a test compound, it was confirmed that the example compound does not have an erection-inducing effect which is an effect on central nervous system.

Test Example 6: Cytochrome P450 3A4 Inhibition Test (1) Inhibition Test I (Calculation of Remaining Activity I)

A test compound, and human liver microsomes (0.1 mg protein/mL) were incubated in a 100 mmol/L phosphate buffer (pH 7.4) containing 0.1 mmol/L EDTA and 1 mmol/L NADPH with midazolam as a substrate for 20 minutes at 37° C. Then, an aqueous solution containing acetonitrile was added thereto so as to stop the reaction. Thereafter, the sample was analyzed with LC-MS/MS, and Remaining Activity I was calculated using the following equation.

$$\text{Remaining Activity } I(\%) = A_{i,j}/A_{0,j} \times 100$$

$A_{i,j}$: The amount of produced metabolite after the reaction in the presence of a test compound at a known concentration in Inhibition Test I $A_{0,I}$: The amount of produced metabolite after the reaction in the absence of a test compound in Inhibition Test I (2) Inhibition Test II (Calculation of Remaining Activity II)

A test compound and human liver microsomes (0.1 mg protein/mL) were incubated in a 100 mmol/L phosphate buffer (pH 7.4) containing 0.1 mmol/L EDTA and 1 mmol/L NADPH for a defined period of time at 37° C., followed by incubation with midazolam as a substrate for a defined period of time at 37° C. Then, an aqueous solution containing acetonitrile was added thereto so as to stop the reaction. Thereafter, the sample was analyzed with LC-MS/MS, and Remaining Activity II was calculated using the following equation.

Remaining Activity $II(\%)=(A_{i,II}/A_{0,II})/($Remaining Activity $I(\%)/100)\times 100$ $A_{i,II}$: The amount of produced metabolite after the reaction in the presence of a test compound at a known concentration in Inhibition Test II $A_{0,II}$: The amount of produced metabolite after the reaction in the absence of a test compound in Inhibition Test II Test Example 7: Test for Metabolic Stability in Human Liver Microsomes A test compound and human liver microsomes (0.2 mg protein/mL) were incubated in a 100 mmol/L phosphate buffer (pH 7.4) containing 0.1 mmol/L EDTA and 1 mmol/L NADPH for a defined period of time at 37° C. Then, an aqueous solution containing acetonitrile was added thereto so as to stop the reaction. Thereafter, the sample was analyzed with LC-MS/MS, and in vitro clearance was calculated by an integration plot.

As is evident from the results of each of the above tests, it was confirmed that the compound of the formula (I) has a human $MC_4$ receptor-selective agonistic activity, and that the compound has inhibitory effect on phenylephrine-induced urethral pressure increase in vivo. Furthermore, it was confirmed that in a rat model with a voiding dysfunction, the compound has an inhibitory effect on a decrease in voiding efficiency and an increase of the amount of residual urine. In addition, it was confirmed that some of the compounds of the formula (I) do not exhibit an erection-inducing effect which is an effect on the central nervous system. Accordingly, the compound of the formula (I) is expected to be useful for preventing or treating bladder and/or urinary tract diseases, particularly, voiding dysfunctions in bladder and/or urinary tract diseases. For example, the compound of the formula (I) is expected to be useful for preventing or treating voiding dysfunctions in underactive bladder, hypotonic bladder, acontractile bladder, detrusor underactivity, neurogenic bladder, urethral relaxation failure, detrusor-external urethral sphincter dyssynergia, overactive bladder, urinary frequency, nocturia, urinary incontinence, benign prostatic hyperplasia, interstitial cystitis, chronic prostatitis, urethral calculus, or the like. Particularly, the compound of the formula (I) is expected to be useful for preventing or treating voiding dysfunctions in underactive bladder, hypotonic bladder, acontractile bladder, detrusor underactivity, neurogenic bladder, urethral relaxation failure, detrusor-external urethral sphincter dyssynergia, and benign prostatic hyperplasia.

A pharmaceutical composition containing one kind or two or more kinds of the compound of the formula (I) or a salt thereof as an active ingredient can be prepared using excipients generally used in the related art, that is, excipients for pharmaceutical preparation, carriers for pharmaceutical preparation, and the like according to generally used methods.

Administration can be accomplished either by oral administration by using tablets, pills, capsules, granules, powders, solutions, and the like or by parenteral administration, such as injections such as intraarticular, intravenous, and intramuscular injections, suppositories, eye drops, eye ointments, transdermal solutions, ointments, transdermal patches, transmucosal solutions, transmucosal patches, inhalers, and the like.

Solid compositions for oral, administration are used in the form of tablets, powders, granules, or the like. In such solid compositions, one kind or two or more kinds of active ingredients are mixed with at least one inactive excipient. According to the conventional methods, the compositions may contain inactive additives such as lubricants, disintegrating agents, stabilizers, and solubilization assisting agents. If necessary, tablets or pills may be coated with sugar or films of gastric- or enteric-soluble substances.

Liquid compositions for oral administration include pharmaceutically acceptable emulsions, solutions, suspensions, syrups, elixirs, or the like and also include generally used inert diluents such as purified water or ethanol. In addition to the inert diluent, the liquid compositions may also contain auxiliary agents such as solubilization assisting agents, moistening agents, and suspending agents, sweeteners, flavors, aromatics, or antiseptics.

Injections for parenteral administration include sterile aqueous or non-aqueous solutions, suspensions, or emulsions. Aqueous solvents include, for example, distilled water for injection or physiological saline. Examples of the non-aqueous solvents include alcohols such as ethanol. These compositions may further contain tonicity agents, antiseptics, moistening agents, emulsifying agents, dispersing agents, stabilizers, or solubilization assisting agents. These are sterilized by filtration through bacteria retaining filter, mixing with a bactericide, or irradiation, for example. Furthermore, these can also be used by preparing sterile solid compositions, and dissolving or suspending the solid compositions in sterile water or sterile solvents for injection before use.

Agents for external use include ointments, plasters, creams, gels, poultices, sprays, lotions, eye drops, eye ointments, and the like. The agents contain generally used ointment bases, lotion bases, aqueous or non-aqueous solutions, suspensions, emulsions, and the like.

As transmucosal agents such as inhalers or transnasal agents, those in the form of a solid, liquid, or semi-solid state are used, and can be prepared according to the methods known in the related art. For example, known excipients, pH adjusting agents, antiseptics, surfactants, lubricants, stabilizers, or thickening agents may be appropriately added thereto. For administering the transmucosal agents, appropriate devices for inhalation or blowing can be used. For example, by using a known device or spray such as a metered-dose administration inhalation device, the compound may be administered alone, administered as powder of a formulated mixture, or administered as a solution or suspension in combination with pharmaceutically acceptable carriers. Dry powder inhalers or the like may be used for single dosing or multiple dosing, and dry powder or powder-containing capsules may be used. Alternatively, these may be a pressurized aerosol spray which uses appropriate ejection agents such as a suitable gas including chlorofluoroalkane, carbon dioxide, and the like.

For oral administration, the daily dose is generally about 0.001 mg/kg to 100 mg/kg, preferably 0.1 mg/kg to 30 mg/kg, and more preferably 0.1 mg/kg to 10 mg/kg, per body weight, and the composition is administered at the above dose in one portion or in 2 to 4 divided portions. For intravenous administration, a suitable daily dose is about 0.0001 mg/kg to 10 mg/kg per body weight, and the composition is administered once a day or plural times a day. In addition, a transmucosal agent is administered at a dose from about 0.001 mg/kg to 100 mg/kg per body weight, once a day or plural times a day. The doses are appropriately determined according to the individual in consideration of the symptoms, age, gender, and the like.

Although varying depending on administration routes, formulations, administration sites, or the types of excipients or additives, the pharmaceutical composition of the present invention contains 0.01% by weight to 100% by weight, and in a certain embodiment, 0.01% by weight to 50% by weight of one or more kinds of the compound of the formula (I) or a salt thereof, which is an active ingredient.

The compound of the formula (I) can be used in combination with various agents for treating or preventing the diseases for which the compound of the formula (I) is considered to be effective. The combined preparation may be administered simultaneously, or separately and continuously, or at a desired time interval. The preparations administered simultaneously may be a combination preparation or may be prepared individually.

EXAMPLES

Hereinafter, the method for preparing the compound of the formula (I) will be more specifically described with reference to Examples, but the present invention is not limited to the following compounds described below. The production processes for the starting compounds will be described in Preparation Examples. The method for preparing the compound of the formula (I) is not limited to the preparation methods in specific Examples shown below, and the compound of the formula (I) can be prepared according to a combination of these preparation methods or methods apparent to a person skilled in the art.

In the tables shown below, the following abbreviations are used in some cases.

PEx: preparation example No., Ex: example No., PSyn: method for preparing example (the number in the column of PSyn indicates that the compound is prepared using the corresponding starting material by the same method as used for preparing the compound with the number as the preparation example compound No; for example, a compound with 3 in the column of PSyn means that the compound is prepared by the same method as that used for preparing the compound of Preparation Example 3), syn: method for preparing example compound (The number in the column of Syn indicates that the compound is prepared using the corresponding starting material by the same method as that used for preparing the compound with the number as the example compound No; for example, a compound with 1 in the column of Syn means that the compound is prepared by the same method as that used for preparing the compound of Example 1), Str: chemical structural formula, DAT: physicochemical data, Me: methyl ESI+: m/z values in mass spectroscopy (ionization ESI, representing [M+H]$^+$ unless specified), ESI−: m/z values in mass spectroscopy (ionization ESI, representing [M−H]$^-$ unless specified), APCI/ESI+: (ionization APCI/ESI; APCI/ESI means that APCI and ESI are performed simultaneously; representing [M+H]$^+$ unless specified), EI: m/z values in mass spectroscopy (ionization EI, representing [M]$^+$ unless specified), CI+: m/z values in mass spectroscopy (ionization CI, representing [M+H]$^+$ unless specified)

NMR1: δ value (ppm) of signals in $^1$H-NMR in pyridine-d5, NMR2: δ value (ppm) of signals in $^1$H-NMR in CDCl$_3$, s: singlet, m: multiplet Unless otherwise specified, the compound represents an optical isomer having an absolute steric configuration described in the chemical structural formula. The compound marked with "#" represents an optical isomer which has the absolute steric configuration described in the chemical structural formula and in which the steric configuration in the asymmetric carbon moiety with no description of the steric configuration is single but undetermined. The compound marked with "*" indicates the compound has the denoted steric configuration, in which the steric form in the asymmetric carbon moiety with no description of the steric configuration is a mixture of R and S isomers.

In a case where HCl is shown in a chemical structural formula, it means that the compound is a monohydrochloride. In a case where 2HCl is shown in a chemical structural formula, it means that the compound is a dihydrochloride.

For the sake of convenience, the concentration mol/l is represented by M. For example, a 1 M aqueous sodium hydroxide solution means a 1 mol/l aqueous sodium hydroxide solution.

Preparation Example 1

Under an argon atmosphere, N,N-diisopropylethylamine (5 mL) and O-(7-aza-1H-benzotriazol-1-yl)-N,N,N',N'-tetramethyluronium hexafluorophosphate (5.5 g) were added to a mixture of (3 S,4R)-1-tert-butyl-4-(2,4-difluorophenyl)pyrrolidine-3-carboxylate (4 g), (2R,5S)-2,5-dimethylpiperazine-1-carboxylic acid tert-butyl ester monohydrochloride (3 g), and N,N-dimethylformamide (30 mL) with ice cooling, followed by stirring overnight at room temperature. The reaction mixture was ice-cooled, and a saturated aqueous sodium hydrogen carbonate solution was added thereto, followed by stirring. Water was added to the reaction mixture, and then extraction was performed using ethyl acetate. The organic layer was washed with a saturated aqueous sodium hydrogen carbonate solution, water, and brine. The organic layer was dried over anhydrous sodium sulfate, the insoluble material was separated by filtration, and the filtrate was concentrated under reduced pressure. The obtained residue was purified by silica gel column chromatography (chloroform:methanol=100:0 to 80:20), thereby obtaining (2R,5S)-4-{[(3 S,4R)-1-tert-butyl-4-(2,4-difluorophenyl)pyrrolidin-3-yl]carbonyl}-2,5-dimethylpiperazine-1-carboxylic acid tert-butyl ester (5.80 g) as a solid.

Preparation Example 10

Hydrogen chloride (4 M dioxane solution, 30 mL) was added to a mixture of (2R,5S)-4-{[(3 S,4R)-1-tert-butyl-4-(2,4-difluorophenyl)pyrrolidin-3-yl]carbonyl}-2,5-dimethylpiperazine-1-carboxylic acid tert-butyl ester (5.80 g) and ethanol (50 mL) with ice cooling, followed by stirring for 14 hours at room temperature. The solvent was evaporated under reduced pressure, thereby obtaining [(3S,4R)-1-tert-butyl-4-(2,4-difluorophenyl)pyrrolidine-3-yl][(2S,5R)-2,5-dimethylpiperazin-1-yl]methanone dihydrochloride (5.28 g) as a solid.

Preparation Example 18

Under an argon atmosphere, N,N-diisopropylethylamine (6.2 mL), N-(tert-butoxycarbonyl)-4-methyl-L-leucine (3 g), and O-(7-aza-1H-benzotriazol-1-yl)-N,N,N',N'-tetramethyluronium hexafluorophosphate (4.8 g) were added to a mixture of [(3S,4R)-1-tert-butyl-4-(2,4-difluorophenyl)pyrrolidine-3-yl][(2S,5R)-2,5-dimethylpiperazin-1-yl]methanone dihydrochloride (4.68 g) and N,N-dimethylformamide (50 mL) with ice cooling, followed by stirring for 2 hours at room temperature. The reaction mixture was ice-cooled, and a saturated aqueous sodium hydrogen carbonate solution was added thereto, followed by stirring. Water was added to the reaction mixture, and then extraction was performed using ethyl acetate. The organic layer was washed with a saturated aqueous sodium hydrogen carbonate solution, water, and brine. After the organic layer was dried over anhydrous sodium sulfate, the insoluble material was separated by filtration, and the filtrate was concentrated under reduced pressure. The obtained residue was purified by silica gel column chromatography (chloroform:methanol=100:0 to 80:20), thereby obtaining {(2S)-1-[(2R,5S)-4-([(3S,4R)-1-tert-butyl-4-(2,4-difluorophenyl)pyrrolidin-3-yl]carbonyl-2,5-dimethylpiperazin-1-yl]-4,4-dimethyl-1-oxopentan-2-yl}carbamic acid tert-butyl ester (6.30 g) as a solid.

Preparation Example 33

Hydrogen chloride (4 M dioxane solution, 25 mL) was added to a mixture of {(2S)-1-[(2R,5S)-4-{[(3 S,4R)-1-tert-butyl-4-(2,4-difluorophenyl)pyrrolidin-3-yl]carbonyl}-2,5-dimethylpiperazin-1-yl]-4,4-dimethyl-1-oxopentan-2-yl}carbamic acid tert-butyl ester (5.80 g) and ethanol (60 mL) with ice cooling. The reaction mixture was stirred for 14 hours at room temperature, and then hydrogen chloride (4 M dioxane solution, 10 mL) was added thereto at room temperature. The reaction mixture was stirred for 5 hours at room temperature, and then the solvent was evaporated under reduced pressure, thereby obtaining (2S)-2-amino-1-[(2R,5S)-4-{[(3 S,4R)-1-tert-butyl-4-(2,4-difluorophenyl)pyrrolidin-3-yl]carbonyl}-2,5-dimethylpiperazin-1-yl]-4,4-dimethylpentan-1-one dihydrochloride (5.35 g) as a solid.

Preparation Example 45

Hydrogen chloride (4 M ethyl acetate solution, 27 mL) was added to a mixture of (3S)-4-{[(3 S,4R)-1-tert-butyl-4-(2,4-difluorophenyl)pyrrolidin-3-yl]carbonyl}-3-methylpiperazine-1-carboxylic acid tert-butyl ester (10.22 g) and ethanol (100 mL) with ice cooling, followed by stirring overnight at room temperature. The reaction solution was concentrated under reduced pressure, a saturated aqueous sodium hydrogen carbonate solution was added to the obtained residue, and then extraction was performed using chloroform. The organic layer was dried over anhydrous sodium sulfate, and the insoluble material was separated by filtration. The filtrate was concentrated under reduced pressure, thereby obtaining [(3S,4R)-1-tert-butyl-4-(2,4-difluorophenyl)pyrrolidin-3-yl][(2S)-2-methylpiperazin-1-yl]methanone (7.65 g) as an oil.

Preparation Example 47

Acetic anhydride (0.9 mL) was added to a suspension of 3-cyclopentyl-L-alanine (1 g) and a 5% aqueous sodium hydrogen carbonate solution (20 mL) with ice cooling, followed by stirring overnight at room temperature. 1 M hydrochloric acid was added thereto so as to adjust the pH thereof to be 1 to 2, followed by stirring for 30 minutes. The precipitated solid was collected by filtration, washed with water, and dried for 3 hours at 40° C. under reduced pressure. The obtained solid was washed with diisopropyl ether, collected by filtration, and dried, thereby obtaining N-acetyl-3-cyclopentyl-L-alanine (597 mg) as a solid.

Preparation Example 49

Hydrogen chloride (4 M dioxane solution, 15 mL) was added to a mixture of [(2S)-1-[(3S)-4-{[(3S,4R)-1-tert-butyl-4-(2,4-difluorophenyl)pyrrolidin-3-yl]carbonyl}-3-methylpiperazin-1-yl]-3-(2-chlorophenyl)-1-oxopropan-2-yl]carbamic acid tert-butyl ester (4.03 g) and ethanol (60 mL) with ice cooling, followed by stirring for 24 hours at room temperature. The solvent was evaporated under reduced pressure, a saturated aqueous sodium hydrogen carbonate solution was added to the residue, and extraction was performed using chloroform. The organic layer was dried over anhydrous sodium sulfate, the insoluble material was separated by filtration, and the filtrate was concentrated under reduced pressure. The obtained residue was purified by silica gel column chromatography (chloforom:methanol=100:0 to 80:20), thereby obtaining (2S)-2-amino-1-[(3S)-4-{[(3 S,4R)-1-tert-butyl-4-(2,4-difluorophenyl)pyrrolidin-3-yl]carbonyl}-3-methylpiperazin-1-yl]-3-(2-chlorophenyl)propan-1-one (2.51 g) as a solid.

Preparation Example 51

A mixture of (4,4-dimethylcyclohex-1-en-1-yl)methanol (5.18 g) and dichloromethane (60 mL) was ice-cooled, and phosphorus tribromide (3.80 mL) was added thereto. The reaction mixture was heated to room temperature and then stirred for 3 hours. A saturated aqueous sodium hydrogen carbonate solution was added to the reaction mixture, and extraction was performed using chloroform. The organic layer was washed with brine and dried over anhydrous magnesium sulfate. The insoluble material was separated by filtration, and the filtrate was concentrated under reduced pressure. The obtained residue was purified by silica gel column chromatography (hexane), thereby obtaining 1-(bromomethyl)-4,4-dimethylcyclohexene (5.60 g) as an oil.

Preparation Example 52 tert-Butyl N-(diphenylmethylidene)glycinate (4.80 g) and (R)-4,4-dibutyl-2,6-bis(3,4,5-trifluorophenyl)-4,5-dihydro-3H-dinaphtho[2,1-c: 1',2'-e]azepinium bromide (122 mg) were added to a mixture of 1-(bromomethyl)-4,4-dimethylcyclohexene (5.60 g) and toluene (54 mL). After the reaction mixture was ice-cooled, an aqueous solution (54 mL) of potassium hydroxide (27 g) was added thereto, followed by stirring for 15 hours with ice cooling. Water was added to the reaction mixture, and extraction was performed using diethyl ether. The organic layer was washed with brine and dried over anhydrous magnesium sulfate. The insoluble material was separated by filtration, and the filtrate was concentrated under reduced pressure. The obtained residue was purified by silica gel column chromatography (hexane: ethyl acetate=100:0 to 93:7), thereby obtaining tert-butyl 3-(4,4-dimethylcyclohex-1-en-1-yl)-N-(diphenylmethylidene)-L-alaninate (5.47 g) as an oil.

Preparation Example 53

An aqueous solution (33 mL) of citric acid (12.5 g) was added to a mixture of tert-butyl 3-(4,4-dimethylcyclohex-1-en-1-yl)-N-(diphenylmethylidene)-L-alaninate (5.47 g) and tetrahydrofuran (66 mL), followed by stirring for 3 hours at room temperature. Diisopropyl ether was added to the reaction mixture, and the aqueous layer was separated. Potassium carbonate was added to the aqueous layer, extraction was performed using chloroform, and the organic layer was dried over anhydrous magnesium sulfate. The insoluble material was separated by filtration, and the filtrate was concentrated under reduced pressure, thereby obtaining 3-(4,4-dimethylcyclohex-1-en-1-yl)-L-alanine tert-butyl ester (2.78 g) as an oil.

Preparation Example 54

Under a nitrogen atmosphere, 10% palladium hydroxide on carbon (540 mg) was added to a mixture of 3-(4,4-dimethylcyclohex-1-en-1-yl)-L-alanine tert-butyl ester (2.68 g) and ethanol (53.0 mL) at room temperature. The reaction mixture was stirred for 5 hours under a hydrogen atmosphere at room temperature. Celite was added to the reaction mixture, followed by stirring for 15 minutes at room temperature. The reaction mixture was filtered through celite, and the filtrate was concentrated under reduced pressure. Under a nitrogen atmosphere, ethanol (53.0 mL) and 10% palladium hydroxide on carbon (540 mg) were added to the residue at room temperature. Under a hydrogen atmosphere at 3 atm, the reaction mixture was stirred for 15 hours at room temperature. The reaction mixture was filtered through celite, and the filtrate was concentrated under reduced pressure, thereby obtaining 3-(4,4-dimethylcyclohexyl)-L-alanine tert-butyl ester monohydrochloride (2.67 g) as a solid.

Preparation Example 56

N,N-diisopropylethylamine (0.352 mL) and acetyl chloride (0.088 mL) were added to a mixture of 3-(4,4-dimethylcyclohexyl)-L-alanine tert-butyl ester monohydrochloride (300 mg) and dichloromethane (3 mL), followed by stirring for 1 hour at room temperature. A saturated aqueous sodium hydrogen carbonate solution was added to the reaction mixture, and extraction was performed using ethyl acetate. The organic layer was washed with a 5% aqueous citric acid solution and with brine, and dried over anhydrous magnesium sulfate. The insoluble material was separated by filtration, and the filtrate was concentrated under reduced pressure, thereby obtaining N-acetyl-3-(4,4-dimethylcyclohexyl)-L-alanine tert-butyl ester (360 mg) as a oil.

Preparation Example 60

Hydrogen chloride (4 M dioxane solution, 1.2 mL) was added to a mixture of N-acetyl-3-(4,4-dimethylcyclohexyl)-L-alanine tert-butyl ester (360 mg) and ethanol (3.6 mL), followed by stirring for 2 hours at room temperature. Hydrogen chloride (4 M dioxane solution, 3 mL) was added to the reaction mixture, followed by stirring for 1 day at room temperature. The reaction mixture was concentrated, thereby obtaining N-acetyl-3-(4,4-dimethylcyclohexyl)-L-alanine (292 mg) as a solid.

Preparation Example 61

Zinc (4.0 g) was put into a reaction container and dried by heating with a heating gun under reduced pressure. N,N-dimethylformamide (5 mL) and iodine (96 mg) were added to the reaction container, followed by stirring for 3 minutes at room temperature. Iodine (96 mg) was added to the reaction mixture, and then a N,N-diemethylformamide (10 mL) solution of N-(tert-butoxycarbonyl)-3-iodo-L-alanine methyl ester (5.0 g) was added thereto, followed by stirring for 15 minutes at room temperature. To the reaction mixture were added tris(dibenzylideneacetone)dipalladium (0) (696 mg), 2-dicyclohexylphosphino-2',6'-dimethoxyphenyl (624 mg), and trifluoromethane sulfonic acid 4,4-difluorocyclohex-1-en-1-yl ester (4.5 g) were added, followed by stirring for 1 day at 60° C. A saturated aqueous sodium hydrogen carbonate solution was added to the reaction mixture, and the resulting mixture was filtered through celite. The aqueous layer was extracted using ethyl acetate, and the organic layer was washed with water. The organic layer was washed with brine and dried over anhydrous magnesium sulfate. The insoluble material was separated by filtration, and the filtrate was concentrated under reduced pressure. The obtained residue was purified by silica gel column chromatography (hexane:ethyl acetate=90:10 to 75:25), thereby obtaining N-(tert-butoxycarbonyl)-3-(4,4-difluorocyclohex-1-en-1-yl)-L-alanine methyl ester (4.73 g) as an oil.

Preparation Example 62

Lithium hydroxide monohydrate (89 mg) was added to a mixture of N-acetyl-3-(4,4-difluorocyclohexyl)-L-alanine methyl ester (223 mg), tetrahydrofuran (4.5 mL), and water (1.2 mL), followed by stirring for 1 day at room temperature. 1 M hydrochloric acid was added to the reaction mixture, and extraction was performed using ethyl acetate. The organic layer was washed with brine and dried over anhydrous magnesium sulfate. The insoluble material was separated by filtration, and the filtrate was concentrated under reduced pressure, thereby obtaining N-acetyl-3-(4,4-difluorocyclohexyl)-L-alanine (111 mg) as a solid.

Preparation Example 63

N,N-dimethylformamide (22 μL) was added to a dichloromethane (15 mL) suspension of 4-fluorocinnamic acid (1.00 g) at room temperature. Under an argon atmosphere, a dichloromethane (7 mL) solution of oxalyl chloride (1 mL) was added dropwise to the ice-cooled reaction mixture for about 10 minutes. The reaction mixture was warmed to room temperature and stirred overnight. The reaction mixture was concentrated under reduced pressure, and the obtained residue was dissolved in dichloromethane (7 mL). Under an argon atmosphere, the solution was added dropwise to a dichloromethane (15 mL) suspension of ice-cooled (4S)-4-benzyl-1,3-oxazolidin-2-one (1.1 g), lithium chloride (1.29 g), and triethylamine (4.3 mL) for about 10 minutes. The reaction mixture was warmed to room temperature and stirred overnight. A 5% aqueous citric acid solution was added to the reaction mixture, and an aqueous layer and an organic layer were separated. The aqueous layer was extracted using chloroform, and the organic layers were combined and washed with brine, followed by drying over anhydrous sodium sulfate. Then, the insoluble material was separated by filtration, and the filtrate was concentrated under reduced pressure. The obtained residue was purified by silica gel column chromatography (chloroform:methanol=100:0 to 95:5), thereby obtaining (4S)-4-benzyl-3-[(2E)-3-(4-fluorophenyl)prop-2-enoyl]-1,3-oxazolidin-2-one (1.42 g) as a solid.

Preparation Example 65

A mixture of diethyl {2-[(4S)-4-benzyl-2-oxo-1,3-oxazolidin-3-yl]-2-oxoethyl}phosphate (8.55 g) and tetrahydrofuran (100 mL) was ice-cooled, and then sodium hydride (55% oil dispersion, 1.2 g) was added thereto, followed by stirring for 10 minutes. 4-Chloro-3,5-difluorobenzaldehyde (4.64 g) was added thereto, and then the mixture was warmed to room temperature. The reaction mixture was stirred for 2 hours at room temperature, and then a saturated aqueous ammonium chloride solution was added thereto. The reaction mixture was subjected to extraction using ethyl acetate and washed with brine. The organic layer was dried over anhydrous magnesium sulfate, the insoluble material was separated by filtration, and the filtrate was concentrated under reduced pressure. The obtained residue was purified by silica gel column chromatography (chloroform:methanol=100:0 to 95:5), thereby obtaining (4S)-4-benzyl-3-[(2E)-3-(4-chloro-3,5-difluorophenyl)prop-2-enoyl]-1,3-oxazolidin-2-one (6.04 g) as a solid.

Preparation Example 66

N,N-diisopropylethylamine (1.20 mL) was added to a mixture ice-cooled diethyl {2-[(4S)-4-benzyl-2-oxo-1,3-oxazolidin-3-yl]-2-oxoethyl}phosphate (2.10 g), lithium chloride (315 mg), and acetonitrile (42.0 mL), followed by stirring for 10 minutes at the same temperature. To the reaction mixture was added 5-chloro-2-pyridine carboxaldehyde (840 mg), followed by warming to room temperature and stirring overnight. The reaction mixture was poured into water, followed by stirring for 1 hour at room temperature. The generated solid was collected by filtration and washed with water. The obtained solid was dried under reduced pressure at 60° C., thereby obtaining (4S)-4-benzyl-3-[(2E)-3-(5-chloropyridin-2-yl)prop-2-enoyl]-1,3-oxazolidin-2-one (1.65 g) as a solid.

Preparation Example 67

Trifluoroacetic acid (30 μL) was added to a mixture of (4S)-4-benzyl-3-[(2E)-3-(4-fluorophenyl)prop-2-enoyl]-1,3-oxazolidin-2-one (400 mg) and dichloromethane (4 mL) at room temperature, and then a dichloromethane (2 mL) solution of N-(methoxymethyl)-2-methyl-N-[(trimethylsilyl)methyl]propane-2-amine (350 mg) was added thereto, followed by stirring overnight. Trifluoroacetic acid (140 μL) was added to the reaction mixture at room temperature, and then a dichloromethane (1 mL) solution of N-(methoxymethyl)-2-methyl-N-[(trimethylsilyl)methyl]propane-2-amine (150 mg) was added thereto, followed by stirring for 3 days. Chloroform and a saturated aqueous sodium hydrogen carbonate solution were added to the reaction mixture, and an aqueous layer and an organic layer were separated. The aqueous layer was extracted using chloroform, and the organic layers were combined and dried over anhydrous sodium sulfate. Then, the insoluble material was separated by filtration, and the filtrate was concentrated under reduced pressure. The obtained residue was purified by silica gel column chromatography (chloroform:methanol=100:0 to 90:10), thereby obtaining (4S)-4-benzyl-3-{[1-tert-butyl-4-(4-fluorophenyl)pyrrolidin-3-yl]carbonyl}-1,3-oxazolidin-2-one (203 mg, a fraction eluted earlier, a single stereoisomer in which the absolute configuration of the 3-position and the 4-position of the pyrrolidine ring is undetermined) as a solid. Furthermore, a single isomer (110 mg, Preparation Example 67, a fraction eluted later) in which the steric configurations of the 3-position and the 4-position of pyrrolidine were different was obtained as a solid.

Preparation Example 71

Lithium hydroxide monohydrate (1.19 g) was added to a mixture of (4S)-4-benzyl-3-{[1-tert-butyl-4-(4-fluorophenyl)pyrrolidin-3-yl]carbonyl}-oxazolidin-2-one (6 g, Preparation Example 67, a fraction eluted later, a single stereoisomer in which the absolute configuration of the 3-position and the 4-position of the pyrrolidine ring is undetermined), tetrahydrofuran (90 mL), and water (30 mL) under ice-cooling, followed by stirring for 3 hours at room temperature. The reaction mixture was ice-cooled, and 1 M hydrochloric acid (28.3 mL) was added thereto. The reaction mixture was diluted with water, and ethyl acetate was added thereto so as to separate an aqueous layer and an organic layer. The organic layer was extracted using water, and the aqueous layers were combined and concentrated under reduced pressure. Azeotropic distillation was performed three times by using ethanol, thereby obtaining 1-tert-butyl-4-(4-fluorophenyl)pyrrolidine-3-carboxylic acid (5.74 g, a single stereoisomer in which the absolute configuration of the 3-position and the 4-position of the pyrrolidine ring is undetermined) as a solid.

Preparation Example 74

Under an argon atmosphere, potassium carbonate (5.11 g) and 4-tert-butylbenzenethiol (5 mL) were added to a mixture of N-[(2S)-4,4-dimethyl-1-{(3S)-3-methyl-4-[(2-nitrophenyl)sulfonyl]piperazin-1-yl}-oxopentan-2-yl]acetamide (8.41 g) and N,N-dimethylformamide (84 mL), followed by stirring for 3.5 hours. The reaction mixture was ice-cooled, water was added thereto, and extraction was performed using ethyl acetate. The organic layer was extracted using 1 M hydrochloric acid, and then potassium carbonate was added to the aqueous layer so as to basify the aqueous layer. The aqueous layer was extracted using chloroform. The aqueous layer was extracted using a mixed solvent of chloroform-methanol (5:1). The organic layers were combined and dried over anhydrous sodium sulfate. Then, the insoluble material was separated by filtration, and the filtrate was concentrated under reduced pressure. Azeotropic distillation was performed three times on the obtained residue by using toluene, thereby obtaining N-{(2S)-4,4-dimethyl-1-[(3S)-3-methylpiperazin-1-yl]-1-oxopentan-2-yl}acetamide (1.74 g) as a solid.

Preparation Example 75

Under a nitrogen atmosphere, a mixture of borane-N,N-diethylaniline complex (46.2 g), (S)-5,5-diphenyl-2-methyl-3,4-propano-1,3,2-oxaoxazaborolidine (1 M toluene solution, 5 mL), and tert-butylmethyl ether (250 mL) was heated to 35° C. Then, a solution of 2-chloro-1-(4-chloro-2-fluorophenyl)ethanone (51 g) in tert-butylmethyl ether (300 mL) was added dropwise thereto at 40° C. for 2 hours. After dropwise addition ended, the mixture was stirred overnight while being left to cool to room temperature. The reaction mixture was ice-cooled, and methanol (150 mL) was added dropwise thereto. Then, a mixture of concentrated hydrochloric acid (80 mL) and water (220 mL) was added dropwise thereto, followed by stirring for 1 hour with ice-cooling. The reaction mixture was extracted using tert-butylmethyl ether. The organic layers were combined, washed with brine, and dried over anhydrous magnesium sulfate. The insoluble material was separated by filtration, and the filtrate was concentrated under reduced pressure. Hexane (100 mL) was added to the obtained residue, and the mixture was stirred for 1 hour at room temperature and then for 1 hour with ice cooling. The generated solid was collected by filtration and washed with ice-cooled hexane. The obtained solid was dried under reduced pressure at room temperature, thereby obtaining (1S)-2-chloro-1-(4-chloro-2-fluorophenyl)ethanol (42.4 g) as a solid.

Preparation Example 76

A mixture of (1S)-2-chloro-1-(4-chloro-2-fluorophenyl) ethanol (8 g) and methanol (4 mL) was ice-cooled, and tetrahydro-2H-pyran-4-amine (20 mL) and sodium hydroxide (1.7 g) were added thereto. The reaction mixture was stirred at 60° C. overnight.

The reaction mixture was cooled to room temperature and then poured into water (320 mL), followed by stirring for 1 hour at room temperature. The generated solid was collected by filtration, and the obtained solid was dried at 50° C. under reduced pressure. The obtained solid was added to a mixed solution of hexane (160 mL) and diisopropyl ether (16 mL), and the mixture was stirred for 4 hours at 70° C., and then stirred overnight while being left to cool to room temperature. The solid was collected by filtration and dried under reduced pressure at 50° C., thereby obtaining (1S)-1-(4-chloro-2-fluorophenyl)-2-(tetrahydro-2H-pyran-4-ylamino) ethanol (7.90 g) as a solid.

Preparation Example 77

Under a nitrogen atmosphere, a mixture of (1S)-1-(4-chloro-2-fluorophenyl)-2-(tetrahydro-2H-pyran-4-ylamino) ethanol (7.9 g) and acrylonitrile (34 mL) was stirred for 47 hours at 70° C. The reaction mixture was cooled to room temperature and then concentrated under reduced pressure. The obtained residue was purified by silica gel column chromatography (hexane:ethyl acetate=6:4 to 0:10), thereby obtaining 3-{[(2S)-2-(4-chloro-2-fluorophenyl)-2-hydroxyethyl](tetrahydro-2H-pyran-4-yl)amino}propanenitrile (9.38 g) as an oil.

Preparation Example 78

Under an argon atmosphere, diethyl chlorophosphate (4.33 mL) was added to a mixture of 3-{[(2S)-2-(4-chloro-2-fluorophenyl)-2-hydroxyethyl](tetrahydro-2H-pyran-4-yl)amino}propanenitrile (9.38 g) and tetrahydrofuran (47 mL) at −15° C. Then, lithium bis(trimethylsilyl)amide (1.1 M tetrahydrofuran solution, 60 mL) was added dropwise to the reaction mixture while keeping the temperature at −5° C. or lower. The reaction mixture was stirred for 1.5 hours at a temperature within a range of −7° C. to −15° C., and then water (110 mL) was added thereto, followed by extraction by using diisopropyl ether. After being washed with brine, the organic layer was ice-cooled and extracted using 3 M hydrochloric acid. The obtained aqueous layer was basified by the addition of a 50% aqueous sodium hydroxide solution, and extracted using diisopropyl ether. The organic layer was washed with brine and then dried over anhydrous sodium sulfate. The insoluble material was separated by filtration, and the filtrate was concentrated under reduced pressure, thereby obtaining 3-ambo-(3R,4R)-4-(4-chloro-2-fluorophenyl)-1-(tetrahydro-2H-pyran-4-yl)pyrrolidine-3-carbonitrile (8.96 g) as an oil.

Preparation Example 79

Under a nitrogen atmosphere, a 50% aqueous sodium hydroxide solution (4.30 mL) was added to a mixture of 3-ambo-(3R,4R)-4-(4-chloro-2-fluorophenyl)-1-(tetrahydro-2H-pyran-4-yl)pyrrolidine-3-carbonitrile (8.96 g) and ethanol (40 mL), followed by stirring for 5 hours at 100° C.

The reaction mixture was cooled to room temperature, and then ethanol (45 mL) and methanol (80 mL) were added thereto. The mixture was ice-cooled, and concentrated sulfuric acid (2.20 mL) was added thereto. Anhydrous sodium sulfate and celite were added to the mixture, and then the insoluble material was removed by filtration through celite. The solid was washed with a mixed solution of ethanol: methanol (1:1), and the obtained filtrate was concentrated under reduced pressure. To the obtained residue was added 2-propanol (25 mL), followed by stirring for 10 minutes at room temperature. Then, tert-butylmethyl ether (80 mL) was added thereto. The mixture was stirred for 4 hours at 70° C. and then stirred overnight at room temperature. The generated solid was collected by filtration, washed with a mixed solution of 2-propanol:tert-butylmethyl ether (1:3), and then dried at 50° C. under reduced pressure, thereby obtaining (3S,4R)-4-(4-chloro-2-fluorophenyl)-1-(tetrahydro-2H-pyran-4-yl)pyrrolidine-3-carboxylic acid (5.55 g) as a solid.

Preparation Example 80

Under an argon atmosphere, N,N-diisopropylethylamine (800 μL) and propionyl chloride (180 μL) were added to a mixture of (2S)-2-amino-4,4-dimethyl-1-{(3S)-3-methyl-4-[(2-nitrophenyl)sulfonyl]piperazin-1-yl}penta-1-one monohydrochloride (827 mg) and dichloromethane (16 mL) with ice-cooling. The reaction solution was stirred for 4 hours at room temperature and ice-cooled. A saturated sodium hydrogen carbonate solution was added thereto, followed by stirring. Chloroform was added to the reaction mixture so as to separate the organic layer, and the aqueous layer was extracted using chloroform. The organic layers were combined and washed with a saturated aqueous sodium hydrogen carbonate solution, a 5% aqueous citric acid solution, and brine. The organic layer was dried over anhydrous sodium sulfate, and then the insoluble material was separated by filtration. The filtrate was concentrated under reduced pressure, thereby obtaining N-[(2S)-4,4-dimethyl-1-{(3S)-3-methyl-4-[(2-nitrophenyl)sulfonyl]piperazin-1-yl}-1-oxopentan-2-yl]propanamide (861 mg) as a solid.

Preparation Example 81

A solution of 2-nitrobenzenesulfonyl chloride (6.7 g) in tetrahydrofuran (50 mL) was added dropwise for 30 minutes to a mixture of 2-chloro-L-phenylalanine (5 g), water (100 mL), and triethylamine (10 mL) with ice cooling. After being stirred for 3 hours at room temperature, the reaction mixture was ice-cooled, and concentrated hydrochloric acid was added dropwise thereto until the pH became 1. The reaction mixture was diluted with water, and then extraction was performed using chloroform. The organic layer was washed with brine and dried over anhydrous sodium sulfate, and the insoluble material was separated by filtration. The filtrate was concentrated under reduced pressure, chloroform and diethyl ether were added to the obtained residue, and the resultant was concentrated again. The obtained residue was triturated with diethyl ether and then collected by filtration, thereby obtaining 2-chloro-N-[(2-nitrophenyl)sulfonyl]-L-phenylalanine (3.06 g) as a solid.

Preparation Example 82

Under an argon atmosphere, 2-nitrobenzenesulfonyl chloride (2.9 g) and triethylamine (2 mL) were added to a mixture of (3S,4R)-4-(2,4-difluorophenyl)pyrrolidine-3-carboxylic acid methyl ester (2.88 g) and dichloromethane (30 mL) with ice cooling, followed by stirring for 4 days at room temperature. The reaction mixture was diluted with chloroform, a saturated aqueous sodium hydrogen carbonate solution was added thereto. The aqueous layer was extracted using chloroform, and the organic layers were combined and washed with a saturated aqueous sodium hydrogen carbonate solution, a 5% aqueous citric acid solution, and brine. The organic layer was dried over anhydrous sodium sulfate, and the insoluble material was separated by filtration. The filtrate was concentrated under reduced pressure, thereby obtaining (3S,4R)-4-(2,4-difluorophenyl)-1-[(2-nitrophenyl)sulfonyl]pyrrolidine-3-carboxylic acid methyl ester (5.53 g) as a solid.

Preparation Example 83

Under an argon atmosphere, potassium carbonate (2.43 g) and 4-tert-butylbenzene thiol (2.2 mL) were added to a mixture of (2S)-4-{2-chloro-N-[(2-nitrophenyl)sulfonyl]-L-phenylalanine}-2-methylpiperazine-1-carboxylic acid tert-butyl ester (4.99 g) and N,N-dimethylformamide (50 mL), followed by stirring overnight at room temperature. Water was added to the reaction mixture, and extraction was performed using ethyl acetate. The organic layer was dried over anhydrous sodium sulfate. Then, the insoluble material was separated by filtration, and the filtrate was concentrated under reduced pressure. The obtained residue was purified by silica gel column chromatography (chloroform:methanol=100:0 to 90:10), thereby obtaining (2S)-4-(2-chloro-L-phenylalanine)-2-methylpiperazine-1-carboxylic acid tert-butyl ester (3.11 g) as a solid.

Preparation Example 84

Hydrogen chloride (4 M dioxane solution, 4 mL) was added to a mixture of (2S)-4-(N-acetyl-2-chloro-L-phenylalanine)-2-methylpiperazine-1-carboxylic acid tert-butyl ester (3.35 g) and ethanol (35 mL) under ice cooling, followed by stirring overnight at room temperature. Hydrogen chloride (4 M dioxane solution, 4 mL) was added thereto at room temperature, followed by stirring overnight. The reaction mixture was concentrated under reduced pressure, diethyl ether and ethanol were added to the obtained residue, followed by concentration under reduced pressure until the amount of the solvent became about 15 mL. The precipitated solid was separated by filtration, and the filtrate was concentrated, thereby obtaining a solid. Both the solids were mixed together, a saturated aqueous sodium hydrogen carbonate was added thereto, and then extraction was performed using chloroform. The organic layer was dried over anhydrous sodium sulfate. Then, the insoluble material was separated by filtration, and the filtrate was concentrated under reduced pressure. The obtained residue was purified by silica gel column chromatography (chloroform:methanol=100:0 to 90:10), thereby obtaining N-{(2S)-3-(2-chlorophenyl)-1-[(3S)-3-methylpiperazin-1-yl]-1-oxopropan-2-yl}acetamide (968 mg) as a solid.

Preparation Example 85

Under an argon atmosphere, potassium carbonate (340 mg) and 4-tert-butylbenzene thiol (0.33 mL) were added to a mixture of N-{(2S)-1-[(3S)-4-({(3S,4R)-4-(2,4-difluorophenyl)-1-[(2-nitrophenyl)sulfonyl]pyrrolidin-3-yl}carbonyl)-3-methylpiperazin-1-yl]-4,4-dimethyl-1-oxopentan-2-yl}acetamide (650 mg) and N,N-dimethylformamide (6.5 mL), followed by stirring for 4 days at room temperature. Water and ethyl acetate were added to the reaction mixture, and then the reaction mixture was stirred so as to separate the aqueous layer and the organic layer. The organic layer was extracted using 1 M hydrochloric acid, and the aqueous layer was basified using potassium carbonate. The entirety of the aqueous layers was collected and extracted using chloroform. The aqueous layer was extracted again by using a mixed solvent of chloroform-methanol (5:1). The organic layers were combined and dried over anhydrous sodium sulfate. Then, the insoluble material was separated by filtration, and the filtrate was concentrated under reduced pressure. The obtained compound was subjected to azotropic distillation by using toluene, thereby obtaining N-{(2S)-1-[(3S)-4-{[(3S,4R)-4-(2,4-difluorophenyl)pyrrolidin-3-yl]carbonyl}-3-methylpiperazin-1-yl]-4,4-dimethyl-1-oxopentan-2-yl}acetamide (404 mg) as a solid.

Preparation Example 86

Trifluoromethane sulfonic acid samarium (III) (100 mg) was added to a mixture of (4S)-4-benzyl-3-{[1-tert-butyl-4-(5-chloropyridin-2-yl)pyrrolidin-3-yl]carbonyl}-1,3-oxazolidin-2-one (925 mg, Preparation Example 70, a fraction eluted later, a single stereoisomer in which the absolute configuration of the 3-position and the 4-position of the pyrrolidine ring is undetermined) and methanol (15.0 mL), followed by stirring overnight at room temperature. The reaction mixture was concentrated under reduced pressure. The obtained residue was purified by basic silica gel column chromatography (chloroform), thereby obtaining methyl 1-tert-butyl-4-(5-chloropyridin-2-yl)pyrrolidine-3-carboxylate (504 mg, a single stereoisomer in which the absolute configuration of the 3-position and the 4-position of the pyrrolidine ring is undetermined) as an oil.

Preparation Example 87

Concentrated hydrochloric acid (6.00 mL) was added to a mixture of methyl 1-tert-butyl-4-(5-chloropyridin-2-yl)pyrrolidine-3-carboxylate (500 mg, a single stereoisomer in which the absolute configuration of the 3-position and the 4-position of the pyrrolidine ring is undetermined) and dioxane (6.00 mL) at room temperature. The reaction mixture was stirred for 6 hours at 60° C. After being left to cool to room temperature, the reaction mixture was concentrated under reduced pressure. Toluene was added to the obtained residue, followed by concentration under reduced pressure. The obtained residue was dissolved in 2-propanol and then diluted with diisopropyl ether. The mixture was stirred for 1 hour at room temperature, and the generated solid was collected by filtration. The obtained solid was dried at 50° C. under reduced pressure, thereby obtaining 1-tert-butyl-4-(5-chloropyridin-2-yl)pyrrolidine-3-carboxylic acid monohydrochloride (493 mg, a single stereoisomer in which the absolute configuration of the 3-position and the 4-position of the pyrrolidine ring is undetermined) as a solid.

Preparation Example 88

Water (10 mL) and lithium hydroxide monohydrate (1.09 g) were added to a mixture of (3S,4R)-4-(2,4-difluorophenyl)-1-[(2-nitrophenyl)sulfonyl]pyrrolidine-3-carboxylic acid methyl ester (5.53 g) and tetrahydrofuran (50 mL) at room temperature, followed by stirring for 30 minutes. Tetrahydrofuran (50 mL) and water (15 mL) were added to the reaction mixture, followed by stirring for 3 hours. 1 M hydrochloric acid (25.9 mL) was added thereto with ice cooling, and extraction was performed using ethyl acetate. The organic layer was washed with brine and then dried over anhydrous sodium sulfate. The insoluble material was separated by filtration, and the filtrate was concentrated under reduced pressure, thereby obtaining (3S,4R)-4-(2,4-difluorophenyl)-1-[(2-nitrophenyl)sulfonyl]pyrrolidine-3-carboxylic acid (5.04) as a solid.

Preparation Example 89

Acetic acid (30 μL), a formaldehyde solution (37% aqueous solution, 41 μL), sodium acetate (90 g), and sodium triacetoxyborohydride (165 mg) were added to a mixture of (2S)-2-amino-1-[(3S)-4-{[(3S,4R)-1-tert-butyl-4-(2,4-difluorophenyl)pyrrolidin-3-yl]carbonyl}-3-methylpiperazin-1-yl]-2-cyclohexyl ethanone dihydrochloride (300 mg) and dichloromethane (6 mL), followed by stirring for 6 days at room temperature. The reaction mixture was diluted with chloroform, a saturated aqueous sodium hydrogen carbonate solution was added thereto, and then the organic layer was separated. The aqueous layer was extracted using chloroform, and the organic layers were combined and dried over anhydrous sodium sulfate. Then, the insoluble material was separated by filtration, and the solvent was evaporated under reduced pressure. The residue was purified by basic silica gel column chromatography (hexane:ethyl acetate-100:0 to 0:100), thereby obtaining (2S)-1-[(3S)-4-{[(3S,4R)-1-tert-butyl-4-(2,4-difluorophenyl)pyrrolidin-3-yl]carbonyl}-3-methylpiperazin-1-yl]-2-cyclohexyl-2-(methylamino)ethanone (87 mg) as a solid.

Preparation Example 90

Perchloric acid (70%, 0.47 mL) was added to a mixture of (3 S,4R)-4-(4-fluorophenyl)pyrrolidine-3-carboxylic acid monohydrochloride (890 mg) and tert-butyl acetate (11 mL) under ice cooling. The reaction mixture was stirred overnight at room temperature. A 1 M aqueous sodium hydroxide solution was added thereto such that the pH thereof became 8, and extraction was performed using ethyl acetate. The organic layer was washed with brine and then dried over anhydrous magnesium sulfate. The insoluble material was separated by filtration, and the filtrate was concentrated under reduced pressure, thereby obtaining (3S,4R)-4-(4-fluorophenyl)pyrrolidine-3-carboxylic acid tert-butyl ester (889 mg) as an oil.

Preparation Example 91

Hydrogen chloride (4 M dioxane solution, 6.6 mL) was added to a mixture of (3S,4R)-4-(4-fluorophenyl)-1-isopropylpyrrolidine-3-carboxylic acid tert-butyl ester (822 mg) and dioxane (6.6 mL) at room temperature, followed by stirring for 3 days. The reaction mixture was concentrated under reduced pressure, thereby obtaining (3S,4R)-4-(4-fluorophenyl)-1-isopropylpyrrolidine-3-carboxylic acid monohydrochloride (769 mg) as a solid.

Preparation Example 92

Trifluoroacetic acid (4.5 mL) was added to a mixture of (2S)-4-[(2S)-2-acetamide-2-cyclohexylacetyl]-2-methylpiperazine-1-carboxylic acid tert-butyl ester (4.50 g) and dichloromethane (45 mL) under ice cooling, followed by stirring overnight at room temperature. Trifluoroacetic acid (4.5 mL) was added to the reaction mixture, followed by stirring for 2 days at room temperature. The reaction mixture was concentrated, a saturated aqueous sodium hydrogen carbonate solution was added to the residue, and extraction was performed using chloroform. The organic layer was dried over anhydrous sodium sulfate, and the insoluble material was separated by filtration. The filtrate was concentrated under reduced pressure, thereby obtaining N-{(1S)-1-cyclohexyl-2-[(3S)-3-methylpiperazin-1-yl]-2-oxoethyl}acetamide (2.84 g) as a solid.

Preparation Example 94

To a mixture of (3S,4R)-1-benzyl-4-(4-chloro-2-fluorophenyl)pyrrolidine-3-carboxylic acid methyl ester (4.67 g) and 1,2-dichloroethane (75 mL) was added 1-chloroethyl chloroformate (4.50 mL) under ice cooling. The reaction mixture was stirred for 5 hours at 90° C. After being cooled to room temperature, the reaction mixture was concentrated under reduced pressure. Methanol (75 mL) was added to the obtained residue, followed by heating to reflux for 1 hour. After being cooled to room temperature, the reaction mixture was concentrated under reduced pressure. The obtained solid was washed with diisopropyl ether and then dried under reduced pressure, thereby obtaining (3S,4R)-4-(4-chloro-2-fluorophenyl)pyrrolidine-3-carboxylic acid methyl ester monohydrochloride (3.99 g) as a solid.

Preparation Example 96

To a mixture of (S)-(+)-3-hydroxytetrahydrofuran (800 mg), 4-dimethylaminopyridine (111 mg), and pyridine (7.4 mL) was added p-bromobenzenesulfonyl chloride (2.55 g) at 5° C. The reaction mixture was stirred for 24 hours at room temperature. The reaction mixture was concentrated under reduced pressure, and then 1 M hydrochloric acid and ethyl acetate were added thereto to perform liquid separation. The organic layer was washed with brine and then dried over anhydrous magnesium sulfate. The insoluble material was separated by filtration, and the filtrate was concentrated under reduced pressure, thereby obtaining 4-bromobenzene sulfonic acid (3S)-tetrahydrofuran-3-yl ester (1.57 g) as an oil.

Preparation Example 98

Under an argon atmosphere, a mixture of 4-bromobenzene sulfonic acid (3S)-tetrahydrofuran-3-yl ester (388 mg), N-{(2S)-1-[(3S)-4-{[(3 S,4R)-4-(4-chloro-2-fluorophenyl)pyrrolidin-3-yl]carbonyl}-3-methylpiperazin-1-yl]-4,4-dimethyl-1-oxopentan-2-yl}acetamide (250 mg), N,N-diisopropylethylamine (0.43 mL), and N-methyl-2-pyrrolidone (2.5 mL) was stirred for 5 hours at 110° C. The reaction mixture was cooled to room temperature, and ethyl acetate was then added thereto, followed by washing with water and drying over anhydrous sodium sulfate. Then, the insoluble material was separated by filtration, and the solvent was evaporated under reduced pressure. The residue was purified by silica gel column chromatography (chloroform-methanol=100:0 to 80:20), thereby obtaining N-{(2S)-1-[(3S)-4-({(3S,4R)-4-(4-chloro-2-fluorophenyl)-1-[(3R)-tetrahydrofuran-3-yl]pyrrolidin-3-yl}carbonyl)-3-methylpiperazin-1-yl]-4,4-dimethyl-1-oxopentan-2-yl}acetamide (85 mg) as an oil.

Preparation Example 101

Potassium carbonate (42 g) was added to a mixture of tetrahydro-2H-pyran-4-amine hydrochloride (14 g) and acetonitrile (500 mL), followed by stirring for 15 minutes at room temperature. Chloromethyltrimethylsilane (22 mL) and potassium iodide (19 g) were added to the reaction mixture, followed by stirring for 36 hours at 60° C. After the reaction mixture was cooled to room temperature, the solid was separated by filtration, and the filtrate was concentrated under reduced pressure. The obtained residue was purified by silica gel column chromatography (chloroform-methanol=95:5 to 90:10), thereby obtaining N-[(trimethylsilyl)methyl]tetrahydro-2H-pyran-4-amine (16.8 g) as an oil.

Preparation Example 102

Potassium carbonate (620 mg) and methanol (7.3 mL) were added to an aqueous formaldehyde solution (37%, 15 mL) under ice cooling. N-[(trimethylsilyl)methyl]tetrahydro-2H-pyran-4-amine (16.8 g) was added dropwise to the reaction mixture under ice cooling, followed by stirring for 1 hour. The reaction mixture was stirred for 1 hour at 10° C. to 15° C. The reaction mixture was ice-cooled, and potassium carbonate (25 g) was added thereto, followed by stirring for 1 hour. The reaction mixture was heated to room temperature and then stirred overnight. Diethyl ether was added to the reaction mixture, and the insoluble material was removed by decantation. The organic layer was washed with brine and dried over anhydrous sodium sulfate. The insoluble material was separated by filtration and concentrated under reduced pressure (water bath 21° C., 100 mbar), thereby obtaining N-(methoxymethyl)-N-[(trimethylsilyl)methyl]tetrahydro-2H-pyran-4-amine (19.1 g) as an oil.

Preparation Example 103

To a mixture of tert-butyl (2R)-2-methylpiperazine-1-carboxylate (8.40 g), triethylamine (6.5 mL), and dichloromethane (60 mL) was added 2-nitrobenzenesulfonyl chloride (9.48 g) under ice cooling. The reaction mixture was stirred for 1 hour at room temperature. The reaction mixture was concentrated under reduced pressure, and ethyl acetate and a saturated aqueous sodium hydrogen carbonate solution were added to the obtained residue to perform liquid separation. The organic layer was washed with water, 0.5 M hydrochloric acid, water, an aqueous sodium hydrogen carbonate solution, and brine, followed by drying over anhydrous magnesium sulfate. The insoluble material was separated by filtration, and the filtrate was concentrated under reduced pressure, thereby obtaining (2R)-2-methyl-4-[(2-nitrophenyl)sulfonyl]piperazine-1-carboxylic acid tert-butyl ester (16.2 g) as a solid.

Preparation Example 104

At room temperature, acetone (0.74 mL), acetic acid (0.19 mL), and sodium triacetoxyborohydride (1.07 g) were added to a mixture of (3S,4R)-4-(4-fluorophenyl)pyrrolidine-3-carboxylic acid tert-butyl ester (889 mg) and dichloromethane (14 mL). The reaction mixture was stirred for 1 hour at room temperature. A saturated aqueous sodium hydrogen carbonate solution was added to the reaction mixture, and extraction was performed using chloroform. The organic layer was dried over anhydrous magnesium sulfate, and the insoluble material was separated by filtration. The solvent was evaporated under reduced pressure, and the obtained residue was purified by silica gel column chromatography (chloroform-methanol=100:0 to 98:2), thereby obtaining (3S,4R)-4-(4-fluorophenyl)-1-isopropylpyrrolidine-3-carboxylic acid tert-butyl ester (822 mg) as an oil.

Example 1

Under an argon atmosphere, N,N-diisopropylethylamine (2.5 mL) and acetyl chloride (320 µL) were added to a mixture of (2S)-2-amino-1-[(2R,5S)-4-{[(3S,4R)-1-tert-butyl-4-(2,4-difluorophenyl)pyrrolidin-3-yl]carbonyl}-2,5-dimethylpiperazin-1-yl]-4,4-dimethylpentan-1-one dihydrochloride (2.39 g) and dichloromethane (25 mL) with ice cooling, followed by stirring for 1 hour at room temperature. The reaction mixture was diluted with chloroform, a saturated aqueous sodium hydrogen carbonate solution was added thereto under ice cooling while stirring, and the organic layer was separated. The aqueous layer was extracted using chloroform, and the organic layers were combined and washed with a saturated aqueous sodium hydrogen carbonate solution. The organic layer was dried over anhydrous sodium sulfate, the insoluble material was separated by filtration, and the solvent was evaporated under reduced pressure. The residue was purified by silica gel column chromatography (chloroform-methanol=100:0 to 80:20), thereby obtaining N-{(2S)-1-[(2R,5S)-4-{[(3 S,4R)-1-tert-butyl-4-(2,4-difluorophenyl)pyrrolidin-3-yl]carbonyl}-2,5-dimethylpiperazin-1-yl]-4,4-dimethyl-1-oxopentan-2-yl}acetamide (1.57 g) as a solid.

Example 4

At room temperature, hydrogen chloride (4 M ethyl acetate solution, 700 µL) was added to a mixture of N-{(2S)-1-[(2R,5S)-4-{[(3S,4R)-1-tert-butyl-4-(2,4-difluorophenyl)pyrrolidin-3-yl]carbonyl}-2,5-dimethylpiperazin-1-yl]-4,4-dimethyl-1-oxopentan-2-yl}acetamide (1 g) and diethyl ether (20 mL), followed by stirring for 30 minutes. The precipitated solid was collected by filtration and then dried under reduced pressure, thereby obtaining N-{(2S)-1-[(2R,5S)-4-{[(3 S,4R)-1-tert-butyl-4-(2,4-difluorophenyl)pyrrolidin-3-yl]carbonyl}-2,5-dimethylpiperazin-1-yl]-4,4-dimethyl-1-oxopentan-2-yl}acetamide monohydrochloride (1.01 g) as a solid.

Example 6

Under a nitrogen atmosphere, N,N-diisopropylethylamine (48 mL) and acetyl chloride (5.3 mL) were added to a mixture of (2S)-2-amino-1-[(3S)-4-{[(3S,4R)-1-tert-butyl-4-(2,4-difluorophenyl)pyrrolidin-3-yl]carbonyl}-3-methylpiperazin-1-yl]-2-cyclohexyl ethanone dihydrochloride (40.43 g) and dichloromethane (600 mL) with ice cooling. The reaction mixture was stirred for 3 hours at room temperature and then ice-cooled, and a 5% aqueous sodium hydrogen carbonate solution (500 mL) was added thereto, followed by stirring for 30 minutes. The organic layer was separated, and the aqueous layer was extracted using chloroform. The organic layers were combined and washed with a 5% aqueous sodium hydrogen carbonate solution and brine. The organic layer was dried over anhydrous sodium sulfate, the insoluble material was then separated by filtration, and the filtrate was concentrated under reduced pressure. The obtained residue was purified by silica gel column chromatography (chloroform-methanol=100:0 to 80:20), thereby obtaining a solid. Ethyl acetate (600 mL) was added to the obtained solid, and then the insoluble material was separated by filtration. Hydrogen chloride (4 M ethyl acetate solution, 18 mL) was added to the filtrate with ice cooling, followed by stirring for 10 minutes. The solvent was evaporated under reduced pressure, and diethyl ether (250 mL) was added to the residue under an argon atmosphere, followed by stirring for 30 minutes. The precipitated solid was collected by filtration and then dried under reduced pressure, thereby obtaining N-{(1S)-2-[(3S)-4-{[(3S,4R)-1-tert-butyl-4-(2,4-difluorophenyl)pyrrolidin-3-yl]carbonyl}-3-methylpiperazin-1-yl]-1-cyclohexyl-2-oxoethyl}acetamide monohydrochloride (31.3 g) as a solid.

Example 16

Under an argon atmosphere, N-acetyl-3-cyclopentyl-L-alanine (119 mg), O-(7-aza-1H-benzotriazol-1-yl)-N,N,N',N'-tetramethyluronium hexafluorophosphate (291 mg), and N,N-diisopropylethylamine (0.14 mL) were added to a mixture of [(3S,4R)-1-tert-butyl-4-(2,4-difluorophenyl)pyrrolidin-3-yl][(2S)-2-methylpiperazin-1-yl]methane (200 mg) and N,N-dimethylformamide (4 mL) with ice cooling, followed by stirring overnight at room temperature. Ethyl acetate, a saturated aqueous sodium hydrogen carbonate solution, and water were added to the reaction mixture. The aqueous layer was extracted using ethyl acetate, and the organic layers were combined and washed with brine. The organic layer was dried over anhydrous magnesium sulfate, the insoluble material was separated by filtration, and the filtrate was concentrated under reduced pressure. The obtained residue was purified by silica gel column chromatography (chloroform:methanol=100:0 to 90:10), thereby obtaining an oil. The obtained oil was dissolved in ethyl acetate (2 mL), and hydrogen chloride (4 M ethyl acetate solution, 1 mL) was added thereto, followed by stirring for 10 minutes at room temperature. The solvent was evaporated under reduced pressure, and then the resultant was made into powder by using diethyl ether. The obtained solid was washed with diethyl ether and then dried, thereby obtaining N-((2S)-1-[(3S)-4-{[(3S,4R)-1-tert-butyl-4-(2,4-difluorophenyl)pyrrolidin-3-yl]carbonyl}-3-methylpiperazin-1-yl]-3-cyclopentyl-1-oxopropan-2-yl) acetamide monohydrochloride (186 mg) as a solid.

Example 18

[(3 S,4R)-1-tert-butyl-4-(2,4-difluorophenyl)pyrrolidin-3-yl][(2S)-2-methylpiperazin-1-yl]methanone dihydrochloride (272 mg), O-(7-aza-1H-benzotriazol-1-yl)-N,N,N',N'-tetramethyluronium hexafluorophosphate (284 mg), and N,N-diisopropylethylamine (0.319 mL) were added to a mixture of N-acetyl-3-(4,4-dimethylcyclohexyl)-L-alanine (150 mg) and N,N-dimethylformamide (3 mL), followed by stirring for 40 minutes at room temperature. Water was added to the reaction mixture, and extraction was performed using ethyl acetate. The organic layer was washed with water and then with a saturated aqueous sodium hydrogen carbonate solution. The organic layer was washed with brine and dried over anhydrous magnesium sulfate. The insoluble material was separated by filtration, and the filtrate was concentrated under reduced pressure. The obtained residue was purified by silica gel column chromatography (chloroform:methanol=100:0 to 92:8). Hydrogen chloride (4 M ethyl acetate solution, 0.311 mL) was added to the obtained oil in an ethyl acetate solution (2 mL), followed by stirring for 30 minutes at room temperature. The reaction mixture was concentrated, and the obtained solid was washed with hexane and dried, thereby obtaining N-[(2S)-1-[(3S)-4-{[(3 S,4R)-1-tert-butyl-4-(2-difluorophenyl)pyrrolidin-3-yl]carbonyl}-3-methylpiperazin-1-yl]-3-(4,4-dimethylcyclohexyl)-1-oxopropan-2-yl]acetamide monohydrochloride (78 mg) as a solid.

Example 20

Under an argon atmosphere, (3 S,4R)-4-(4-chloro-2-fluorophenyl)-1-(tetrahydro-2H-pyran-4-yl)pyrrolidine-3-carboxylic acid (145 mg), O-(7-aza-1H-benzotriazol-1-yl)-N,N,N',N'-tetramethyluronium hexafluorophosphate (185 mg), and N,N-diisopropylethylamine (85 μL) were added to a mixture of N-{(2S)-4,4-dimethyl-1-[(3S)-3-methylpiperazin-1-yl]-1-oxopentan-2-yl}acetamide (100 mg) and N,N-dimethylformamide (2 mL) with ice cooling, followed by stirring for 7 hours at room temperature. The reaction mixture was ice-cooled, and a saturated aqueous sodium hydrogen carbonate solution was added thereto, followed by stirring. Water was added to the reaction mixture, and extraction was performed using ethyl acetate. The organic layer was washed with a saturated aqueous sodium hydrogen carbonate solution, water, and brine. The organic layer was dried over anhydrous sodium sulfate, the insoluble material was separated by filtration, and the filtrate was concentrated under reduced pressure. The obtained residue was purified by silica gel column chromatography (chloroform:methanol=100:0 to 80:20). Hydrogen chloride (4 M ethyl acetate solution, 200 μL) was added to a mixture of the obtained compound and ethyl acetate (2 mL), followed by stirring. The solvent was evaporated under reduced pressure, and diethyl ether was added to the obtained residue so as to make the residue into powder. The solid was collected by filtration and then dried under reduced pressure, thereby obtaining N-{(2S)-1-[(3S)-4-{[(3 S,4R)-4-(4-chloro-2-fluorophenyl)-1-(tetrahydro-2H-pyran-4-yl)pyrrolidin-3-yl]carbonyl}-3-methylpiperazin-1-yl]-4,4-dimethyl-1-oxopentan-2-yl}acetamide monohydrochloride (141 mg) as a solid.

Example 24

At room temperature, acetone (55 μL) and acetic acid (15 μL) were added to a mixture of N-{(2S)-1-[(3S)-4-{[(3 S,4R)-4-(2,4-difluorophenyl)pyrrolidin-3-yl]carbonyl}-3-methylpiperazin-1-yl]-4,4-dimethyl-1-oxopentan-2-yl}acetamide (120 mg) and dichloromethane (2.4 mL), followed by stirring for 30 minutes. Sodium triacetoxyborohydride (210 mg) was added to the mixture with ice cooling, followed by stirring overnight at room temperature. Chloroform and a saturated aqueous sodium hydrogen carbonate solution were added to the reaction mixture such that the organic layer was separated. The aqueous layer was extracted using chloroform, and the organic layers were combined and washed with a saturated aqueous sodium hydrogen carbonate solution and brine. The organic layer was dried over anhydrous sodium sulfate, the insoluble material was separated by filtration, and the filtrate was concentrated under reduced pressure. The obtained residue was purified by silica gel column chromatography (chloroform:methanol=100:0 to 80:20). Hydrogen chloride (4 M ethyl acetate solution, 200 μL) was added to a mixture of the obtained compound and ethyl acetate (2 mL) with ice cooling, followed by stirring. The reaction mixture was concentrated, and the obtained residue was triturated with diethyl ether, then collected by filtration, and dried, thereby obtaining N-{(2S)-1-[(3S)-4-{[(3S,4R)-4-(2,4-difluorophenyl)-1-isopropylpyrrolidin-3-yl]carbonyl}-3-methylpiperazin-1-yl]-4,4-dimethyl-1-oxopentan-2-yl}acetamide monohydrochloride (89 mg) as a solid.

Example 28

Acetic acid (20 μL) and a formaldehyde solution (37% aqueous solution, 145 μL) were added to a mixture of (2S)-2-amino-1-[(3S)-4-{[(3 S,4R)-1-tert-butyl-4-(2,4-difluorophenyl)pyrrolidin-3-yl]carbonyl}-3-methylpiperazin-1-yl]-3-(2-chlorophenyl)propan-1-one (200 mg) and dichloromethane (4 mL), followed by stirring. Sodium triacetoxyborohydride (230 mg) was added thereto at room temperature, followed by stirring for 23 hours. Chloroform and a saturated aqueous sodium hydrogen carbonate solution were added to the reaction mixture, and the organic layer was separated. The aqueous layer was extracted using chloroform, and the organic layers were combined and dried over anhydrous sodium sulfate. The insoluble material was separated by filtration, and the filtrate was concentrated under reduced pressure. The obtained residue was purified by silica gel column chromatography (chloroform:methanol=100:0 to 90:10). The obtained compound was dissolved in ethyl acetate (3 mL), and hydrogen chloride (4 M ethyl acetate solution, 200 µL) was added thereto with ice cooling, followed by stirring for 10 minutes. The reaction mixture was concentrated, thereby obtaining a solid. The obtained solid was washed with diethyl ether and then dried, thereby obtaining (2S)-1-[(3S)-4-{[(3 S,4R)-1-tert-butyl-4-(2,4-difluorophenyl)pyrrolidin-3-yl]carbonyl}-3-methylpiperazin-1-yl]-3-(2-chlorophenyl)-2-(dimethylamino)propan-1-one dihydrochloride (114 mg) as a solid.

Example 29

Under an argon atmosphere, triethylamine (90 µL) and methanesulfonyl chloride (15 µL) were added to a mixture of (2S)-2-amino-1-[(3S)-4-{[(3S,4R)-4-(4-chloro-2-fluorophenyl)-1-(tetrahydro-2H-pyran-4-yl)pyrrolidin-3-yl]carbonyl}-3-methylpiperazin-1-yl]-4-methylpentan-1-one dihydrochloride (100 mg) and dichloromethane (2 mL) with ice cooling, followed by stirring overnight at room temperature. Chloroform and a saturated aqueous sodium hydrogen carbonate solution were added to the reaction mixture. The aqueous layer was separated, and extracted using chloroform. The organic layers were combined and dried over anhydrous sodium sulfate. Then, the insoluble material was separated by filtration. The filtrate was concentrated under reduced pressure, and the obtained residue was purified by silica gel column chromatography (chloroform:methanol=100:0 to 80:20). Hydrogen chloride (4 M ethyl acetate solution, 200 µL) was added to a mixture of the obtained compound and ethyl acetate (2 mL) with ice cooling, followed by stirring. The solvent was evaporated under reduced pressure to afford a residue. The obtained residue was triturated with diethyl ether. The solid was collected by filtration and then dried under reduced pressure, thereby obtaining N-{(2S)-1-[(3S)-4-{[(3S,4R)-4-(4-chloro-2-fluorophenyl)-1-(tetrahydro-2H-pyran-4-yl)pyrrolidin-3-yl]carbonyl}-3-methylpiperazin-1-yl]-4-methyl-1-oxopentan-2-yl}methanesulfonamide monohydrochloride (85 mg) as a solid.

Example 30

Hydrogen chloride (4 M dioxane solution, 165 mL) was added to a mixture of {(1S)-2-[(3S)-4-{[(3 S,4R)-1-tert-butyl-4-(2,4-difluorophenyl)pyrrolidin-3-yl]carbonyl}-3-methylpiperazin-1-yl]-1-cyclohexyl-2-oxoethyl}carbamic acid tert-butyl ester (39.9 g) and ethanol (400 mL) with ice cooling, followed by stirring overnight at room temperature. The solvent was evaporated under reduced pressure, thereby obtaining (2S)-2-amino-1-[(3S)-4-{[(3S,4R)-1-tert-butyl-4-(2,4-difluorophenyl)pyrrolidin-3-yl]carbonyl}-3-methylpiperazin-1-yl]-2-cyclohexylethanone dihydrochloride (40.6 g) as a solid.

The compounds of Preparation Examples and Examples shown in the following tables were prepared by the same method as in the Preparation Examples and Examples described above.

TABLE 5

| PEx | PSyn | Str | DAT |
|---|---|---|---|
| 1 | 1 | [structure] | ESI+: 480 |
| 2 | 1 | [structure] | ESI+: 466 |

TABLE 5-continued

| PEx | PSyn | Str | DAT |
|---|---|---|---|
| 3 | 1 | (structure) | ESI+: 462 |
| 4 | 1 | (structure) | ESI+: 482 |

TABLE 6

| PEx | PSyn | Str | DAT |
|---|---|---|---|
| 5 | 1 | (structure) | ESI+: 524 |
| 6 | 1 | (structure) | ESI+: 558 |

TABLE 6-continued
| PEx | PSyn | Str | DAT |
|---|---|---|---|
| 7 | 1 | 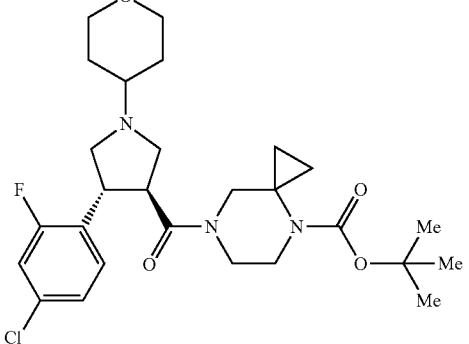 | ESI+: 522 |
| 8 | 1 | 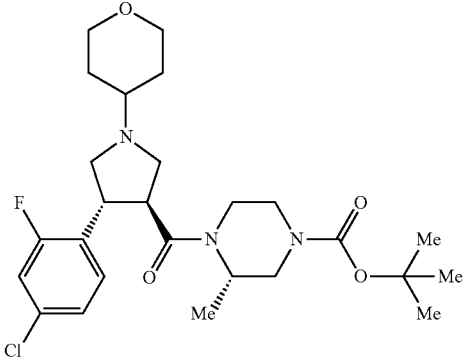 [SMILES: C[C@H]1CN(C(=O)OC(C)(C)C)CCN1C(=O)[C@@H]1CN(C2CCOCC2)C[C@H]1c1ccc(Cl)cc1F] | ESI+: 510 |
TABLE 7
| PEx | PSyn | Str | DAT |
|---|---|---|---|
| 9 | 1 | 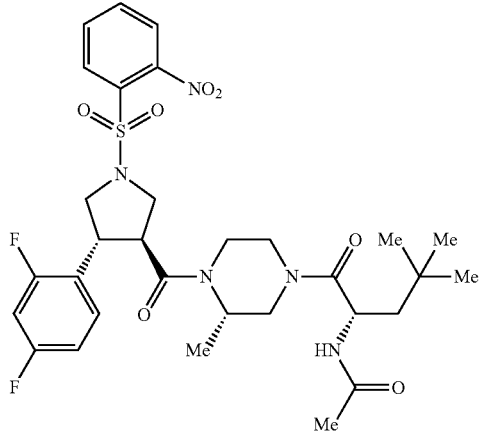 [SMILES: CC(=O)N[C@@H](CC(C)(C)C)C(=O)N1CCN(C(=O)[C@@H]2CN(S(=O)(=O)c3ccccc3[N+](=O)[O-])C[C@H]2c2ccc(F)cc2F)[C@@H](C)C1] | ESI+: 664 |

TABLE 7-continued
| PEx | PSyn | Str | DAT |
|---|---|---|---|
| 10 | 10 | 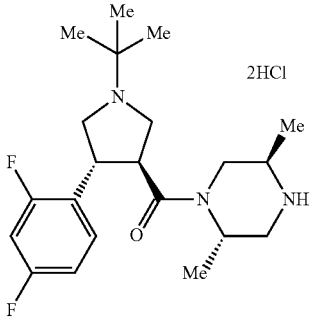 [SMILES: C[C@@H]1CN(C(=O)[C@@H]2CN(C(C)(C)C)C[C@H]2c2ccc(F)cc2F)[C@@H](C)CN1] | ESI+: 380 |
| 11 | 10 | 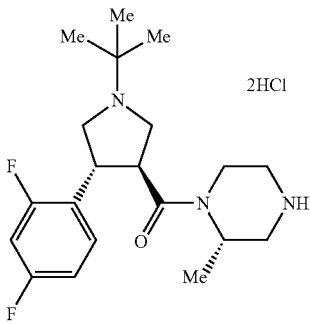 [SMILES: C[C@H]1CNCCN1C(=O)[C@@H]1CN(C(C)(C)C)C[C@H]1c1ccc(F)cc1F] | ESI+: 366 |
| 12 | 10 | 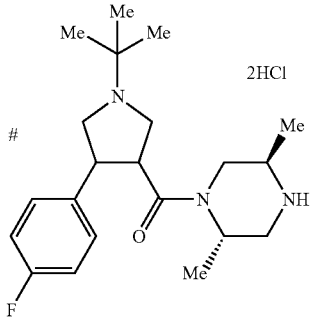 [SMILES: C[C@@H]1CN(C(=O)C2CN(C(C)(C)C)CC2c2ccc(F)cc2)[C@@H](C)CN1] | ESI+: 362 |
| 13 | 10 | 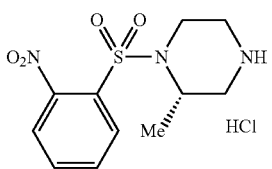 [SMILES: C[C@H]1CNCCN1S(=O)(=O)c1ccccc1[N+](=O)[O-] ; Cl] | ESI+: 286 |

TABLE 8
| PEx | PSYn | Str | DAT |
|---|---|---|---|
| 14 | 10 | | ESI+: 424 |
| 15 | 10 | | ESI+: 458 |
| 16 | 10 | | ESI+: 422 |
| 17 | 10 | | ESI+: 410 |
TABLE 9
| PEx | PSyn | Str | DAT |
|---|---|---|---|
| 18 | 18 | | ESI+: 608 |
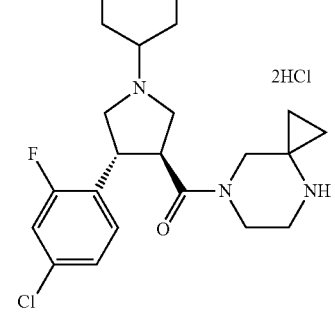

TABLE 9-continued
| PEx | PSyn | Str | DAT |
|---|---|---|---|
| 19 | 18 | 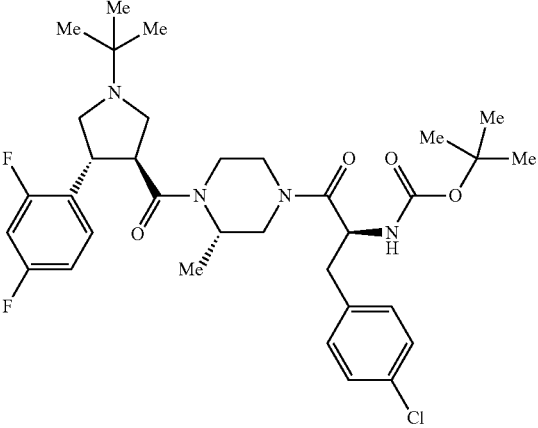 [SMILES: C[C@H]1CN(C(=O)[C@H](Cc2ccc(Cl)cc2)NC(=O)OC(C)(C)C)CCN1C(=O)[C@@H]1CN(C(C)(C)C)C[C@H]1c1ccc(F)cc1F] | ESI+: 647 |
| 20 | 18 | 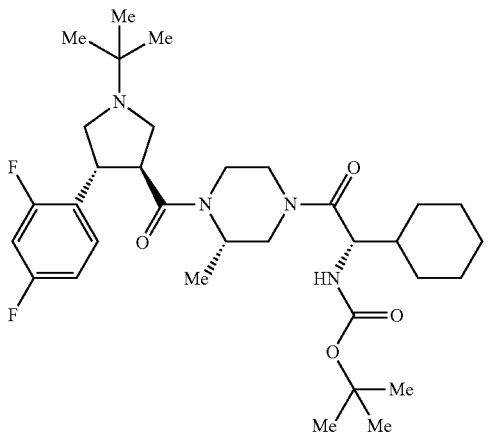 [SMILES: C[C@H]1CN(C(=O)[C@@H](NC(=O)OC(C)(C)C)C2CCCCC2)CCN1C(=O)[C@@H]1CN(C(C)(C)C)C[C@H]1c1ccc(F)cc1F] | ESI+: 606 |
TABLE 10
| PEx | PSyn | Str | DAT |
|---|---|---|---|
| 21 | 18 | 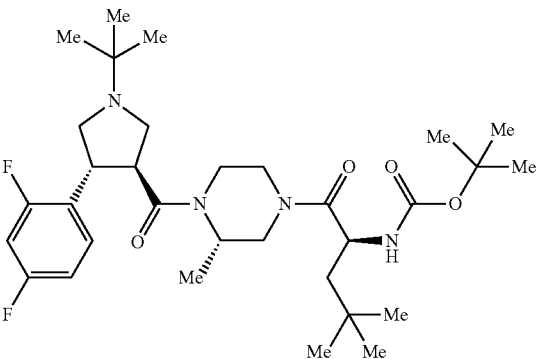 [SMILES: C[C@H]1CN(C(=O)[C@H](CC(C)(C)C)NC(=O)OC(C)(C)C)CCN1C(=O)[C@@H]1CN(C(C)(C)C)C[C@H]1c1ccc(F)cc1F] | ESI+: 594 |

TABLE 10-continued
| PEx | PSyn | Str | DAT |
|---|---|---|---|
| 22 | 18 | 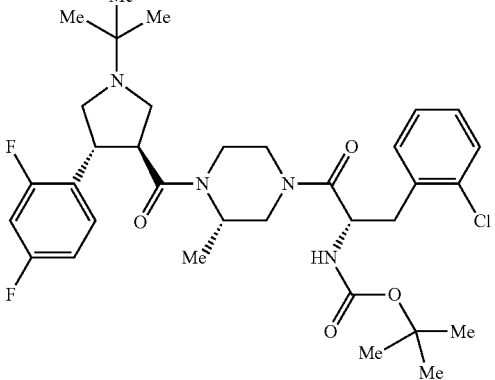 | ESI+: 648 |
| 23 | 18 | 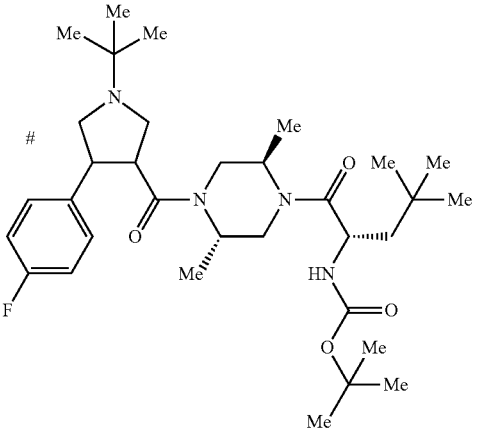 [SMILES: C[C@@H]1CN(C(=O)C2CN(C(C)(C)C)CC2c2ccc(F)cc2)[C@@H](C)CN1C(=O)[C@H](CC(C)(C)C)NC(=O)OC(C)(C)C] | ESI+: 590 |
| 24 | 18 | 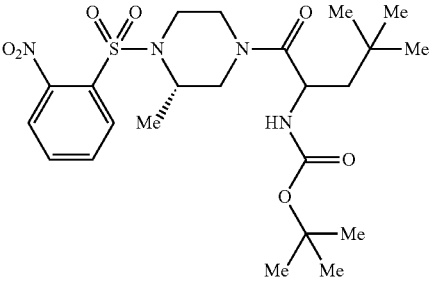 [SMILES: C[C@H]1CN(C(=O)C(CC(C)(C)C)NC(=O)OC(C)(C)C)CCN1S(=O)(=O)c1ccccc1[N+](=O)[O-]] | ESI+: 513 |

TABLE 11
| PEx | PSyn | Str | DAT |
|---|---|---|---|
| 25 | 18 | 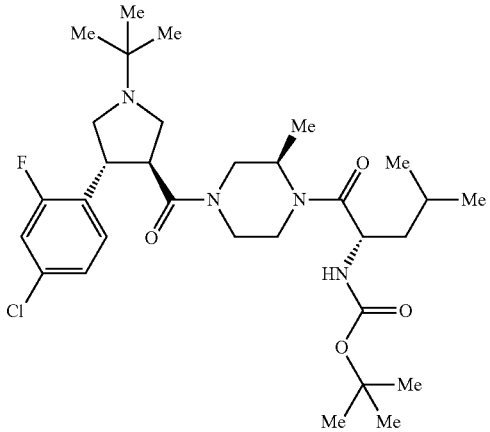 [SMILES: CC(C)C[C@H](NC(=O)OC(C)(C)C)C(=O)N1CCN(C(=O)[C@@H]2CN(C(C)(C)C)C[C@H]2c2ccc(Cl)cc2F)C[C@H]1C] | ESI+: 596 |
| 26 | 18 | 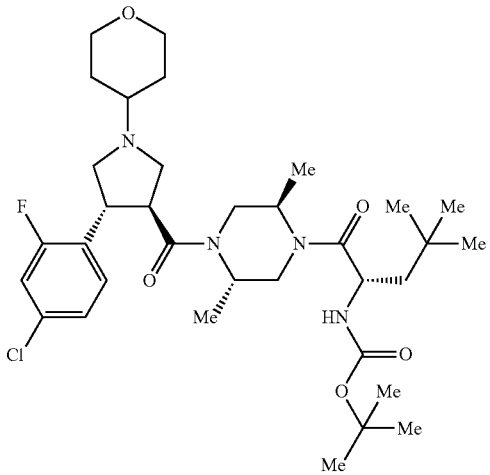 [SMILES: C[C@@H]1CN(C(=O)[C@@H]2CN(C3CCOCC3)C[C@H]2c2ccc(Cl)cc2F)[C@@H](C)CN1C(=O)[C@H](CC(C)(C)C)NC(=O)OC(C)(C)C] | ESI+: 652 |
| 27 | 18 | 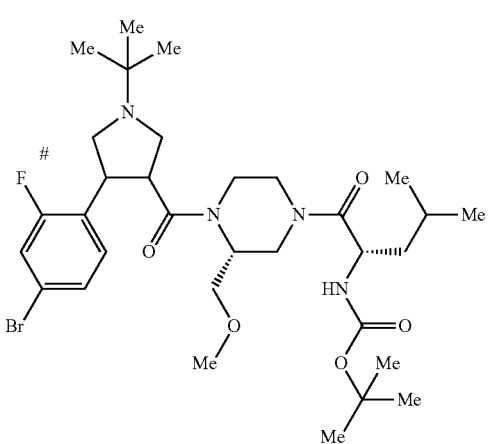 [SMILES: COC[C@H]1CN(C(=O)[C@H](CC(C)C)NC(=O)OC(C)(C)C)CCN1C(=O)C1CN(C(C)(C)C)CC1c1ccc(Br)cc1F] | ESI+: 671 |

TABLE 12
| PEx | PSyn | Str | DAT |
|---|---|---|---|
| 28 | 18 | 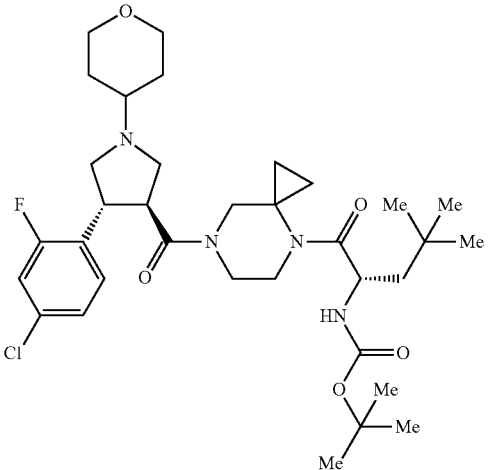 [SMILES: CC(C)(C)C[C@H](NC(=O)OC(C)(C)C)C(=O)N1CCN(C(=O)[C@@H]2CN(C3CCOCC3)C[C@H]2c2ccc(Cl)cc2F)CC12CC2] | ESI+: 650 |
| 29 | 18 | 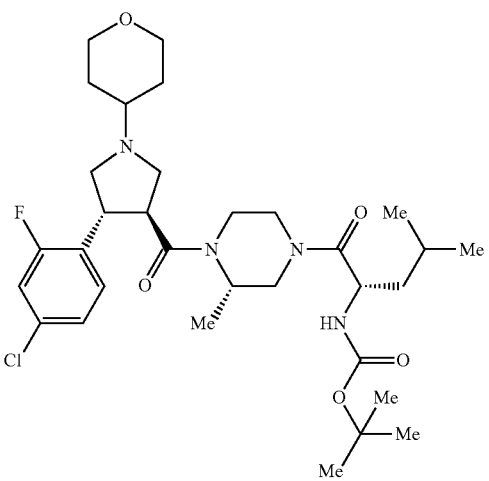 [SMILES: CC(C)C[C@H](NC(=O)OC(C)(C)C)C(=O)N1CCN(C(=O)[C@@H]2CN(C3CCOCC3)C[C@H]2c2ccc(Cl)cc2F)[C@@H](C)C1] | ESI+: 624 |
| 30 | 18 | 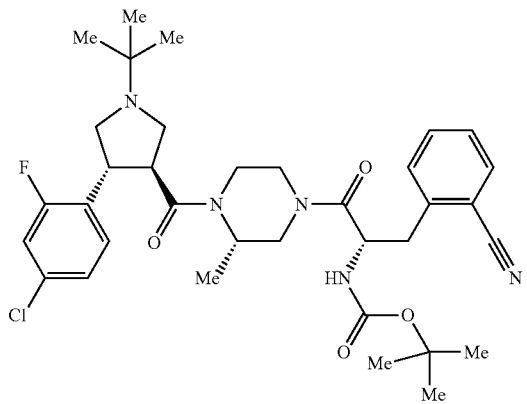 [SMILES: C[C@H]1CN(C(=O)[C@H](Cc2ccccc2C#N)NC(=O)OC(C)(C)C)CCN1C(=O)[C@@H]1CN(C(C)(C)C)C[C@H]1c1ccc(Cl)cc1F] | ESI+: 638 |

TABLE 12-continued
| PEx | PSyn | Str | DAT |
|---|---|---|---|
| 31 | 18 | | ESI-: 565 |
TABLE 13
| PEx | PSyn | Str | DAT |
|---|---|---|---|
| 32 | 18 | | ESI+: 592 |
| 33 | 33 | | ESI+: 508 |

TABLE 13-continued
| PEx | PSyn | Str | DAT |
|---|---|---|---|
| 34 | 33 | 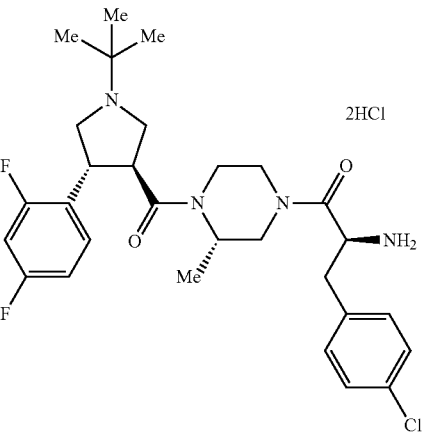 [SMILES: C[C@H]1CN(C(=O)[C@@H](N)Cc2ccc(Cl)cc2)CCN1C(=O)[C@@H]1CN(C(C)(C)C)C[C@H]1c1ccc(F)cc1F] | ESI+: 547 |
| 35 | 33 | 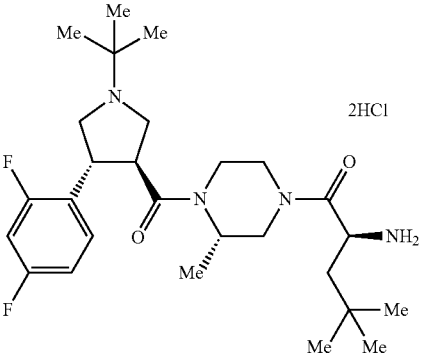 [SMILES: C[C@H]1CN(C(=O)[C@@H](N)CC(C)(C)C)CCN1C(=O)[C@@H]1CN(C(C)(C)C)C[C@H]1c1ccc(F)cc1F] | ESI+: 494 |
TABLE 14
| PEx | PSyn | Str | DAT |
|---|---|---|---|
| 36 | 33 | 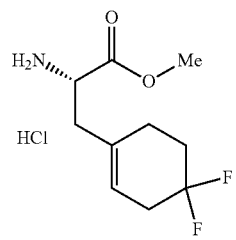 [SMILES: Cl ; COC(=O)[C@@H](N)CC1=CCC(F)(F)CC1] | ESI+: 220 |
| 37 | 33 | 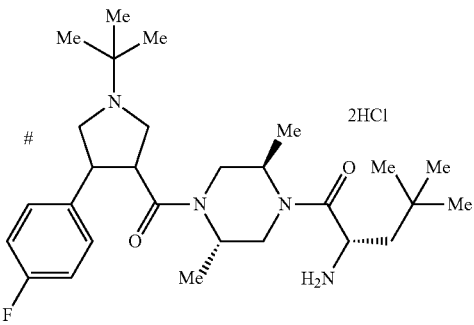 [SMILES: C[C@@H]1CN(C(=O)C2CN(C(C)(C)C)CC2c2ccc(F)cc2)[C@@H](C)CN1C(=O)[C@@H](N)CC(C)(C)C] | ESI+: 490 |

TABLE 14-continued
| PEx | PSyn | Str | DAT |
|---|---|---|---|
| 38 | 33 | 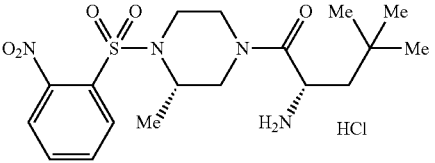 [SMILES: C[C@H]1CN(C(=O)[C@@H](N)CC(C)(C)C)CCN1S(=O)(=O)c1ccccc1[N+](=O)[O-] ; Cl] | ESI+: 413 |
| 39 | 33 | 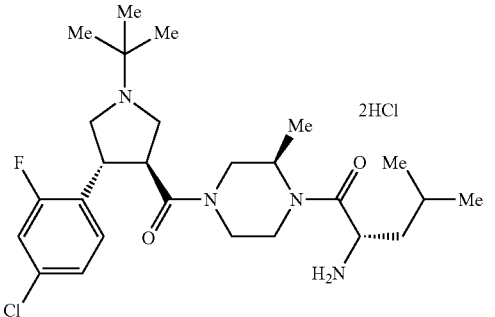 [SMILES: CC(C)C[C@H](N)C(=O)N1CCN(C(=O)[C@@H]2CN(C(C)(C)C)C[C@H]2c2ccc(Cl)cc2F)C[C@H]1C] | ESI+: 495 |
| 40 | 33 | 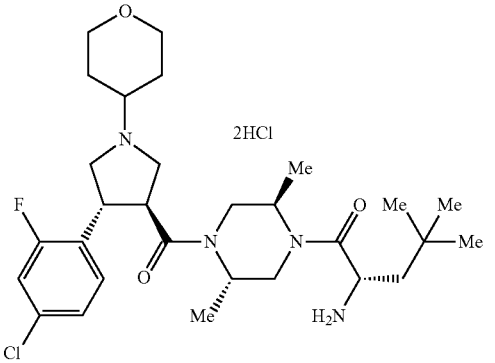 [SMILES: C[C@@H]1CN(C(=O)[C@@H]2CN(C3CCOCC3)C[C@H]2c2ccc(Cl)cc2F)[C@@H](C)CN1C(=O)[C@@H](N)CC(C)(C)C] | ESI+: 551 |
TABLE 15
| PEx | PSyn | Str | DAT |
|---|---|---|---|
| 41 | 33 | 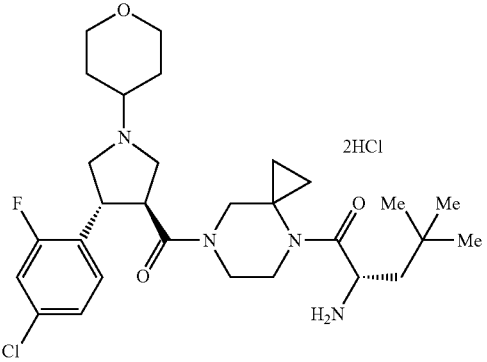 [SMILES: CC(C)(C)C[C@H](N)C(=O)N1CCN(C(=O)[C@@H]2CN(C3CCOCC3)C[C@H]2c2ccc(Cl)cc2F)CC12CC2] | ESI+: 550 |

TABLE 15-continued
| PEx | PSyn | Str | DAT |
|-----|------|-----|-----|
| 42 | 33 | 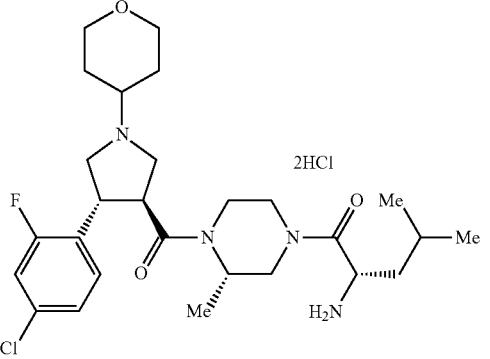 [SMILES: CC(C)C[C@H](N)C(=O)N1CCN(C(=O)[C@@H]2CN(C3CCOCC3)C[C@H]2c2ccc(Cl)cc2F)[C@@H](C)C1] | ESI+: 524 |
| 43 | 33 | 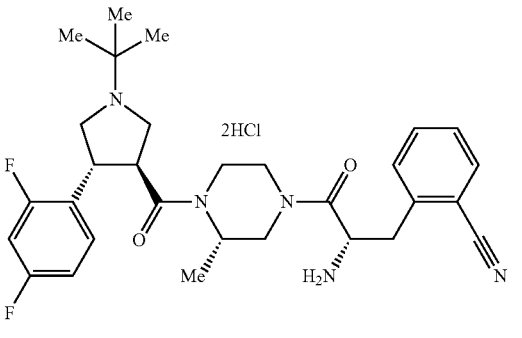 [SMILES: C[C@H]1CN(C(=O)[C@@H](N)Cc2ccccc2C#N)CCN1C(=O)[C@@H]1CN(C(C)(C)C)C[C@H]1c1ccc(F)cc1F] | ESI+: 538 |
| 44 | 33 | 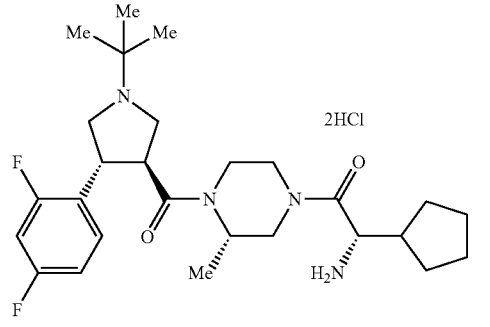 [SMILES: C[C@H]1CN(C(=O)[C@@H](N)C2CCCC2)CCN1C(=O)[C@@H]1CN(C(C)(C)C)C[C@H]1c1ccc(F)cc1F] | ESI+: 491 |
TABLE 16
| PEx | PSyn | Str | DAT |
|-----|------|-----|-----|
| 45 | 45 | 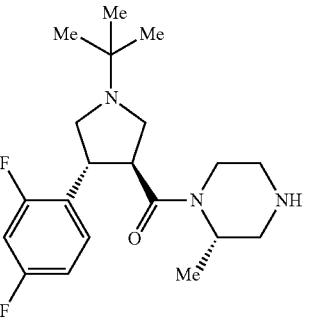 [SMILES: C[C@H]1CNCCN1C(=O)[C@@H]1CN(C(C)(C)C)C[C@H]1c1ccc(F)cc1F] | ESI+: 366 |

TABLE 16-continued
| PEx | PSyn | Str | DAT |
|---|---|---|---|
| 46 | 45 | 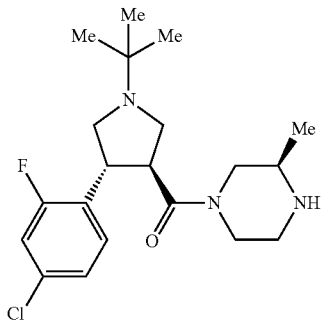 [SMILES: C[C@@H]1CN(C(=O)[C@@H]2CN(C(C)(C)C)C[C@H]2c2ccc(Cl)cc2F)CCN1] | ESI+: 382 |
| 47 | 47 | 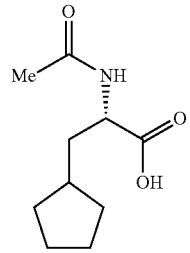 | ESI+: 200 |
| 48 | 47 | 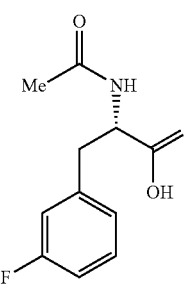 | ESI+: 226 |
| 49 | 49 | 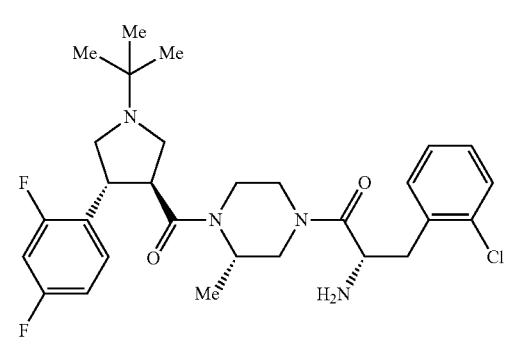 [SMILES: C[C@H]1CN(C(=O)[C@@H](N)Cc2ccccc2Cl)CCN1C(=O)[C@@H]1CN(C(C)(C)C)C[C@H]1c1ccc(F)cc1F] | ESI+: 547 |

TABLE 17
| PEx | PSyn | Str | DAT |
|---|---|---|---|
| 50 | 49 | 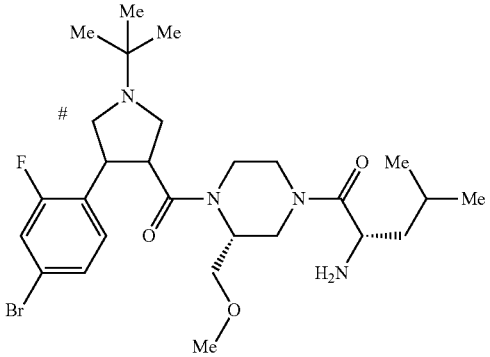 [SMILES: COC[C@H]1CN(C(=O)[C@@H](N)CC(C)C)CCN1C(=O)C1CN(C(C)(C)C)CC1c1ccc(Br)cc1F] | ESI+: 571 |
| 51 | 51 | 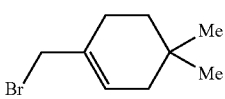 | CI+: 203 |
| 52 | 52 | 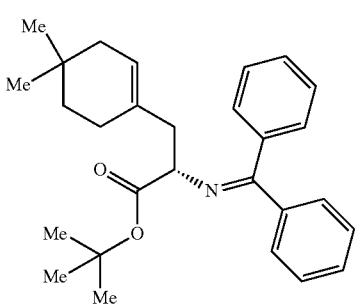 [SMILES: CC1(C)CC=C(C[C@H](N=C(c2ccccc2)c2ccccc2)C(=O)OC(C)(C)C)CC1] | ESI+: 418 |
| 53 | 53 | 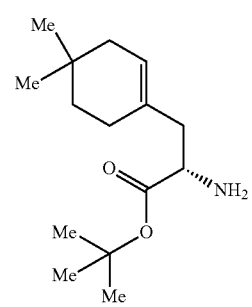 [SMILES: CC1(C)CC=C(C[C@H](N)C(=O)OC(C)(C)C)CC1] | ESI+: 254 |
| 54 | 54 | 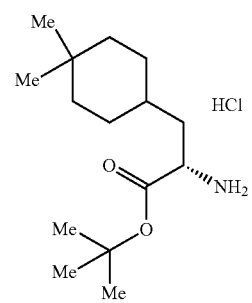 [SMILES: CC1(C)CCC(C[C@H](N)C(=O)OC(C)(C)C)CC1 ; Cl] | ESI+: 256 |

TABLE 18
| PEx | PSyn | Str | DAT |
|---|---|---|---|
| 55 | 54 | 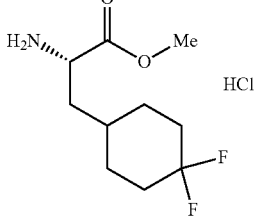 | ESI+: 222 |
| 56 | 56 | 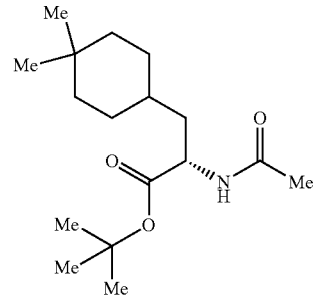 [SMILES: CC(=O)N[C@@H](CC1CCC(C)(C)CC1)C(=O)OC(C)(C)C] | ESI+: 298 |
| 57 | 56 | 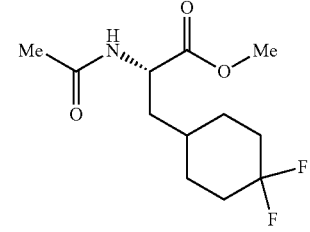 [SMILES: COC(=O)[C@H](CC1CCC(F)(F)CC1)NC(C)=O] | ESI+: 264 |
| 58 | 80 | 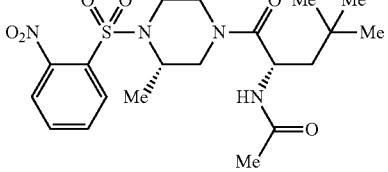 | ESI+: 455 |
| 59 | 80 | 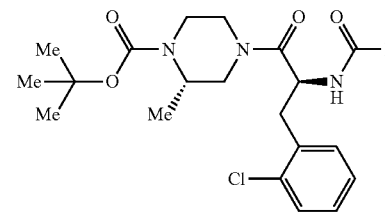 | ESI+: 424 |
TABLE 19
| PEx | PSyn | Str | DAT |
|---|---|---|---|
| 60 | 60 | 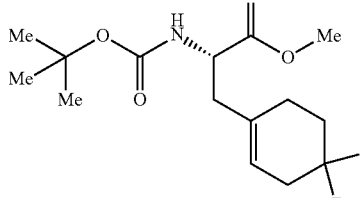 | ESI+: 242 |
TABLE 19-continued
| PEx | PSyn | Str | DAT |
|---|---|---|---|
| 61 | 61 | 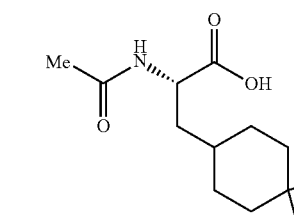 | ESI+: 320 |
| 62 | 62 | 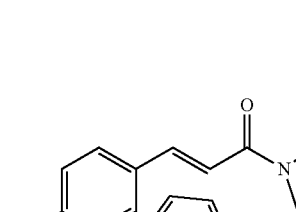 | ESI+: 250 |
| 63 | 63 | 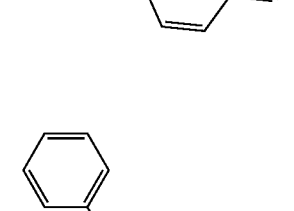 | ESI+: 326 |
| 64 | 63 | 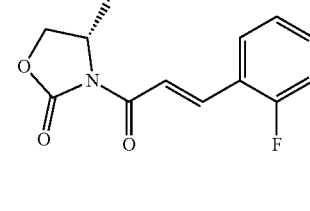 | ESI+: 404 |
| 65 | 65 | 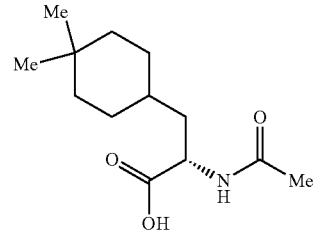 [SMILES: CC(=O)N[C@@H](CC1CCC(C)(C)CC1)C(=O)O] | ESI+: 400 |

TABLE 20

| PEx | PSyn | Str | DAT |
|---|---|---|---|
| 66 | 66 | | ESI+: 343 |
| 67 | 67 | | ESI+: 425 |
| 68 | 67 | | ESI+: 505 |
| 69 | 67 | | APCI/ESI+: 477 |

TABLE 21

| PEx | PSyn | Str | DAT |
|---|---|---|---|
| 70 | 67 | | ESI+: 442 |
| 71 | 71 | | ESI+: 266 |
| 72 | 71 | | ESI+: 346 |
| 73 | 71 | | APCI/ESI+: 318 |
| 74 | 74 | | ESI+: 270 |
| 75 | 75 | | EI: 208 |

TABLE 22

| PEx | PSyn | Str | DAT |
|---|---|---|---|
| 76 | 76 | (structure) | ESI+: 274 |
| 77 | 77 | (structure) | ESI+: 327 |
| 78 | 78 | (structure) | ESI+: 309 |

TABLE 22-continued

| PEx | PSyn | Str | DAT |
|---|---|---|---|
| 79 | 79 | (structure) | ESI+: 328 |
| 80 | 80 | (structure) | ESI+: 469 |
| 81 | 81 | (structure) | ESI+: 385 |

TABLE 23

| PEx | PSyn | Str | DAT |
|---|---|---|---|
| 82 | 82 | (structure) | ESI+: 427 |
| 83 | 83 | (structure) | ESI+: 382 |
| 84 | 84 | (structure) | ESI+: 324 |

TABLE 23-continued

| PEx | PSyn | Str | DAT |
|---|---|---|---|
| 85 | 85 | | ESI+: 479 |
| 86 | 86 | | ESI+: 297 |

TABLE 24

| PEx | PSyn | Str | DAT |
|---|---|---|---|
| 87 | 87 | | ESI+: 283 |
| 88 | 88 | | ESI−: 411 |
| 89 | 89 | | ESI+: 519 |

TABLE 24-continued
| PEx | PSyn | Str | DAT |
|---|---|---|---|
| 90 | 90 | 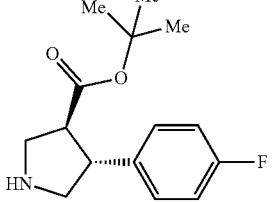 | NMR2: 1.40 (9H, s), 2.83-2.92 (2H, m), 3.25-3.36 (2H, m), 3.37-3.51 (2H, m), 6.95-7.04 (2H, m), 7.17-7.24 (2H, m) |
| 91 | 91 | 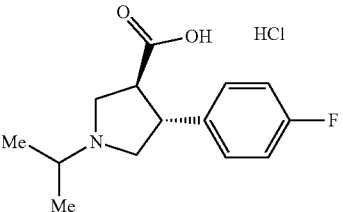 [SMILES: CC(C)N1C[C@@H](C(=O)O)[C@H](c2ccc(F)cc2)C1 ; Cl] | ESI+: 252 |
TABLE 25
| PEx | PSyn | Str | DAT |
|---|---|---|---|
| 92 | 92 | 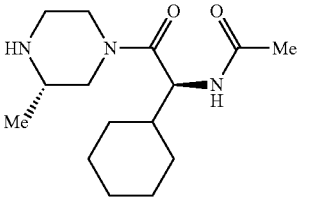 [SMILES: CC(=O)N[C@H](C(=O)N1CCN[C@@H](C)C1)C1CCCCC1] | ESI+: 282 |
| 93 | 74 | 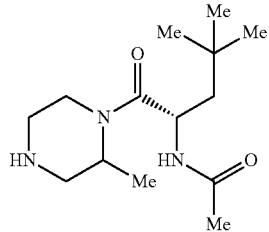 [SMILES: CC(=O)N[C@@H](CC(C)(C)C)C(=O)N1CCNCC1C] | ESI+: 270 |
| 94 | 94 | 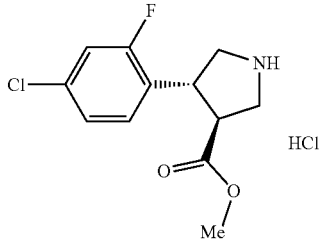 [SMILES: COC(=O)[C@@H]1CNC[C@H]1c1ccc(Cl)cc1F ; Cl] | ESI+: 258 |
TABLE 25-continued
| PEx | PSyn | Str | DAT |
|---|---|---|---|
| 95 | 94 | 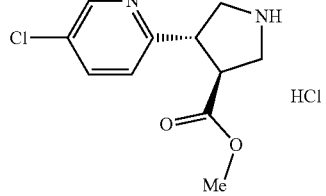 | ESI+: 241 |
| 96 | 96 | 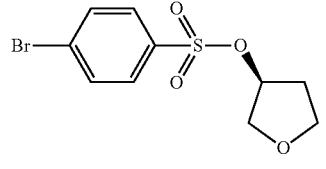 [SMILES: O=S(=O)(O[C@H]1CCOC1)c1ccc(Br)cc1] | ESI+: 329 [M + Na]+ |
| 97 | 96 | 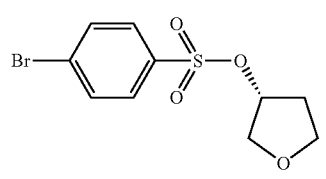 [SMILES: O=S(=O)(O[C@@H]1CCOC1)c1ccc(Br)cc1] | ESI+: 331 [M + Na]+ |

TABLE 26

| PEx | PSyn | Str | DAT |
|---|---|---|---|
| 98 | 98 | | ESI+: 565 |
| 99 | 98 | | ESI+: 566 |
| 100 | 98 | | ESI+: 325 |
| 101 | 101 | | ESI+: 188 |
| 102 | 102 | | CI+: 232 |

TABLE 26-continued
| PEx | PSyn | Str | DAT |
|---|---|---|---|
| 103 | 103 | | APCI/ESI+: 286 [M − Boc + H]+ |
TABLE 27
| PEx | PSYn | Str | DAT |
|---|---|---|---|
| 104 | 104 | | ESI+: 308 |
| 105 | 33 | | ESI+: 427 |
| 106 | 80 | | ESI+: 469 |
TABLE 27-continued
| PEx | PSYn | Str | DAT |
|---|---|---|---|
| 107 | 74 | | ESI+: 284 |
| 108 | 81 | | ESI−: 341 |
TABLE 28
| PEx | PSyn | Str | DAT |
|---|---|---|---|
| 109 | 18 | 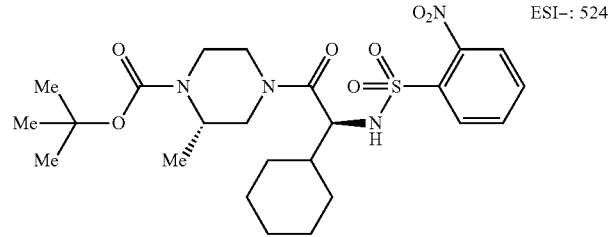 | ESI−: 524 |

TABLE 28-continued

| PEx | PSyn | Str | DAT |
|---|---|---|---|
| 110 | 83 | | ESI+: 340 |
| 111 | 80 | | ESI+: 382 |
| 112 | 65 | | ESI+: 382 [M + Na]+ |
| 113 | 67 | | ESI+: 459 |
| 114 | 71 | | ESI+: 300 |

TABLE 29

| PEx | PSyn | Str | DAT |
|---|---|---|---|
| 115 | 63 | | ESI+: 382 [M + Na]+ |
| 116 | 67 | | ESI+: 493 |
| 117 | 86 | | ESI+: 350 |
| 118 | 82 | | ESI+: 443 |
| 119 | 88 | | ESI+: 429 |

TABLE 30
| PEx | PSyn | Str | DAT |
|---|---|---|---|
| 120 | 1 | 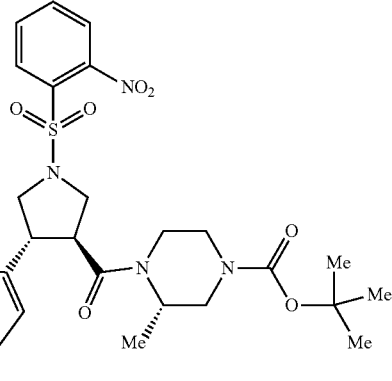 | ESI+: 633 [M + Na]+ |
| 121 | 10 | 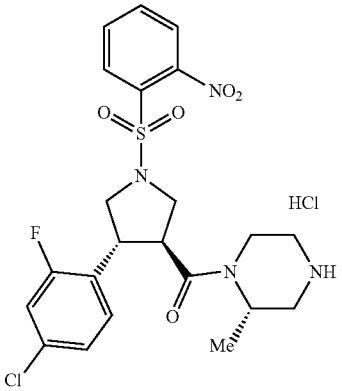 [SMILES: C[C@H]1CNCCN1C(=O)[C@@H]1CN(S(=O)(=O)c2ccccc2[N+](=O)[O-])C[C@H]1c1ccc(Cl)cc1F ; Cl] | ESI+: 511 |
| 122 | 18 | 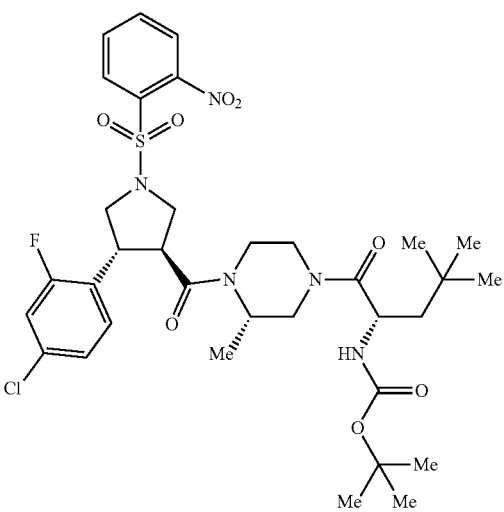 [SMILES: C[C@H]1CN(C(=O)[C@H](CC(C)(C)C)NC(=O)OC(C)(C)C)CCN1C(=O)[C@@H]1CN(S(=O)(=O)c2ccccc2[N+](=O)[O-])C[C@H]1c1ccc(Cl)cc1F] | ESI+: 761 [M + Na]+ |

TABLE 30-continued
| PEx | PSyn | Str | DAT |
|---|---|---|---|
| 123 | 33 | 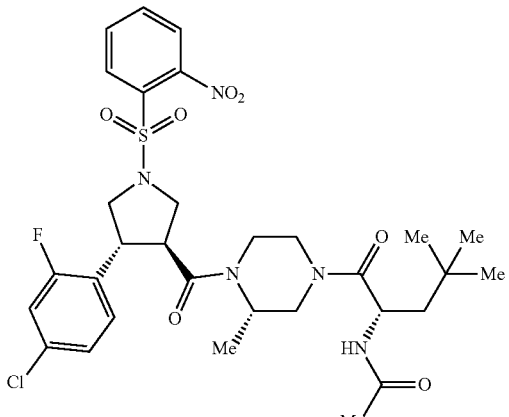 | ESI+: 638 |
TABLE 31
| PEx | PSyn | Str | DAT |
|---|---|---|---|
| 124 | 80 | 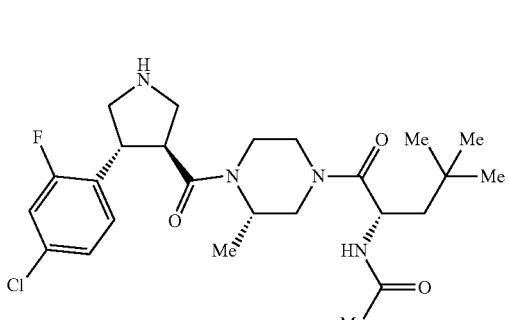 | ESI+: 702 [M + Na]+ |
| 125 | 85 | | ESI+: 495 |

TABLE 31-continued
| PEx | PSyn | Str | DAT |
|---|---|---|---|
| 126 | 67 | 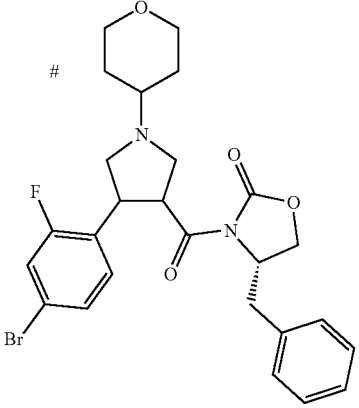 [SMILES: O=C1OC[C@H](Cc2ccccc2)N1C(=O)C1CN(C2CCOCC2)CC1c1ccc(Br)cc1F] | ESI+: 533 |
| 127 | 63 | 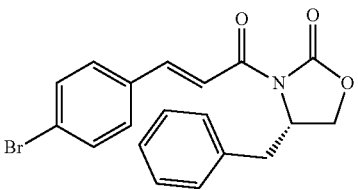 [SMILES: O=C(/C=C/c1ccc(Br)cc1)N1C(=O)OC[C@@H]1Cc1ccccc1] | ESI+: 408 [M + Na]+ |
TABLE 32
| PEx | PSyn | Str | DAT |
|---|---|---|---|
| 128 | 67 | 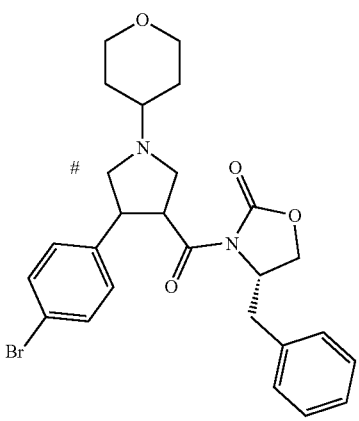 [SMILES: O=C1OC[C@H](Cc2ccccc2)N1C(=O)C1CN(C2CCOCC2)CC1c1ccc(Br)cc1] | ESI+: 515 |
| 129 | 71 | 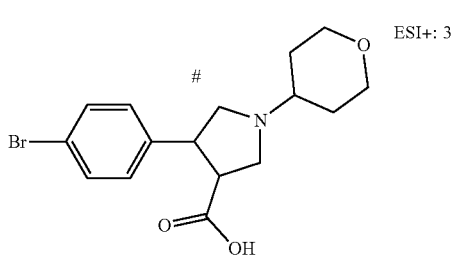 | ESI+: 354 |

TABLE 32-continued
| PEx | PSyn | Str | DAT |
|---|---|---|---|
| 130 | 10 | 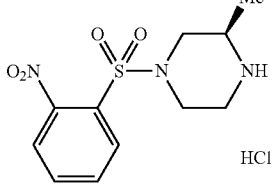 | APCI/ESI+: 286 |
| 131 | 18 | 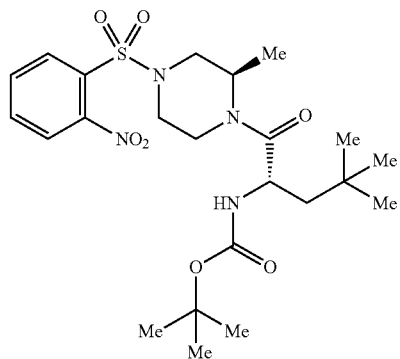 [SMILES: C[C@@H]1CN(S(=O)(=O)c2ccccc2[N+](=O)[O-])CCN1C(=O)[C@H](CC(C)(C)C)NC(=O)OC(C)(C)C] | ESI+: 535 [M + Na]+ |
| 132 | 33 | 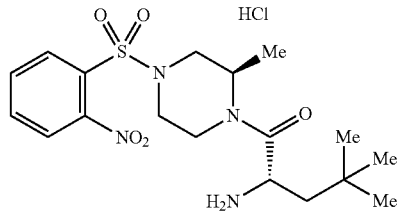 [SMILES: Cl ; C[C@@H]1CN(S(=O)(=O)c2ccccc2[N+](=O)[O-])CCN1C(=O)[C@@H](N)CC(C)(C)C] | ESI+: 413 |
TABLE 33
| PEx | PSyn | Str | DAT |
|---|---|---|---|
| 133 | 80 | 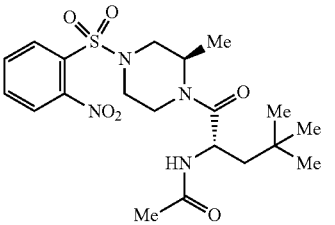 [SMILES: CC(=O)N[C@@H](CC(C)(C)C)C(=O)N1CCN(S(=O)(=O)c2ccccc2[N+](=O)[O-])C[C@H]1C] | ESI+: 477 [M + Na]+ |
| 134 | 67 | 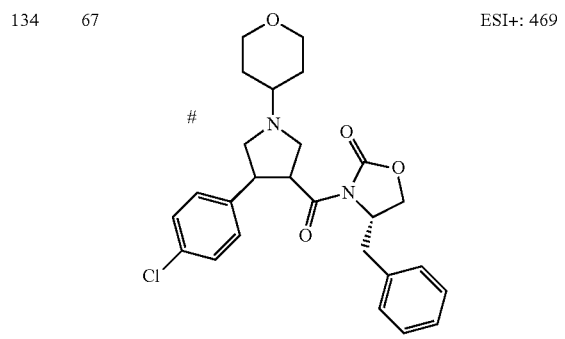 | ESI+: 469 |
| 135 | 71 | 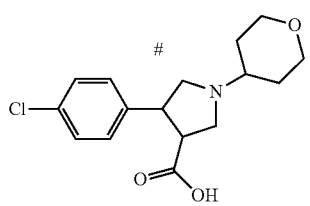 [SMILES: O=C(O)C1CN(C2CCOCC2)CC1c1ccc(Cl)cc1] | ESI+: 310 |
| 136 | 88 | 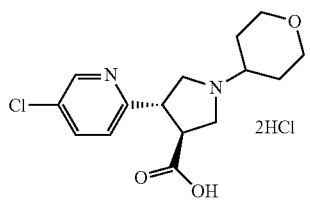 [SMILES: O=C(O)[C@@H]1CN(C2CCOCC2)C[C@H]1c1ccc(Cl)cn1] | ESI+: 311 |

TABLE 34

| PEx | PSyn | Str | DAT |
|---|---|---|---|
| 137 | 18 | (structure) | APCI/ESI+: 525 |
| 138 | 33 | (structure) | APCI/ESI+: 425 |
| 139 | 80 | (structure) | APCI/ESI+: 467 |
| 140 | 83 | (structure) | APCI/ESI+: 282 |
| 141 | 74 | (structure) | ESI+: 284 |

TABLE 35

| PEx | PSyn | Str | DAT |
|---|---|---|---|
| 142 | 18 | (structure) | ESI+: 527 |
| 143 | 71 | (structure) | ESI+: 372 |

TABLE 36

| Ex | Syn | Str | DAT |
|---|---|---|---|
| 1 | 1 | (structure with tert-butyl pyrrolidine, 2,4-difluorophenyl, dimethylpiperazine, tert-leucine acetamide) | ESI+: 550 |
| 2 | 1 | (structure with tert-butyl pyrrolidine, 2-fluoro-4-chlorophenyl, methylpiperazine, leucine acetamide) | ESI+: 538 |
| 3 | 6 | (structure with tetrahydropyranyl pyrrolidine, 2-fluoro-4-chlorophenyl, dimethylpiperazine, tert-leucine acetamide) HCl | ESI+: 594 |
| 4 | 4 | (structure with tert-butyl pyrrolidine, 2,4-difluorophenyl, dimethylpiperazine, tert-leucine acetamide) HCl | ESI+: 550<br>NMR1: 0.91-1.49 (24H, m), 1.62-1.98 (2H, m), 2.04-2.11 (3H, m), 2.26-5.57 (13H, m), 6.92-7.16 (2H, m), 8.05-8.53 (1H, m), 9.09-9.21 (1H, m) |

TABLE 37
| Ex | Syn | Str | DAT |
|---|---|---|---|
| 5 | 4 | 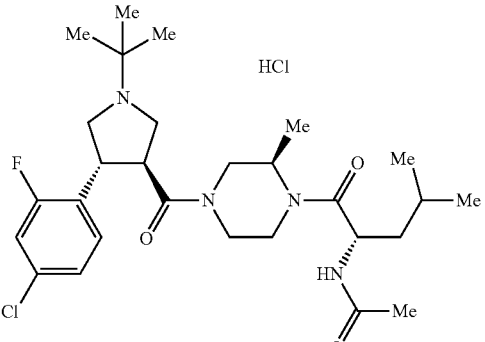 HCl | ESI+: 538<br>NMR1: 0.7-1.90 (21H, m), 2.07-2.14 (3H, m), 2.19-5.44 (14 H, m), 7.12-7.38 (2H, m), 8.03-8.51 (1H, m), 8.92-9.04 (1H, m) |
| 6 | | 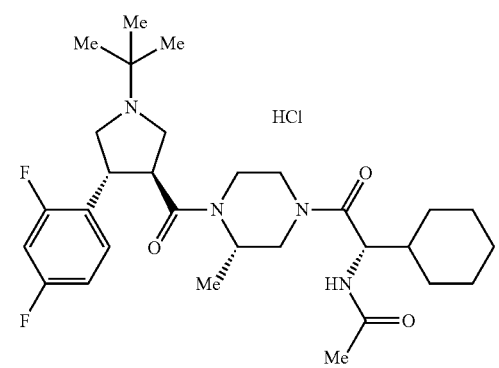 [SMILES: CC(=O)N[C@H](C(=O)N1CCN(C(=O)[C@@H]2CN(C(C)(C)C)C[C@H]2c2ccc(F)cc2F)[C@@H](C)C1)C1CCCCC1 ; Cl] HCl | ESI+: 548<br>NMR1: 0.97-2.02 (23H, m), 2.07-2.17 (3H, m), 2.21-5.23 (14H, m), 6.92-7.13 (2H, m), 8.08-8.50 (1H, m), 8.78-8.94 (1H, m) |
| 7 | 6 | 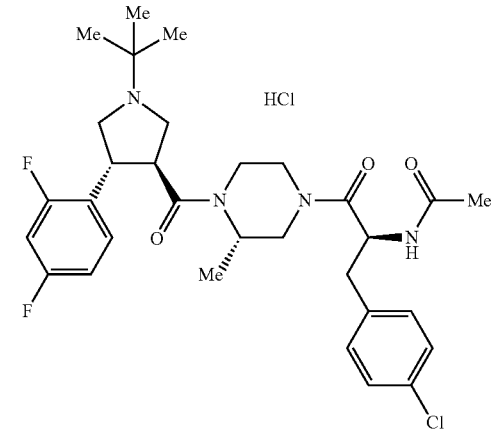 [SMILES: CC(=O)N[C@@H](Cc1ccc(Cl)cc1)C(=O)N1CCN(C(=O)[C@@H]2CN(C(C)(C)C)C[C@H]2c2ccc(F)cc2F)[C@@H](C)C1 ; Cl] HCl | ESI+: 589 |
| 8 | 6 | 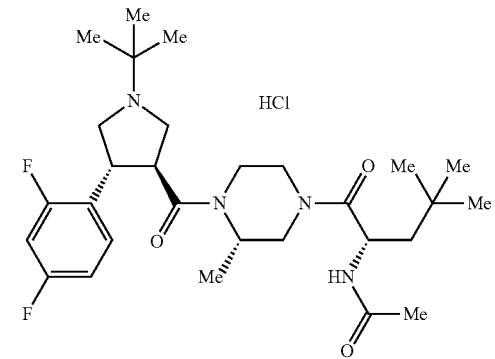 [SMILES: CC(=O)N[C@@H](CC(C)(C)C)C(=O)N1CCN(C(=O)[C@@H]2CN(C(C)(C)C)C[C@H]2c2ccc(F)cc2F)[C@@H](C)C1 ; Cl] HCl | ESI+: 535<br>NMR1: 0.74-1.48 (21H, m), 1.51-1.96 (2H, m), 2.01-2.12 (3H, m), 2.20-5.49 (14H, m), 6.88-7.14 (2H, m), 8.03-8.50 (1H, m), 9.07-9.22 (1H, m) |

TABLE 38
| Ex | Syn | Str | DAT |
|---|---|---|---|
| 9 | 6 | 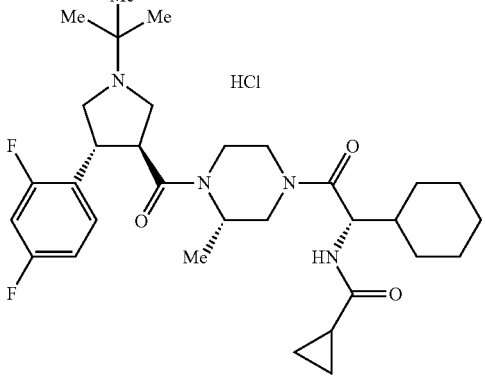 | ESI+: 573 |
| 10 | 6 | 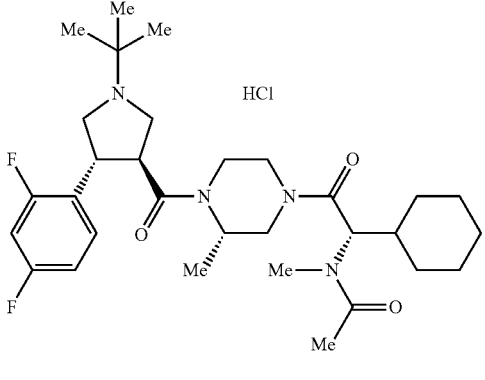 [SMILES: CC(=O)N(C)[C@H](C(=O)N1CCN(C(=O)[C@@H]2CN(C(C)(C)C)C[C@H]2c2ccc(F)cc2F)[C@@H](C)C1)C1CCCCC1 ; Cl] | ESI+: 561 |
| 11 | 6 | 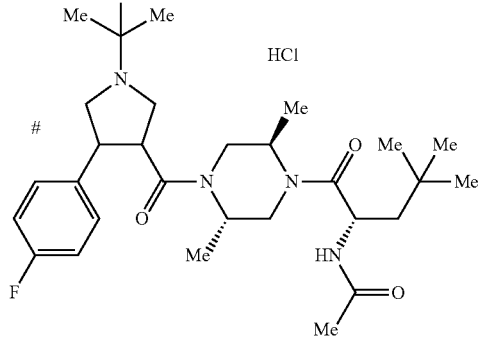 | ESI+: 531<br>NMR1: 0.87-1.50 (24H, m), 1.61-1.98 (2H, m), 2.04-2.11 (3H, m), 2.22-5.55 (13H, m), 7.04-7.17 (2H, m), 7.66-7.97 (2H, m), 9.09-9.21 (1H, m) |
| 12 | 6 | 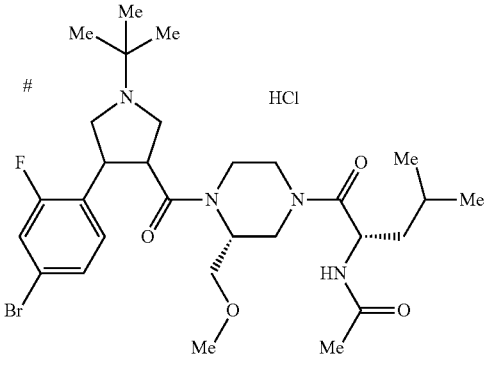 [SMILES: COC[C@H]1CN(C(=O)[C@H](CC(C)C)NC(C)=O)CCN1C(=O)C1CN(C(C)(C)C)CC1c1ccc(Br)cc1F ; Cl] | ESI+: 611 |

TABLE 39
| Ex | Syn | Str | DAT |
|----|-----|-----|-----|
| 13 | 6 | 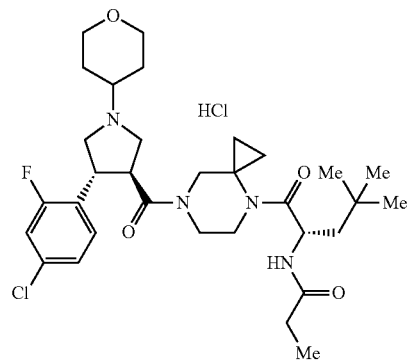 [SMILES: CCC(=O)N[C@@H](CC(C)(C)C)C(=O)N1CCN(C(=O)[C@@H]2CN(C3CCOCC3)C[C@H]2c2ccc(Cl)cc2F)CC12CC2 ; Cl] | ESI+: 606 |
| 14 | 6 | 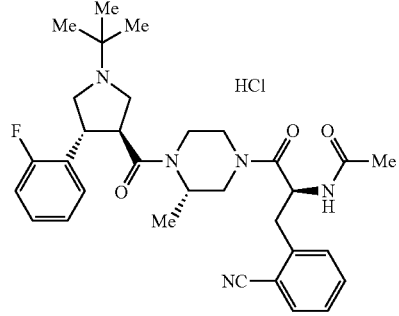 [SMILES: CC(=O)N[C@@H](Cc1ccccc1C#N)C(=O)N1CCN(C(=O)[C@@H]2CN(C(C)(C)C)C[C@H]2c2ccccc2F)[C@@H](C)C1 ; Cl] | ESI+: 581 |
| 15 | 6 | 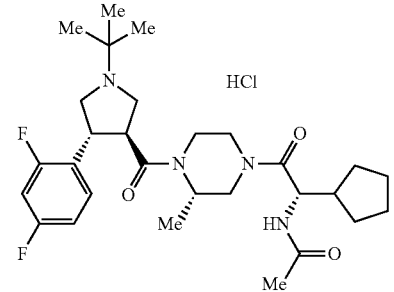 [SMILES: CC(=O)N[C@H](C(=O)N1CCN(C(=O)[C@@H]2CN(C(C)(C)C)C[C@H]2c2ccc(F)cc2F)[C@@H](C)C1)C1CCCC1 ; Cl] | ESI+: 533 |
| 16 | 16 | 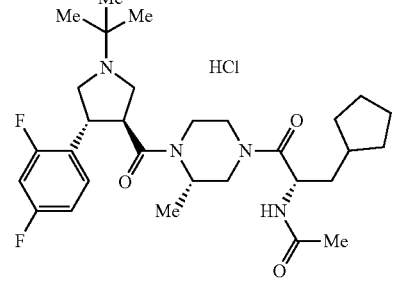 | ESI+: 548 |
TABLE 40
| Ex | Syn | Str | DAT |
|----|-----|-----|-----|
| 17 | 16 | 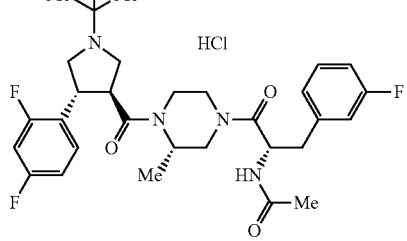 | ESI+: 573 |
| 18 | 18 | 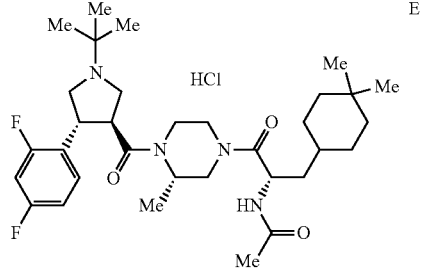 | ESI+: 590 |
| 19 | 18 | 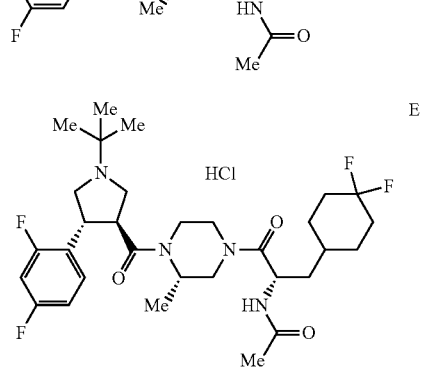 | ESI+: 598 |
| 20 | 20 | 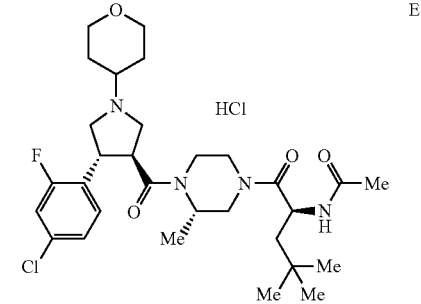 | ESI+: 579 |
TABLE 41
| Ex | Syn | Str | DAT |
|----|-----|-----|-----|
| 21 | 20 | 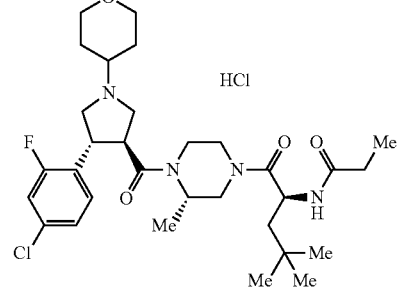 | ESI+: 593 |

TABLE 41-continued

| Ex | Syn | Str | DAT |
|---|---|---|---|
| 22 | 20 | | ESI+: 624 HCl |
| 23 | 20 | | ESI+: 535 HCl |
| 24 | 24 | | ESI+: 522 HCl |

TABLE 42

| Ex | Syn | Str | DAT |
|---|---|---|---|
| 25 | 24 | | ESI+: 562 HCl |
| 26 | 24 | | ESI+: 494 HCl |

TABLE 42-continued

| Ex | Syn | Str | DAT |
|---|---|---|---|
| 27 | 24 | | ESI+: 534 HCl |
| 28 | 28 | | ESI+: 575 2HCl |

TABLE 43

| Ex | Syn | Str | DAT |
|---|---|---|---|
| 29 | 29 | | ESI+: 601 HCl |
| 30 | 30 | | ESI+: 506 2HCl |
| 31 | 4 | | ESI+: 566 HCl |

TABLE 43-continued

| Ex | Syn | Str | DAT |
|---|---|---|---|
| 32 | 16 | | ESI+: 562 |

TABLE 44

| Ex | Syn | Str | DAT |
|---|---|---|---|
| 33 | 4 | | ESI+: 565 |
| 34 | 20 | | ESI+: 518 |
| 35 | 20 | | ESI+: 565 |
| 36 | 20 | | ESI+: 552 |

TABLE 45

| Ex | Syn | Str | DAT |
|---|---|---|---|
| 37 | 20 | | ESI+: 624 |
| 38 | 20 | | ESI+: 607 |
| 39 | 20 | | ESI+: 562 |

TABLE 46

| Ex | Syn | Str | DAT |
|---|---|---|---|
| 40 | 20 | | ESI+: 563 |

TABLE 46-continued

| Ex | Syn | Str | DAT |
|---|---|---|---|
| 41 | 20 | (structure) | ESI+: 575 |
| 42 | 24 | (structure) | ESI+: 548 |

TABLE 47

| Ex | Syn | Str | DAT |
|---|---|---|---|
| 43 | 24 | (structure) | ESI+: 534 |

INDUSTRIAL APPLICABILITY

The compound of the formula (I) or a salt thereof is a compound having an $MC_4$ receptor agonistic activity, and is expected to be useful as an active ingredient of a pharmaceutical composition for preventing or treating bladder and/or urinary tract diseases, particularly, underactive bladder, hypotonic bladder, acontractile bladder, detrusor underactivity, neurogenic bladder, urethral relaxation failure, detrusor-external urethral sphincter dyssynergia, and voiding dysfunctions in benign prostatic hyperplasia.

The invention claimed is:

1. A compound of formula (I) or a salt thereof:

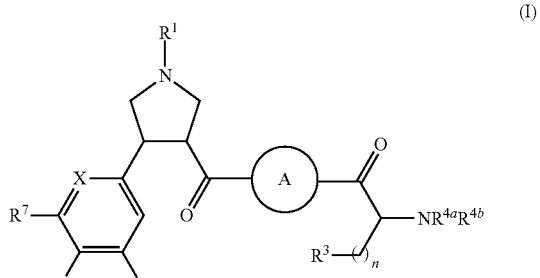

(I)

[[(wherein,
Ring A represents

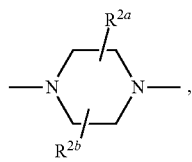

$R^1$ represents $C_{1-6}$ alkyl which may be substituted, $C_{3-8}$ cycloalkyl which may be substituted, or a saturated hetero ring which may be substituted, $R^{2a}$ and $R^{2b}$ are the same as or different from each other and each represent H or $C_{1-6}$ alkyl which may be substituted, $R^{2a}$ and $R^{2b}$ do not simultaneously represent H, in a case where $R^{2a}$ and $R^{2b}$ are bonded to the same carbon, $R^{2a}$, $R^{2b}$, and the carbon atom to which they are bonded may form a saturated hydrocarbon ring together, $R^3$ represents $C_{1-6}$ alkyl which may be substituted, $C_{3-8}$ cycloalkyl which may be substituted, or phenyl which may be substituted, $R^{4a}$ represents H, $C_{1-6}$ alkyl, —C(O)$R^9$, or —S(O)$_2R^9$, $R^{4b}$ represents H or $C_{1-6}$ alkyl, X represents $CR^8$ or N, $R^5$, $R^6$, $R^7$, and $R^8$ are the same as or different from each other and each represent H or halogen, $R^9$ represents $C_{1-6}$ alkyl which may be substituted or $C_{3-8}$ cycloalkyl which may be substituted, and n represents 0 or 1.

2. The compound or salt thereof according to claim 1, wherein $R^1$ represents $C_{1-6}$ alkyl which may be substituted, $C_{3-8}$ cycloalkyl, or an oxygen-containing saturated hetero ring, $R^3$ represents $C_{1-6}$ alkyl, $C_{3-8}$ cycloalkyl which may be substituted, or phenyl which may be substituted, $R^{4a}$ represents H, $C_{1-6}$ alkyl, —C(O)$R^9$, or —S(O)$_2R^9$, $R^{4b}$ represents H or $C_{1-6}$ alkyl, in a case where $R^{4a}$ represents H, $R^{4b}$ also represents H, and in a case where $R^{4a}$ represents $C_{1-6}$ alkyl, $R^{4b}$ also represents $C_{1-6}$ alkyl, and $R^9$ represents $C_{1-6}$ alkyl or $C_{3-8}$ cycloalkyl.

3. The compound or salt thereof according to claim 2, wherein
Ring A is

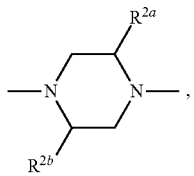

R¹ represents $C_{1-6}$ alkyl or an oxygen-containing saturated hetero ring,
$R^{2a}$ and $R^{2b}$ are the same as or different from each other and each represent H or $C_{1-6}$ alkyl,
$R^{2a}$ and $R^{2b}$ do not simultaneously represent H,
R³ represents $C_{1-6}$ alkyl, $C_{3-8}$ cycloalkyl, or phenyl which may be substituted with one or two substituents selected from the group consisting of halogen and cyano,
$R^{4a}$ represents —C(O)R⁹ or —S(O)₂R⁹,
$R^{4b}$ represents H,
R⁵ represents H,
R⁶ represents halogen,
R⁷ represents H,
R⁸ represents H or halogen, and
R⁹ represents $C_{1-6}$ alkyl.

4. The compound or salt thereof according to claim 3, wherein
Ring A is

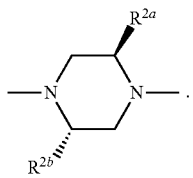

5. The compound or salt thereof according to claim 4, wherein
R³ represents $C_{1-6}$ alkyl, $C_{3-8}$ cycloalkyl, or phenyl which may be substituted with one cyano group,
$R^{4a}$ represents —C(O)R⁹,
$R^{4b}$ represents H, and
X represents CR⁸.

6. The compound or salt thereof according to claim 5, wherein
R¹ represents $C_{1-6}$ alkyl,
when n represents 0, R³ represents $C_{3-8}$ cycloalkyl, and
when n represents 1, R³ represents $C_{1-6}$ alkyl.

7. The compound or salt thereof according to claim 6, wherein
R¹ represents tert-butyl,
$R^{2a}$ and $R^{2b}$ are the same as or different from each other and each represent H or methyl,
$R^{2a}$ and $R^{2b}$ do not simultaneously represent H,
when n represents 0, R³ represents cyclohexyl,
when n represents 1, R³ represents isopropyl or tert-butyl,
X represents CR⁸,
R⁶ represents F or Cl,
R⁸ represents H or F, and
R⁹ represents methyl.

8. The compound or salt thereof according to claim 1, wherein the compound is selected from the group consisting of:
N-{(1S)-2-[(3S)-4-{[(3S,4R)-1-tert-butyl-4-(2,4-difluorophenyl)pyrrolidin-3-yl]carbonyl}-3-methylpiperazin-1-yl]-1-cyclohexyl-2-oxoethyl}acetamide,
N-{(2S)-1-[(3S)-4-{[(3S,4R)-1-tert-butyl-4-(2,4-difluorophenyl)pyrrolidin-3-yl]carbonyl}-3-methylpiperazin-1-yl]-4,4-dimethyl-1-oxopentan-2-yl}acetamide,
N-{(2S)-1-[(2R,5S)-4-{[(3S,4R)-1-tert-butyl-4-(2,4-difluorophenyl)pyrrolidin-3-yl]carbonyl}-2,5-dimethylpiperazin-1-yl]-4,4-dimethyl-1-oxopentan-2-yl}acetamide,
N-{(2S)-1-[(2R,5 S)-4-{[1-tert-butyl-4-(4-fluorophenyl)pyrrolidin-3-yl]carbonyl}-2,5-dimethylpiperazin-1-yl]-4,4-dimethyl-1-oxopentan-2-yl}acetamide, and
N-{(2S)-1-[(2R)-4-{[(3S,4R)-1-tert-butyl-4-(4-chloro-2-fluorophenyl)pyrrolidin-3-yl]carbonyl}-2-methylpiperazin-1-yl]-4-methyl-1-oxopentan-2-yl}acetamide.

9. A pharmaceutical composition, comprising a compound or salt thereof according to claim 8 and a pharmaceutically acceptable excipient.

10. A method for treating a bladder and/or urinary tract disease, comprising administering to a subject in need thereof an effective amount of a compound or salt thereof according to claim 8.

11. The compound or salt thereof according to claim 8, which is N-{(1S)-2-[(3S)-4-{[(3S,4R)-1-tert-butyl-4-(2,4-difluorophenyl)pyrrolidin-3-yl]carbonyl}-3-methylpiperazin-1-yl]-1-cyclohexyl-2-oxoethyl}acetamide or a salt thereof.

12. The compound or salt thereof according to claim 8, which is N-{(2S)-1-[(3S)-4-{[(3S,4R)-1-tert-butyl-4-(2,4-difluorophenyl)pyrrolidin-3-yl]carbonyl}-3-methylpiperazin-1-yl]-4,4-dimethyl-1-oxopentan-2-yl}acetamide or a salt thereof.

13. The compound or salt thereof according to claim 8, which is N-{(2S)-1-[(2R,5S)-4-{[(3S,4R)-1-tert-butyl-4-(2,4-difluorophenyl)pyrrolidin-3-yl]carbonyl}-2,5-dimethylpiperazin-1-yl]-4,4-dimethyl-1-oxopentan-2-yl}acetamide or a salt thereof.

14. The compound or salt thereof according to claim 8, which is N-{(2S)-1-[(2R,5S)-4-{[1-tert-butyl-4-(4-fluorophenyl)pyrrolidin-3-yl]carbonyl}-2,5-dimethylpiperazin-1-yl]-4,4-dimethyl-1-oxopentan-2-yl}acetamide or a salt thereof.

15. The compound or salt thereof according to claim 8, which is N-{(2S)-1-[(2R)-4-{[(3S,4R)-1-tert-butyl-4-(4-chloro-2-fluorophenyl)pyrrolidin-3-yl]carbonyl}-2-methylpiperazin-1-yl]-4-methyl-1-oxopentan-2-yl}acetamide or a salt thereof.

* * * * *